United States Patent
Bunnett et al.

(10) Patent No.: US 11,324,832 B2
(45) Date of Patent: May 10, 2022

(54) TRIPARTITE MODULATORS OF ENDOSOMAL G PROTEIN-COUPLED RECEPTORS

(71) Applicant: Endosome Therapeutics, Inc., Pottstown, PA (US)

(72) Inventors: Nigel W. Bunnett, Parkville (AU); Christopher John Porter, Parkville (AU); Derek Cole, San Diego, CA (US); Gareth Hicks, Wellesley, MA (US); Junya Shirai, Osaka (JP); Gavin Hirst, San Diego, CA (US); Luigi Aurelio, Clayton (AU)

(73) Assignee: Endosome Therapeutics, Inc., Pottstown, PA (US)

(*) Notice: Subject to any disclaimer, the term of this patent is extended or adjusted under 35 U.S.C. 154(b) by 0 days.

(21) Appl. No.: 16/064,061

(22) PCT Filed: Dec. 21, 2016

(86) PCT No.: PCT/US2016/068075
§ 371 (c)(1),
(2) Date: Jun. 20, 2018

(87) PCT Pub. No.: WO2017/112792
PCT Pub. Date: Jun. 29, 2017

(65) Prior Publication Data
US 2019/0000981 A1    Jan. 3, 2019

Related U.S. Application Data

(60) Provisional application No. 62/291,161, filed on Feb. 4, 2016.

(30) Foreign Application Priority Data

Dec. 22, 2015 (AU) .............. 2015905333

(51) Int. Cl.
| | | |
|---|---|---|
| A61K 47/60 | (2017.01) | |
| A61K 47/54 | (2017.01) | |
| A61K 47/64 | (2017.01) | |
| A61P 43/00 | (2006.01) | |
| A61K 31/44 | (2006.01) | |
| A61K 31/575 | (2006.01) | |

(52) U.S. Cl.
CPC ............ *A61K 47/554* (2017.08); *A61K 31/44* (2013.01); *A61K 31/575* (2013.01); *A61K 47/60* (2017.08); *A61K 47/64* (2017.08); *A61P 43/00* (2018.01)

(58) Field of Classification Search
CPC ................................... A61K 47/60
See application file for complete search history.

(56) References Cited

U.S. PATENT DOCUMENTS

| | | |
|---|---|---|
| 2003/0148449 A1 | 8/2003 | Kuliopulos et al. |
| 2006/0004195 A1 | 1/2006 | Deng |
| 2016/0052982 A1 | 2/2016 | Cohen |

FOREIGN PATENT DOCUMENTS

| | | |
|---|---|---|
| EP | 3018126 A1 | 5/2016 |
| JP | 2000247957 | 9/2000 |
| JP | 2002537382 | 11/2002 |
| JP | 2004504400 | 2/2004 |
| JP | 2004506718 | 3/2005 |
| WO | 2005/097199 A1 | 10/2005 |
| WO | 2006/004195 A1 | 1/2006 |
| WO | 2014/168721 A2 | 10/2014 |

OTHER PUBLICATIONS

Banker, Gilbert. Modern Pharmaceutics 3rd ed. Marcel Dekker, Inc. New York, 1996.*
Doyle et al., "A Two-Step Strategy to Enhance Activity of Low Potency Peptides," *PLoS One*, 9(11): e110502 (Nov. 12, 2014).
European Patent Office, International Search Report in International Patent Application No. PCT/US2016/068075 (dated Mar. 21, 2017).
European Patent Office, Written Opinion in International Patent Application No. PCT/US2016/068075 (dated Mar. 21, 2017).
Doyle et al., "A Two-Step Strategy to Enhance Activity of Low Potency Peptides" PLOS One, vol. 9, No. 11, p. e110502, 2014.
Mann et al., "Internalization of the Neurokinin 1 Receptor in Rat Myenteric Neurons," Neuroscience 1999, 91(1):353-362.
Schieb et al., "Structural Design, Solid-Phase Synthesis and Activity of Membrane-Anchored β-Secretase Inhibitors on Aβ Generation from Wild-Type and Swedish-Mutant APP," Chemistry European Journal 2010, 16: 14412-14423.
Versluis et al., "In Situ Modification of Plain Liposomes with Lipidated Coiled Coil Forming Peptides Induces Membrane Fusion," J. Am. Chem. Soc. 2013, 135: 8057-8062.
Zope et al., "In Vitro and In Vivo Supramolecular Modification of Biomembranes Using a Lipidated Coiled-Coil Motif," Angew. Chem. Int. Ed. 2013, 52: 14247-14251.

* cited by examiner

*Primary Examiner* — Paul V Ward
(74) *Attorney, Agent, or Firm* — Fish & Richardson P.C.

(57) ABSTRACT

The present invention relates to tripartite compounds comprising a modulator moiety for endosomal G protein-coupled receptors like neurokinin-1 receptor, a linker and a lipid anchor suitable for anchoring the tripartite compound into a plasma membrane. The present invention also relates to a prodrug and a pharmaceutical composition comprising the tripartite compound and the use of the tripartite compound for the treatment of a disease or disorder mediated by endosomal G protein-coupled receptors signalling like $NK_1R$ signalling.

10 Claims, 13 Drawing Sheets

Compound A

Compound B
Chemical Formula: $C_{83}H_{128}F_7N_5O_{19}$
Exact Mass: 1631.91
Molecular Weight: 1632.94

TRIPARTITE MODULATORS OF ENDOSOMAL G PROTEIN-COUPLED RECEPTORS

CROSS-REFERENCE TO RELATED APPLICATIONS

This patent application is the U.S. national phase of International Patent Application No. PCT/US2016/068075, filed on Dec. 21, 2016, which claims the benefit of Australian Patent Application No. 2015905333, filed Dec. 22, 2015, and U.S. Provisional Patent Application No. 62/291,161, filed Feb. 4, 2016, the disclosures of which are incorporated herein by reference in their entireties for all purposes.

FIELD OF THE INVENTION

The present invention relates to tripartite compounds and their uses, and in particular to tripartite compounds that act as modulators to endocytosed G protein-coupled receptors.

BACKGROUND OF THE INVENTION

G protein-coupled receptors (GPCRs) are the largest family of cell-surface receptors (~850 members), participate in most pathophysiological processes, and are the target of ~30% of therapeutic drugs (Audet, M. & Bouvier, M. *Nat Chem Biol* 2008, 4, 397-403). Cell-surface GPCRs interact with extracellular ligands and couple to heterotrimeric G proteins, which trigger signaling pathways that originate from the plasma membrane, including formation of second messengers, transactivation of growth factor receptors, and regulation of ion channels.

Until recently, it was widely assumed that activation of GPCRs, subsequent downstream signaling and signal termination took place exclusively at the plasma membrane. Plasma membrane signaling is terminated within minutes of activation via phosphorylation of the receptor by GPCR kinases that are selective for the active ligand-bound receptor conformation. Phosphorylated receptors then bind to β-arrestin (βarr) which sterically prevents coupling between receptor and G-protein, thus terminating agonist-mediated G-protein activation. βarrs further promote the transfer of ligand-bound receptor from the cell surface to early endosomes via dynamin- and clathrin-dependent endocytosis. Once endocytosed, the ligand and phosphate groups are removed from the GPCR and the receptor is either rapidly redistributed to the cell membrane or it is transported to a lysosome for degradation.

Recently, however, it has been discovered that a diverse range of GPCRs do not always follow the conventional paradigm. Studies have found that following ligand binding and activation of the receptor, some cell surface GPCRs internalise and redistribute into early endosomes where heterotrimeric G protein signaling is maintained for an extended period of time. Accordingly, rather than merely acting as a conduit for GPCR trafficking to recycling or degradatory pathways, endosomes can be a vital site of signal transduction (Murphy, J. E. et al. *Proc Natl Acad Sci USA* 2009, 106, 17615-17622). By recruiting GPCRs and mitogen-activated protein kinases to endosomes, βarrs can mediate endosomal GPCR signaling (Murphy, J. E. et al. *Proc Natl Acad Sci USA* 2009, 106, 17615-17622; DeFea, K. A. et al. *Proc Natl Acad Sci USA* 2000, 97, 11086-11091; DeFea, K. A. et al. *J Cell Biol* 2000, 148, 1267-1281), although some GPCRs elicit $G\alpha_s$-dependent signals from endosomes (Calebiro, D. et al. *PLoS Biol* 2009, 7, e1000172; Irannejad, R. et al. *Nature* 2013, 495, 534-538).

βarrs recruit diverse signaling proteins to activated receptors at plasma and endosomal membranes and are essential mediators of signaling. The MAPK cascades [ERK, c-Jun amino-terminal kinase (JNK), p38] are the most thoroughly characterized βarrs-dependent signaling pathways. The first evidence that βarrs are active participants in signaling was the observation that dominant negative mutants of βarr inhibited $\beta_2$AR-induced activation of ERK1/2 (Daaka Y, et al. *J Biol Chem* 1998, 273, 685-688). Subsequently, βarrs were found to couple $\beta_2$AR to c-Src and mediate ERK1/2 activation (Lutterall L. M. et al. *Science* 1999, 283, 655-661). βarrs similarly participate in ERK1/2 signaling by other GPCRs, including neurokinin-1 receptor ($NK_1R$), protease-activated receptor 2 ($PAR_2$), angiotensin II type 1A receptor ($AT_{1A}R$), and vasopressin V2 receptor ($V_2R$). These observations led to the view that βarrs are scaffolds that couple activated GPCRs with MAPK signaling complexes. βarrs thereby mediate a second wave of GPCR signaling that is distinct from G protein-dependent signaling at the plasma membrane.

Accordingly, modulating endocytosed GPCRs may advantageously provide a novel method of treating the vast number of diseases and disorders linked to this large family of receptors.

SUMMARY OF THE INVENTION

New tripartite compounds are provided that are suitable for the modulation of endosomal GPCR signalling. The tripartite compounds of the present invention can provide a novel method for the treatment and prevention of diseases and disorders mediated by these receptors.

Accordingly, in one aspect the present invention provides a tripartite compound for targeting endosomal GPCR signaling of the formula (I):

(I)

wherein

LA is a lipid anchor that promotes insertion of the compound into a plasma membrane;

L is a linker moiety of 1 nm to 50 nm in length; and

X is the modulator of the endosomal GPCR; or or a pharmaceutically acceptably salt thereof.

In one preferred embodiment the present invention provides a tripartite compound for targeting endosomal neurokinin-1 receptor ($NK_1R$) signaling of the formula (I):

(I)

wherein

LA is a lipid anchor that promotes insertion of the compound into a plasma membrane;

L is a linker moiety of 1 nm to 50 nm in length, wherein L is represented by the formula (IVa):

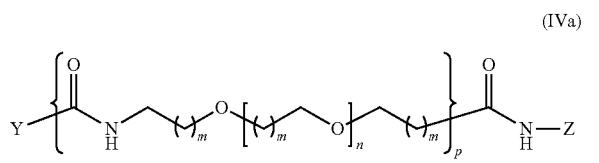

(IVa)

wherein

Z is the attachment group of the linker to the lipid anchor LA; wherein Z is defined by:

a1) $C_1$-$C_{10}$alkyl-, —$C_2$-$C_{10}$alkenyl-, —$C_2$-$C_{10}$alkynyl-, —$C_1$-$C_{10}$alkylC(O)—, —$C_2$-$C_{10}$alkenylC(O)— or —$C_2$-$C_{10}$alkynylC(O)—; or b1) together with the adjacent amine, an optionally C-terminally amidated amino acid selected from aspartic acid, glutamic acid, asparagine, glutamine, histidine, cysteine, lysine, arginine, serine or threonine; wherein the amino acid is attached to the lipid anchor via its side-chain functional group; and Y is the attachment group of the linker to the modulator X, which is a modulator of the endosomal neurokinin-1 receptor ($NK_1R$), wherein a2) Y is defined by a covalent bond, —O—, —NH—, —S—, —C(O)—, —C(O)NH—, —C(O)O—, —O—C(O)—, —NH—C(O)—, or —C(O)S—; or b2) Y when taken together with the adjacent amido group, is defined by:

a. an alpha amino acid selected from aspartic acid, glutamic acid, asparagine, glutamine, histidine, cysteine, lysine, arginine, serine or threonine; wherein the alpha amino acid is optionally attached to the modulator of the endosomal $NK_1R$ via the side-chain functional group of at least one of said alpha amino acids; or b. a beta, gamma or delta amino acid comprising a side-chain functional group which is also found in aspartic acid, glutamic acid, asparagine, glutamine, histidine, cysteine, lysine, arginine, serine or threonine; wherein said beta, gamma or delta amino acid is optionally attached to the modulator of the endosomal $NK_1R$ via at least one of said side-chain functional groups; or c. a peptide formed from alpha, beta, gamma or delta amino acids, wherein the peptide comprises at least one alpha, beta, gamma or delta amino acid which has a side-chain functional group which is also found in aspartic acid, glutamic acid, asparagine, glutamine, histidine, cysteine, lysine, arginine, serine or threonine; or combinations thereof, wherein said peptide is optionally attached to the modulator of the endosomal $NK_1R$ via at least one of said side-chain functional groups;

m is 1 or 2;

n is from 1 to 20;

p is from 1 to 8; and

X is the modulator of the endosomal neurokinin-1 receptor ($NK_1R$) defined by the structure X=M-$R^1$— as defined by formula (Va) or by formula (Vb), optionally formula (V), wherein M is covalently linked via $R^1$ to Y of the linker L:

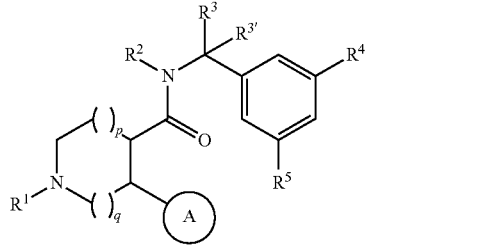

(Va)

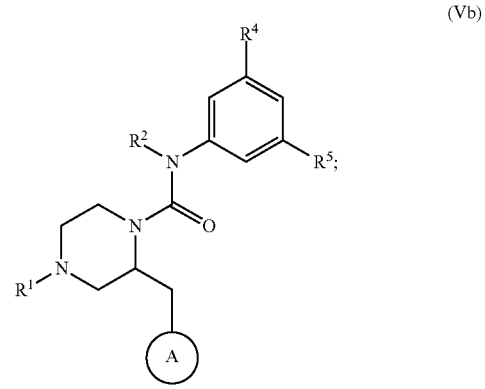

(Vb)

optionally

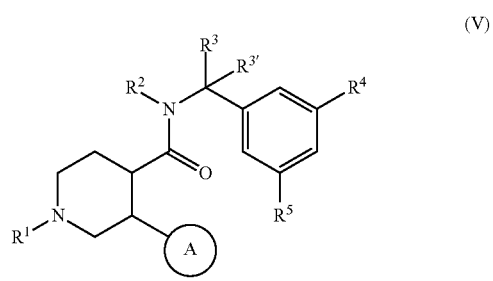

(V)

wherein:

$R^1$ is defined by —$F^1$—$R^{2'}$—$F^2$—, wherein:

M is covalently linked to $R^{2'}$ via $F^1$ (M-$F^1$—$R^{2'}$—), and $R^{2'}$ is further covalently linked to Y of the linker L via $F^2$ (M-$F^1$—$R^{2'}$—$F^2$—Y—), and $F^1$ and $F^2$ independently from each other have a covalent bond to $R^{2'}$;

$R^{2'}$ is defined by:

a3) covalent bond, b3) linear or branched $C_{1-4}$ alkyl group, optionally having, as a substituent, a 5- to 7-membered aromatic or non-aromatic heterocyclic group, which optionally further contains in addition to carbon atoms 1 to 4 heteroatoms selected from the group consisting of oxygen atom, sulfur atom and nitrogen atom, and optionally further having one or two oxo as substituents, c3) 5- to 7-membered non-aromatic heterocyclic group, optionally further containing, besides carbon atoms, 1 or 2 nitrogen atoms, and optionally having 1 to 3 substituents selected from a group consisting of oxo, linear or branched $C_{1-6}$ alkyl, phenyl, linear or branched $C_{1-6}$ alkyl-carbonyl and $C_{1-6}$ alkyl-carbonylamino, d3) linear or branched $C_{1-6}$ alkyl group, optionally having substituent(s) selected from the group consisting of:

(i) a 5- to 7-membered aromatic or non-aromatic heterocyclic group containing, besides carbon atoms, 1 to 4 nitrogen atoms, and optionally having one or two oxo as substituents, (ii) (i) a $C_{1-6}$ alkyl-carbonylamino group, (iii) a mono- or di-$C_{1-6}$ alkylamino group, and (iv) a $C_{1-6}$ alkoxy group;

e3) linear or branched $C_{1-6}$ alkoxy group, f3) $C_{3-8}$ cycloalkyl group optionally having 1 or 2 substituents selected from a group consisting of a $C_{1-6}$ alkyl-carbonylamino group, a $C_{1-6}$ alkoxy-carbonylamino group and an amino group, g3) carbamoyl group, h3) linear or branched $C_{1-6}$ alkoxy-carbonyl group, i3) $C_{1-6}$ alkyl-carbamoyl group; or combinations thereof;

$F^1$ is defined by a covalent bond or by a moiety selected from the list of functional groups consisting of:

—C(=O)—,

—C(=O)—O—,

—C(=O)—N(R$^{4'}$), and

—S(=O)$_2$—N(R$^{4'}$)—; with R$^{4'}$ being hydrogen atom or linear or branched $C_1$ to $C_{12}$ alkyl;

$F^2$ is defined by a moiety selected from the list of functional groups consisting of:

—C(=O)—,

—C(=O)—C(=O)—,

—C(=O)—(CH$_2$)$_n$—C(=O)— with n=1 to 12,

—C(=O)—(CH$_2$)$_n$— with n=1 to 12,

—C(=O)—O—(CH$_2$)$_n$—C(=O)— with n=1 to 12, and

—C(=O)—O—(CH$_2$)$_n$— with n=1 to 12;

M is defined by the following substituents:

$R^2$ is a hydrogen atom, linear or branched $C_{1-6}$ alkyl group, which optionally is halogenated;

$R^3$ and $R^{3'}$ are each independently a hydrogen atom or methyl, or $R^3$ and $R^{3'}$ are optionally bonded to each other to form a ring together with a carbon atom bonded thereto;

$R^4$ is a chlorine atom, methyl or trifluoromethyl;

$R^5$ is a chlorine atom, methyl or trifluoromethyl;

and a group represented by the formula:

is an aromatic group optionally having substituent(s);

p=0, 1 or 2;

q=1 or 2;

or a pharmaceutically acceptably salt thereof.

In another preferred embodiment of the tripartite compound, the lipid anchor partitions into lipid membranes that are insoluble in non-ionic detergent at 4° C.; or a pharmaceutically acceptable salt thereof.

In another preferred embodiment of the tripartite compound,

LA is a lipid anchor, optionally promoting insertion of the compound into a plasma membrane, represented by formula (IIaa), optionally by formula (IIa) or formula (IIIa):

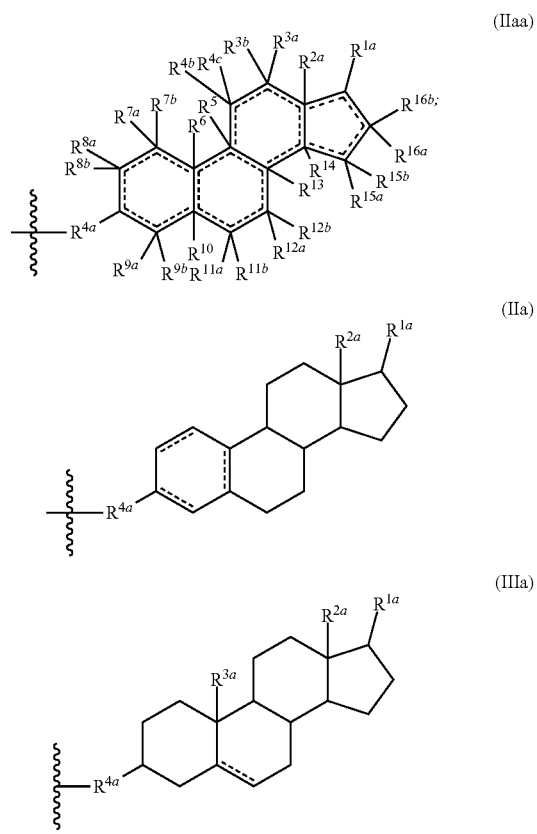

wherein $R^{1a}$ is an optionally substituted $C_{1-12}$ alkyl, alkenyl, alkynyl, alkoxy group;

$R^{2a}$, $R^{3a}$, $R^{3b}$, $R^{4b}$, $R^{4c}$, $R^5$, $R^6$, $R^{7a}$, $R^{7b}$, $R^{8a}$, $R^{8b}$, $R^{9a}$, $R^{9b}$, $R^{10}$, $R^{11a}$, $R^{11b}$, $R^{12a}$, $R^{12b}$, $R^{13}$, $R^{14}$, $R^{15a}$, $R^{15b}$, $R^{16a}$, $R^{16b}$ are independently H or $C_{1-3}$alkyl; hydroxyl, alkoxy, or amino; or, optionally, $R^{3a}R^{3b}$ and/or $R^{4b}R^{4c}$, and/or $R^{7a}R^{7b}$, and/or $R^{8a}R^{8b}$, and/or $R^{9a}R^{9b}$, and/or $R^{11a}R^{11b}$, and/or $R^{12a}R^{12b}$, and/or $R^{15a}R^{15b}$, and/or $R^{16a}R^{16b}$ are taken together to give =O (double bond to oxygen); $R^{4a}$ is CH$_2$, O, NH or S; and ===== represents a single or double bond; or a pharmaceutically acceptable salt thereof.

In another preferred embodiment of the tripartite compound, the modulator of the endosomal NK$_1$R is selected from at least one compound according to formula (VI) or formula (Vb)

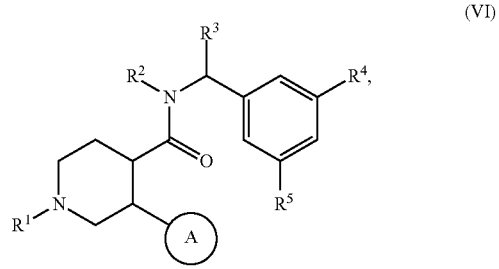

-continued

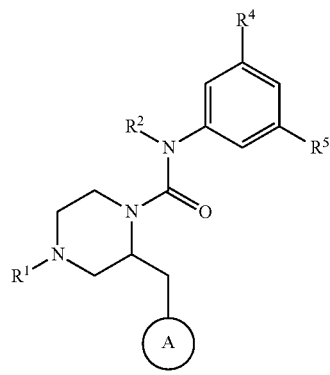

(Vb)

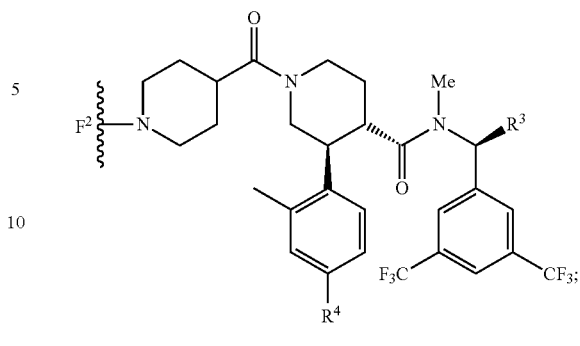

wherein R³ is hydrogen or —CH₃; R⁴ is hydrogen or fluorine; or a pharmaceutically acceptable salt thereof.

In another preferred embodiment of the tripartite compound, the moiety —R²'—F¹-M, which is covalently linked to the linker L by —F²— as shown in the following structure, is as follows:

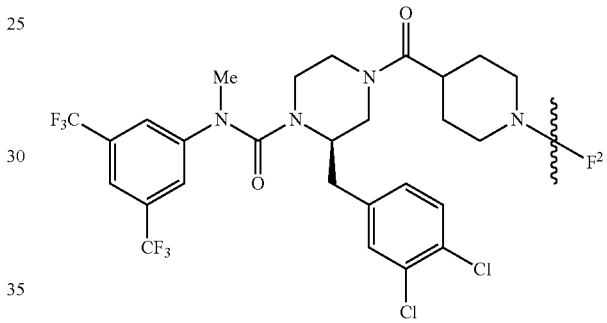

or a pharmaceutically acceptable salt thereof.

In another preferred embodiment of the tripartite compound, the moiety —F—R²'—F¹-M, which is covalently linked by Y to the linker L as shown in the following structures, is selected from the list of compounds consisting of:

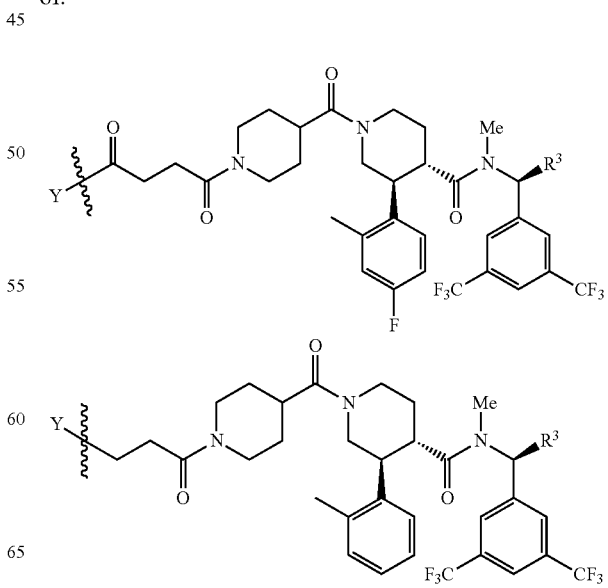

wherein
R² is methyl or cyclopropyl;
R³ is a hydrogen atom or CH₃;
R⁴ and R⁵ are trifluoromethyl; and
a group represented by

, which is a group represented by the formula:

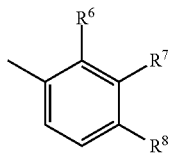

wherein
R⁶ is a hydrogen atom, methyl, ethyl or isopropyl;
R⁷ is a hydrogen atom, methyl or chlorine atom; and
R⁸ is a hydrogen atom, a fluorine atom, a chlorine atom or methyl; or
3-methylthiophen-2-yl; or a pharmaceutically acceptable salt thereof.

In another preferred embodiment of the tripartite compound, the partial structure:

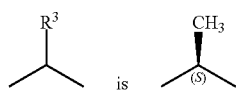

or R³ is hydrogen atom, and R³' is hydrogen atom; or a pharmaceutically acceptable salt thereof.

In another preferred embodiment of the tripartite compound, the moiety —R²—F¹-M, which is covalently linked to the linker L by —F²— as shown in the following structure, is as follows:

-continued

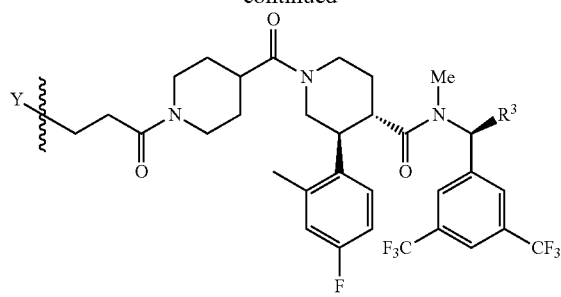

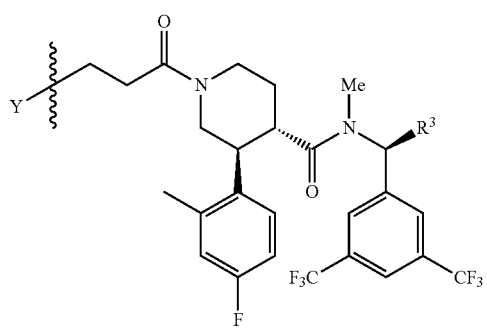

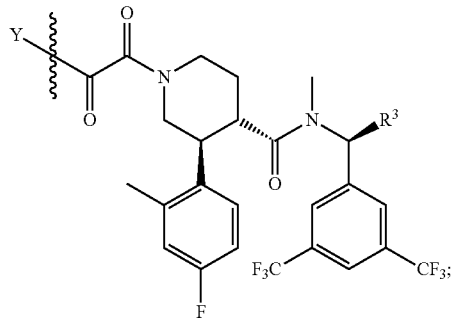

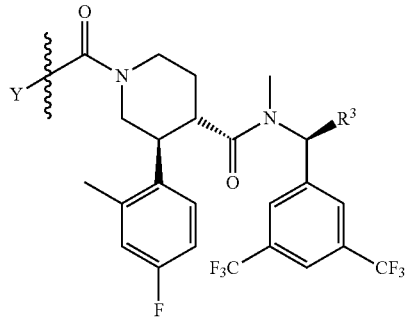

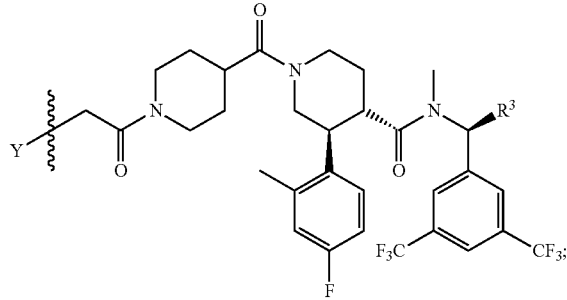

and combinations thereof, wherein $R^3$ is hydrogen atom or $CH_3$; $R^4$ is hydrogen or fluorine or pharmaceutically acceptable salts thereof.

In another preferred embodiment of the tripartite compound, the moiety —$F^2$—$R^{2'}$—$F^1$-M, which is covalently linked by Y to the linker L as shown in the following structures, is selected from the list of compounds consisting of:

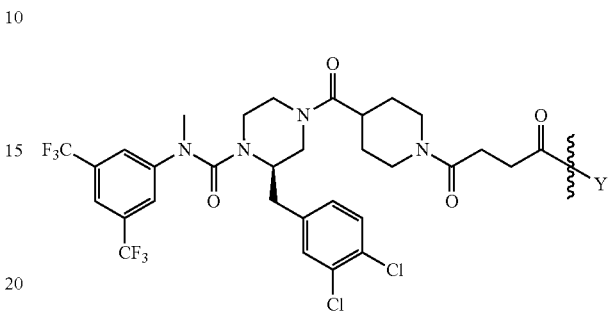

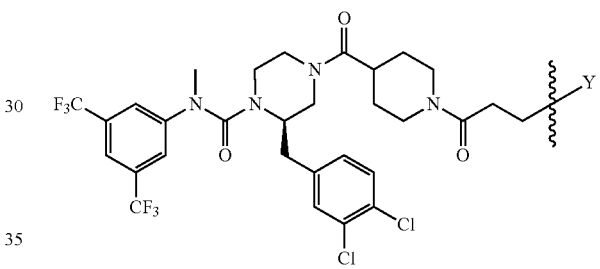

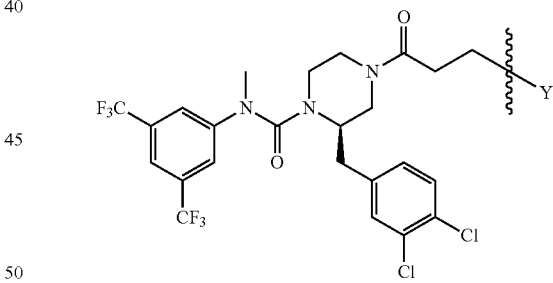

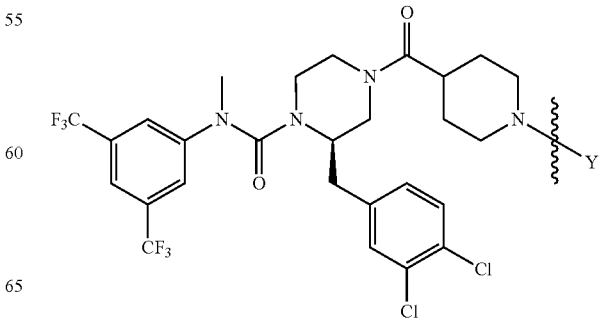

11
-continued
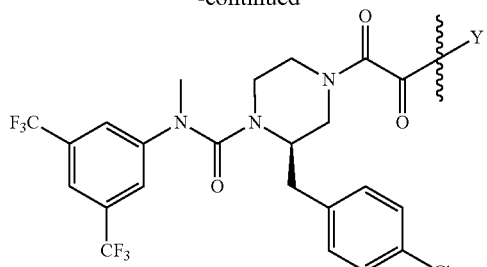
12
-continued
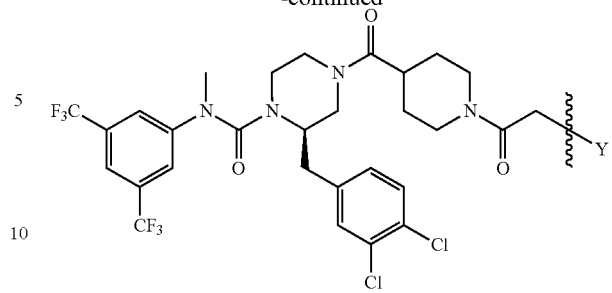
and combinations thereof; or pharmaceutically acceptable salts thereof.
In another preferred embodiment of the tripartite compound, the compound is selected from the list of compounds consisting of the following structures:
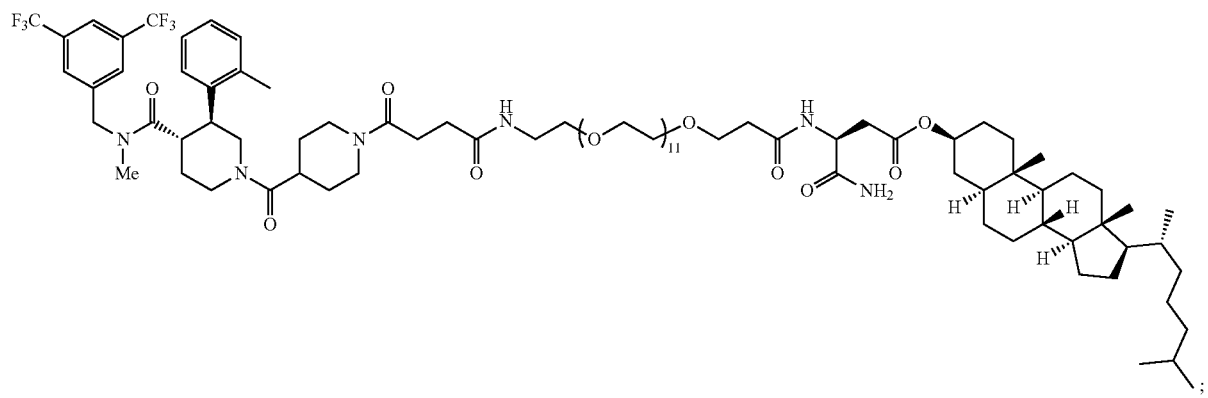
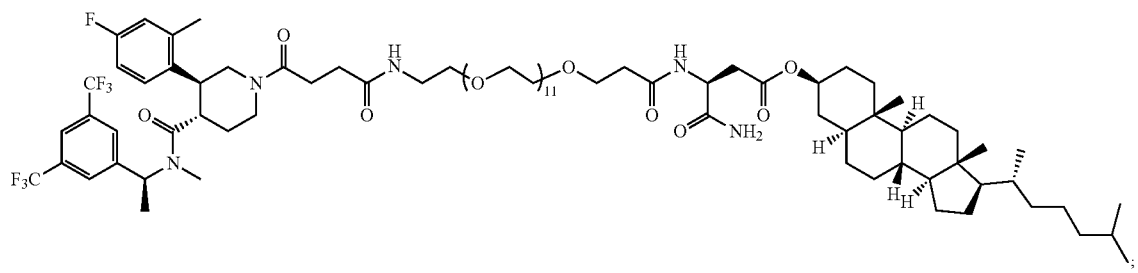

-continued
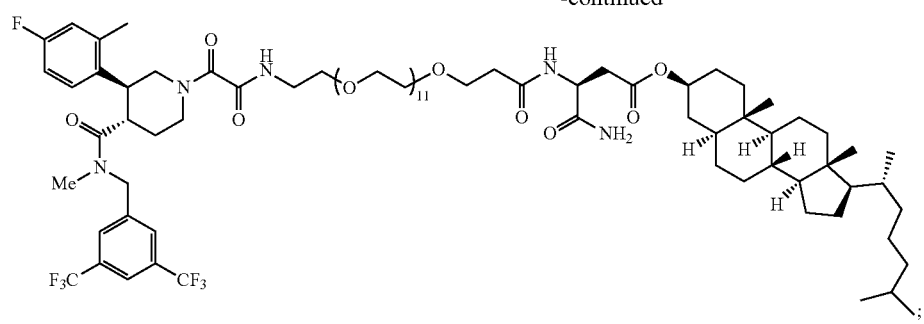
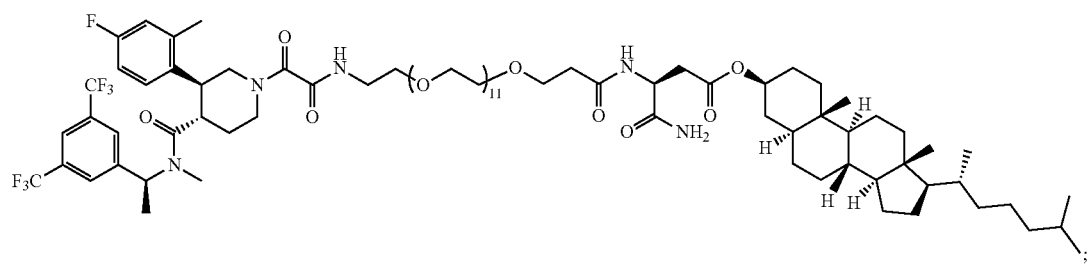
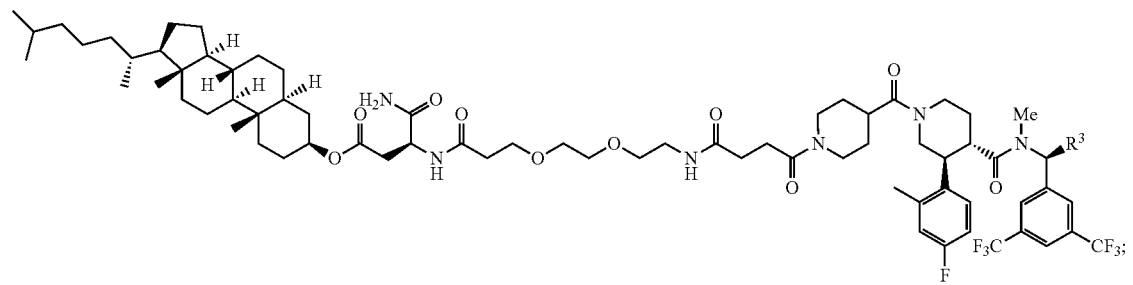
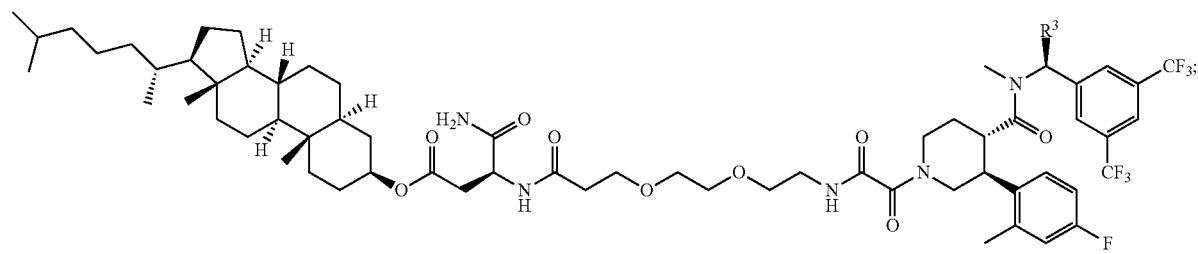

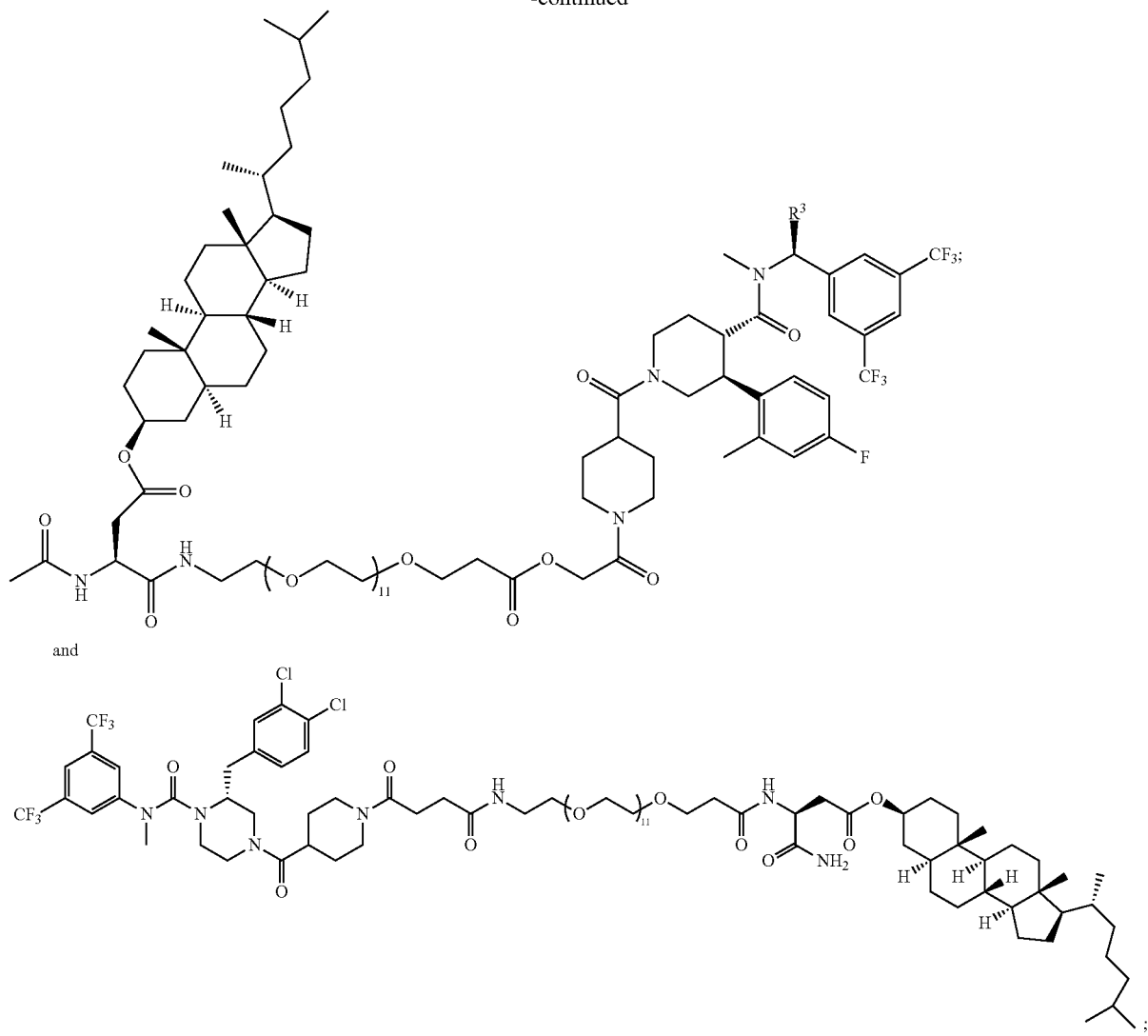

and wherein R³ is hydrogen atom or —CH₃; or a pharmaceutically acceptable salt thereof.

In another aspect of the invention, a prodrug of the tripartite compound is provided.

In another aspect of the invention, a pharmaceutical composition comprising the tripartite compound, or a prodrug thereof, is provided.

In another preferred embodiment, the pharmaceutical composition is for use as a tachykinin receptor antagonist.

In another preferred embodiment, the pharmaceutical composition is provided for the treatment of a disease or disorder mediated by endosomal NK₁R signalling.

In another preferred embodiment, the pharmaceutical composition is provided for use in the prophylaxis or treatment of a lower urinary tract disease, a gastrointestinal disease or a central nervous system disease.

In another preferred embodiment, the pharmaceutical composition is provided for the prophylaxis or treatment of overactive bladder, irritable bowel syndrome, inflammatory bowel disease, vomiting, nausea, depression, anxiety neurosis, anxiety, generalised anxiety disorder (GAD), pelvic visceral pain or interstitial cystitis.

In another preferred embodiment, the pharmaceutical composition is provided for treatment of a disease or disorder mediated by endosomal NK₁R signaling selected from the list of chemotherapy-induced nausea and vomiting (CINV), cyclic vomiting syndrome, postoperative nausea and vomiting, affective and addictive disorders including depression and anxiety, generalised anxiety disorder (GAD), gastrointestinal disorders including inflammatory bowel disease, irritable bowel syndrome, gastroparesis and functional dyspepsia, chronic inflammatory disorders including arthritis, respiratory disorders including COPD and asthma, urogenital disorders, sensory disorders and pain including somatic pain and visceral pain, pruritus, viral and bacterial infections and proliferative disorders (cancer), and combinations thereof.

In another preferred embodiment, the disease or disorder mediated by endosomal NK₁R signaling is somatic pain or visceral pain.

In another preferred embodiment, the disease or disorder mediated by endosomal NK₁R signaling is a chronic disease or disorder.

In another aspect of the invention, the tripartite compound is used in the treatment of a disease or disorder mediated by endosomal NK₁R signalling.

In another aspect of the invention, a pharmaceutical composition is provided, wherein the pharmaceutical composition comprises a therapeutically effective amount of a tripartite compound, or pharmaceutically acceptable salts thereof, together with at least one pharmaceutically acceptable carrier or diluent.

In another aspect of the invention, a tripartite compound for targeting endosomal GPCR signaling of the following formula is provided:

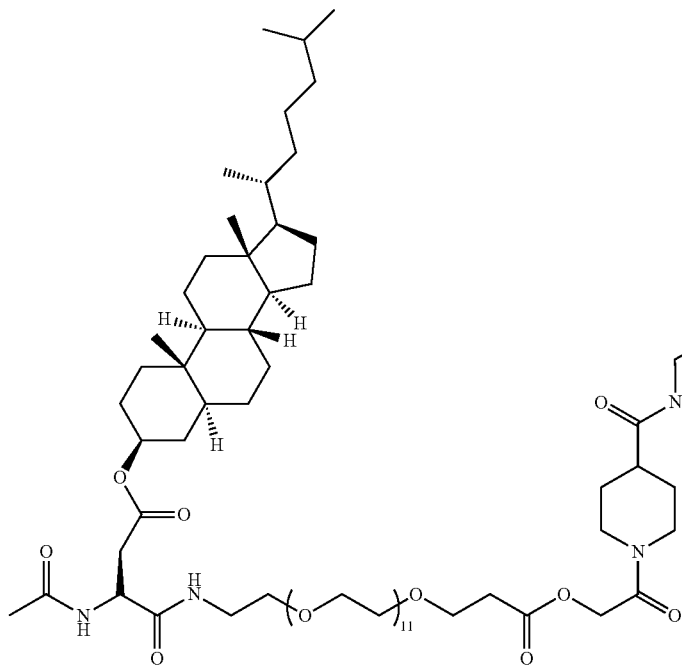

In another aspect the present invention provides a tripartite compound for targeting endosomal GPCR signaling of the formula (Ie):

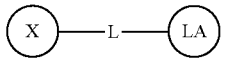

(Ie)

wherein

LA is a lipid anchor that promotes insertion of the compound into a plasma membrane;

L is a linker moiety of 1 nm to 50 nm in length; and

X is a modulator of an endosomal GPCR;

wherein, the lipid anchor partitions into lipid membranes that are insoluble in non-ionic detergent at 4° C.; or pharmaceutically acceptable salts thereof.

In another aspect, the present invention provides a tripartite compound for targeting endosomal GPCR signaling of the formula (Ia):

X—L—LA (Ia)

wherein

LA is a lipid anchor that promotes insertion of the compound into a plasma membrane represented by formulae (IIa) or (IIIa):

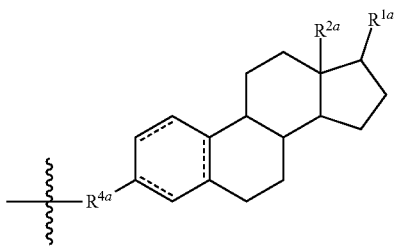

(IIa)

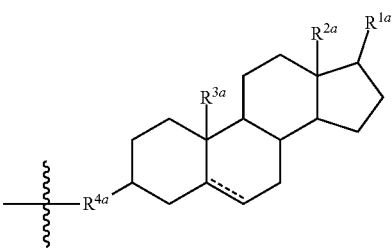

(IIIa)

wherein $R^{1a}$ is an optionally substituted $C_{1-12}$ alkyl group;

$R^{2a}$ and $R^{3a}$ are independently H or $C_{1-3}$alkyl;

$R^{4a}$ is C, O, NH or S;

------ represents a single or double bond;

L is a linker group of 1 nm to 50 nm in length; and

X is a modulator of an endosomal GPCR; or pharmaceutically acceptable salts thereof.

In another aspect, the present invention provides a tripartite compound for targeting endosomal GPCR signaling of the formula (Ib):

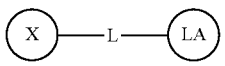

(Ib)

wherein

LA is a lipid anchor that promotes insertion of the compound into a plasma membrane represented by formulae (IIa) or (IIIa):

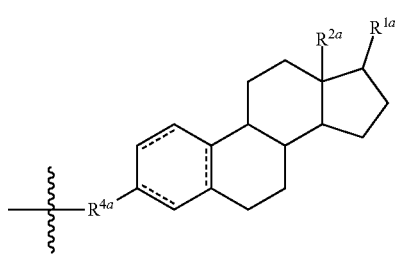

(IIa)

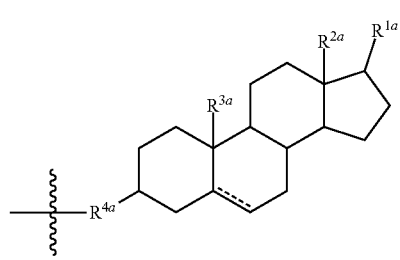

(IIIa)

wherein $R^{1a}$ is an optionally substituted $C_{1-12}$ alkyl group;

$R^{2a}$ and $R^{3a}$ are independently H or $C_{1-3}$alkyl;

$R^{4a}$ is C, O, NH or S;

------ represents a single or double bond;

L is represented by the formula (IVa):

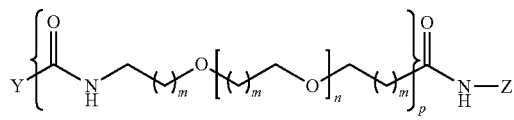

(IVa)

wherein

Z is the attachment group between the linker and the lipid anchor and is —$C_1$-$C_{10}$alkyl-, —$C_2$-$C_{10}$alkenyl-, —$C_2$-$C_{10}$alkynyl-, —$C_1$-$C_{10}$alkylC(O)—, —$C_2$-$C_{10}$alkenylC(O)— or —$C_2$-$C_{10}$alkynylC(O)—; or Z, together with the adjacent amine, is an optionally C-terminal amidated amino acid selected from aspartic acid, glutamic acid, asparagine, glutamine, histidine, cysteine, lysine, arginine, serine or threonine; wherein the amino acid is attached to the lipid anchor via its side-chain functional group;

Y is the attachment group between the linker and the modulator of an endosomal GPCR and is —O—, —NH—, —S—, —C(O)—, —C(O)NH—, —C(O)O— or —C(O)S—; or Y, together with the adjacent amido group, is an amino acid selected from aspartic acid, glutamic acid, asparagine, glutamine, histidine, cysteine, lysine, arginine, serine or threonine; wherein the amino acid is attached to the modulator of an endosomal GPCR via its side-chain functional group;

m is 1 or 2;

n is from 1 to 20;

p is from 1 to 8; and

X is a modulator of an endosomal GPCR; or pharmaceutically acceptable salts thereof.

In another aspect the present invention provides a method of modulating endosomal GPCR signaling comprising contacting an endosomal GCPR with a tripartite compound of formula (Ie) as herein defined.

In another aspect the present invention provides a method of modulating endosomal GPCR signaling in a subject in need thereof comprising administering to the subject an effective amount of a tripartite compound of formula (Ie) as herein defined.

In another aspect the present invention provides a method for the treatment of a disease or disorder mediated by endosomal substance P (SP) or neurokinin 1 receptor ($NK_1R$) signaling comprising administering to a subject in need thereof an effective amount of a tripartite compound of formula (Ie) as herein defined.

In a further aspect the present invention provides a method for the treatment of a disease or disorder mediated by endosomal CGRP signaling comprising administering to a subject in need thereof an effective amount of a compound of formula (Ie) as herein defined.

These and other aspects of the present invention will become more apparent to the skilled addressee upon reading the following detailed description in connection with the accompanying examples and claims.

DETAILED DESCRIPTION OF THE INVENTION

Figure 1:
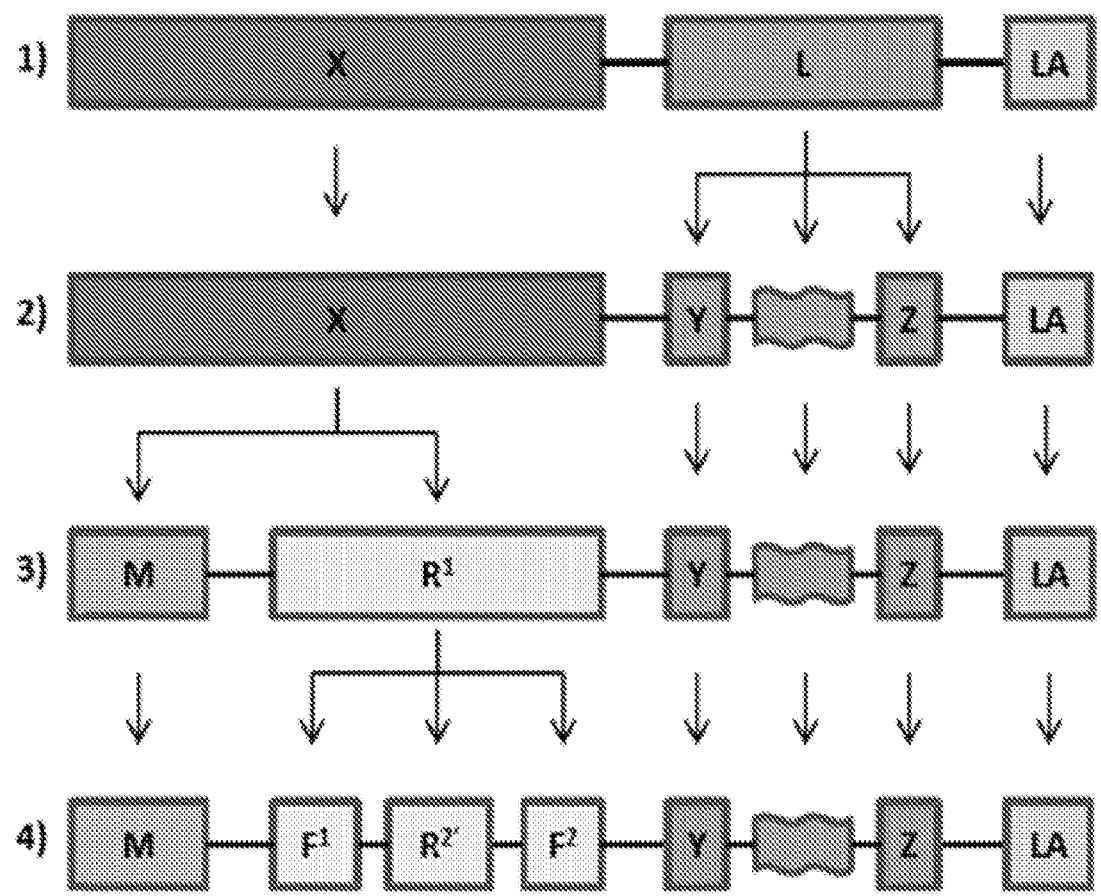
FIG. 1: Schematic representation of the tripartite compound of the present invention illustrating its different moieties and the linkage pattern between the moieties.

By studying the substance P (SP) neurokinin 1 receptor (NK$_1$R) as a prototypical GPCR that robustly traffics to endosomes upon activation, it has now been shown that endosomal GPCRs convey sustained signals that underlie excitation and nociceptive transmission in spinal neurons. These findings suggest that targeting GPCRs in endosomes is required for optimal pharmacological intervention. The concept that endosomes are platforms for compartmentalized GPCR signaling that underlies pathophysiologically important processes has implications for receptor signal-specificity and therapeutic targeting. Endosomal trafficking allows GPCRs to generate signals in subcellular compartments that may explain how different receptors that activate the same G-proteins and βarrs can specifically regulate responses. Delivery of GPCR modulators to endosomes may enable targeting of signals that underlie disease-relevant processes with enhanced efficacy and selectivity.

It has previously been suggested that targeting GPCR endothelin type B ($ET_BR$) localised in caveolae may provide an effective anti-tumour therapy (see WO2005/097199). The $ET_BR$ has been shown to mediate diverse physiological effects on vasoconstriction, cellular development, differentiation and mitogenesis (Yamaguch, T. et al. Eur. J. Biochem 2003, 270, 1816-1827). Distinct from endosomes, caveolae are small flask-shaped or cup-shaped pits formed in the cell membrane and unlike endosomes, caveolae are not coated with clathrin.

It has now been discovered for the first time that targeting endosomal GPCRs provides a novel method for the treatment and prevention of diseases and disorders mediated by endosomal GPCR signaling.

In one embodiment, a tripartite compound is provided according to formula (I) for modulating endosomal GPCR signaling.

In another embodiment, the present invention provides a method of modulating endosomal GPCR signaling comprising administering to a subject in need thereof an effective amount of a compound of formula (Ie) as herein defined.

The term "tripartite compound" as herein used refers to compounds comprising an endosomal GPCR modulator covalently bound to a linker group, the linker group being covalently bound to a lipid anchor capable of anchoring the compound of formula (I) or (Ie) to the lipid bilayer of a cell membrane and ultimately, to the membrane of an early endosome.

The term "lipid anchor" (LA) as herein used denotes moieties that are capable of partitioning into lipid membranes and thereby anchoring the compound of formula (I) into the lipid membrane. The partition into the lipid membrane may occur directly from the extracellular or vesicular luminal space or may occur laterally from the lipid bilayer.

In one preferred embodiment, the lipid anchor may be characterized by its ability to partition into lipid membranes whereby said lipid membranes are characterized by insolubility in non-ionic detergents at 4° C.

Examples of suitable lipid anchors include, but are not limited to cholesterol, cholestanol, sphingolipid, GPI-anchor or saturated fatty acid derivatives. Many such lipid anchors have been described in the art, for example, in WO2005/097199, the entirety of which is incorporated herein by reference.

In one embodiment the lipid anchor is a moiety selected from formulae (IIa) or (IIIa):

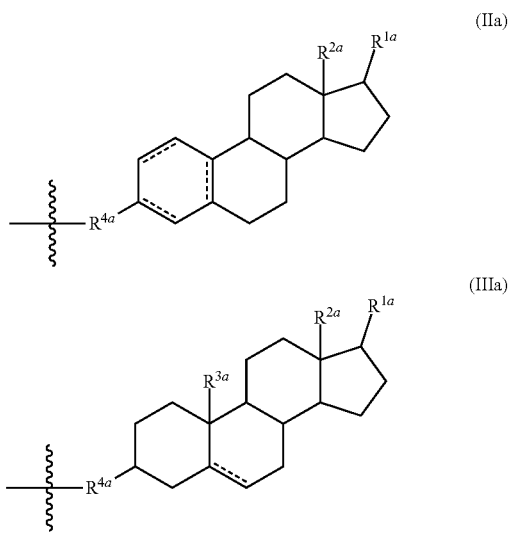

wherein
$R^{1a}$ is an optionally substituted $C_{1-12}$ alkyl group;
$R^{2a}$ and $R^{3a}$ are independently H or $C_{1-3}$alkyl;
$R^{4a}$ is —$CH_2$—, —O—, —NH—, —S—, —NH($CH_2$)$_a$OPO$_3$—, —NH($CH_2$)$_a$SO$_2$CF$_2$—, —NH($CH_2$)$_a$SO$_2$NH—, —NHCONH—, —NHC(O)O—, —NHCH(CONH$_2$)(CH$_2$)$_b$C(O)O—, —NHCH(COOH)(CH$_2$)$_b$C(O)O—, —NHCH(CONH$_2$)(CH$_2$)$_b$CONH—, —NHCH(COOH)(CH$_2$)$_b$CONH—, —NHCH(CONH$_2$)(CH$_2$)$_4$NH((CO)CH$_2$O)$_e$— or —NHCH(COOH)(CH$_2$)$_4$NH((CO)CH$_2$O)$_e$—;
a is an integer from 2 to 3;
b is an integer from 1 to 2;
e is an integer from 0 to 1; and
===== represents a single or double bond.

In other embodiments the lipid anchor is a moiety selected from formulae (VIa), (VIIa), (VIIIa) or (IXa):

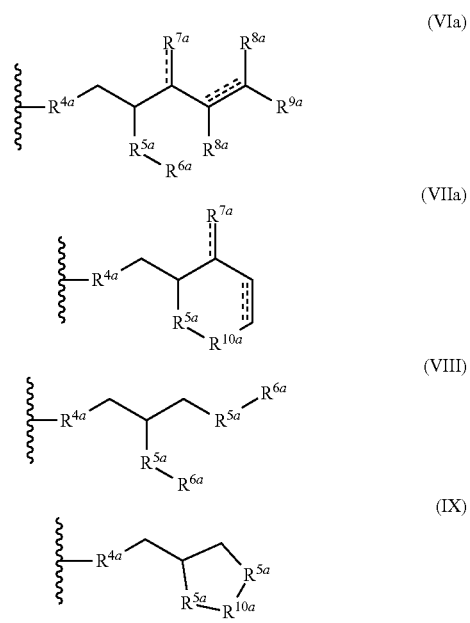

wherein $R^{4a}$ is as described above;

----- represents a single or double bond;

===== represents a single, double or triple bond;

each occurrence of $R^{5a}$ is independently —NH—, —O—, —S—, —OC(O)—, —NHC(O)—, —NHCONH—, —NHC(O)O— or —NHS(O$_2$)—;

each occurrence of $R^{6a}$ is independently a $C_{14\text{-}30}$ alkyl group optionally substituted by fluorine, optionally 1 to 4 fluorine atoms;

each occurrence of $R^{7a}$ is independently NH$_2$, NHCH$_3$, OH, H, halogen or O, provided that when $R^{7a}$ is NH$_2$, NHCH$_3$, OH, H or halogen then ----- is a single bond and when $R^{7a}$ is O then ===== is a double bond;

each occurrence of $R^{8a}$ is independently H, OH or is absent when ===== represents a triple bond;

$R^{9a}$ is a $C_{10\text{-}30}$ alkyl group optionally substituted by fluorine, optionally 1 to 4 fluorine atoms; and each occurrence of $R^{10a}$ is independently a $C_{24\text{-}40}$ alkylene group, a $C_{24\text{-}40}$ alkenylene group or a $C_{24\text{-}40}$ alkynylene group optionally substituted by fluorine, optionally 1 to 4 fluorine atoms.

In further embodiments, the lipid anchor is a moiety selected from formulae (Xa) or (XIa):

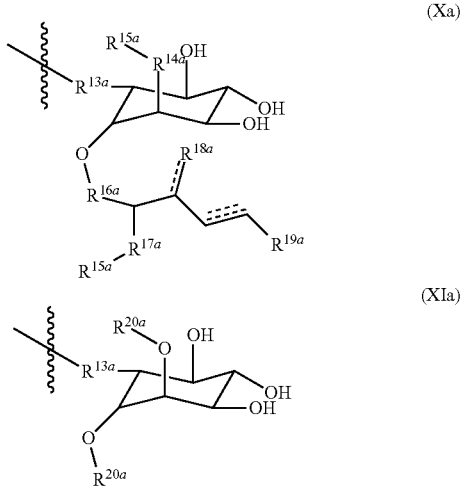

(Xa)

(XIa)

wherein

----- represents a single or double bond;

===== represents a single, double or triple bond;

each occurrence of $R^{13a}$ is independently —O— or —CO(CH$_2$)$_a$(CO)$_b$O—, wherein a is an integer from 1 to 3 and b is an integer from 0 to 1;

$R^{14a}$ is —O— or —OC(O)—;

each occurrence of $R^{15a}$ is independently selected from a $C_{16\text{-}30}$ alkyl group optionally substituted with fluorine, optionally 1 to 4 fluorine atoms;

$R^{16a}$ is —PO$_3$—CH$_2$—, —SO$_3$CH$_2$—, —CH$_2$—, —CO$_2$CH$_2$— or a direct bond;

$R^{17a}$ is —NH—, —O—, —S—, —OC(O)—, —NHC(O)—, —NHCONH—, —NHC(O)O— or —NHS(O$_2$)—;

$R^{18a}$ is NH$_2$, NHCH$_3$, OH, H, halogen or O;

$R^{19a}$ is a $C_{16\text{-}30}$ alkyl group optionally substituted with fluorine, optionally 1 to 4 fluorine atoms; and each $R^{20a}$ is a C(O)C$_{13\text{-}25}$alkyl group optionally substituted with a group of the following formulae:

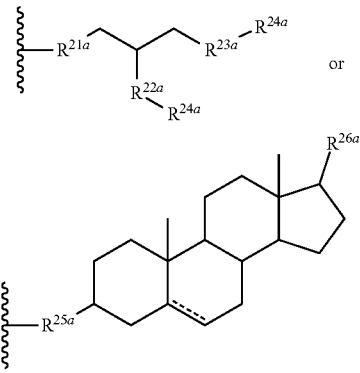

or wherein

----- is a single or double bond;

$R^{21a}$ is —PO$_3$—CH$_2$—, —SO$_3$CH$_2$—, —CH$_2$—, —CO$_2$CH$_2$— or a direct bond;

$R^{22a}$ is —NH—, —O—, —S—, —OC(O)—, —NHC(O)—, —NHCONH—, —NHC(O)O— or —NHS(O$_2$)—;

$R^{23a}$ is —O— or —OC(O)—;

each occurrence of $R^{24a}$ is independently selected from a $C_{16\text{-}30}$ alkyl group optionally substituted with fluorine, optionally 1 to 4 fluorine atoms;

$R^{25a}$ is —CO(CH$_2$)$_a$(CO)$_b$O— or —CO(CH$_2$)$_a$(CO)$_b$NH—, wherein a is an integer from 1 to 3 and b is an integer from 0 to 1; and $R^{26a}$ is a $C_{4\text{-}20}$ alkyl group optionally substituted with fluorine, optionally 1 to 4 fluorine atoms.

In further embodiments the lipid anchor is a moiety selected from formulae (XIIa), (XIIIa), (XIVa) or (XVa):

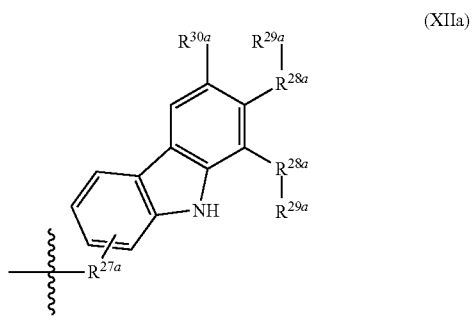

(XIIa)

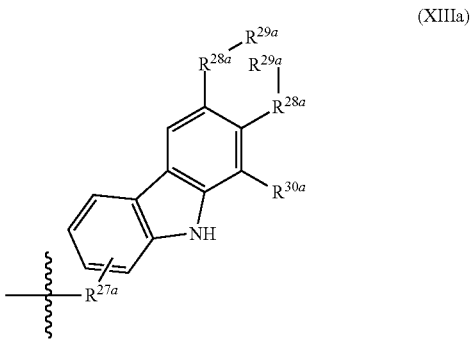

(XIIIa)

-continued (XIVa)

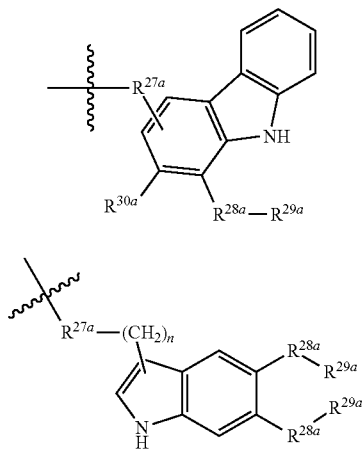

(XVa)

wherein each occurrence of $R^{27a}$ is independently selected from —NH—, —O—, —NH(CH$_2$)$_c$OPO$_3$—, —NH(CH$_2$)$_c$SO$_2$NH—, —NHCONH—, —NHC(O)O—, —CO(CH$_2$)$_b$(CO)$_a$NH—, —CO(CH$_2$)$_b$(CO)$_a$O—, —CO(CH$_2$)$_b$S—, —CO(CH$_2$)$_b$OPO$_3$—, —CO(CH$_2$)$_b$SO$_2$NH—, —CO(CH$_2$)$_b$NHCONH—, —CO(CH$_2$)$_b$OCONH—, —CO(CH$_2$)$_b$OSO$_3$—, or —CO(CH$_2$)$_b$NHC(O)O—, wherein a is an integer from 0 to 1, b is an integer from 1 to 3 and c is an integer from 2 to 3;

each occurrence of $R^{28a}$ is independently —CH$_2$— or —O—;

each occurrence of $R^{29a}$ is independently selected from H or a $C_{16-30}$ alkyl group optionally substituted by fluorine, optionally 1 to 4 fluorine atoms;

each occurrence of $R^{31a}$ is independently selected from H, or a $C_{1-15}$ alkyl group, optionally substituted by fluorine, optionally 1 to 4 fluorine atoms, or a $C_{1-15}$ alkoxy group optionally substituted by fluorine, optionally 1 to 4 fluorine atoms; and n is an integer from 1 to 2.

The term "linker" as herein used relates to the part of the compound that links the modulator of an endosomal GPCR to the lipid anchor. It will be understood that the linker should be selected such that it does not compete with the modulator of an endosomal GPCR at the ligand binding site. Nor should the linker partition into the lipid membrane.

The linker group should optionally be of a length of between 1 nm to 50 nm in order to allow the modulator of an endosomal GPCR to interact with the receptor when the lipid anchor is anchored in the endosome membrane.

In one embodiment, the linker group will comprise one or more polyethelene glycol units. In another embodiment it is envisaged that the linker, or subunits of the linker, may be amino acid residues, derivatised or functionalised amino acid residues, polyethers, ureas, carbamates, sulphonamides or other subunits that provide adequate distance between the modulator of an endosomal GPCR and the lipid anchor without interfering in the function of either group.

In one embodiment, the linker is represented by a moiety of the formula (IVa):

(IVa)

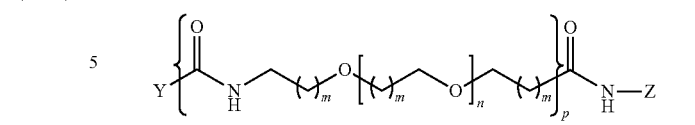

wherein

Z is the attachment group of the linker to the lipid anchor and is —C$_1$-C$_{10}$alkyl-, —C$_2$-C$_{10}$alkenyl-, —C$_2$-C$_{10}$alkynyl-, —C$_1$-C$_{10}$alkylC(O)—, —C$_2$-C$_{10}$alkenylC(O)— or —C$_2$-C$_{10}$alkynylC(O)—; or Z, together with the adjacent amine, is an optionally C-terminal amidated amino acid selected from aspartic acid, glutamic acid, asparagine, glutamine, histidine, cysteine, lysine, arginine, serine or threonine; wherein the amino acid is attached to the lipid anchor via its side-chain functional group;

Y is the attachment group between the linker and the modulator of an endosomal GPCR and is —O—, —NH—, —S—, —C(O)—, —C(O)NH—, —C(O)O— or —C(O)S—; or Y, together with the adjacent amido group is an amino acid selected from aspartic acid, glutamic acid, asparagine, glutamine, histidine, cysteine, lysine, arginine, serine or threonine; wherein the amino acid is attached to the modulator of an endosomal GPCR via its side-chain functional group;

or

Y is the attachment group of the linker to the modulator X, which is a modulator of the endosomal neurokinin-1 receptor (NK$_1$R), wherein a2) Y is defined by —O—, —NH—, —S—, —C(O)—, —C(O)NH—, —C(O)O—, —O—C(O)—, —NH—C(O)—, or —C(O)S—; or b2) Y when taken together with the adjacent amido group, is defined by:
 a. an alpha amino acid selected from aspartic acid, glutamic acid, asparagine, glutamine, histidine, cysteine, lysine, arginine, serine or threonine; wherein the alpha amino acid is optionally attached to the modulator of the endosomal NK$_1$R via the side-chain functional group of at least one of said alpha amino acids; or
 b. a beta, gamma or delta amino acid comprising a side-chain functional group which is also found in aspartic acid, glutamic acid, asparagine, glutamine, histidine, cysteine, lysine, arginine, serine or threonine; wherein said beta, gamma or delta amino acid is optionally attached to the modulator of the endosomal NK$_1$R via at least one of said side-chain functional groups; or
 c. a peptide formed from alpha, beta, gamma or delta amino acids, wherein the peptide comprises at least one alpha, beta, gamma or delta amino acid which has a side-chain functional group which is also found in aspartic acid, glutamic acid, asparagine, glutamine, histidine, cysteine, lysine, arginine, serine or threonine; or combinations thereof, wherein said peptide is optionally attached to the modulator of the endosomal NK$_1$R via at least one of said side-chain functional groups;

m is 1 or 2;
n is from 1 to 20; and
p is from 1 to 8.

In another embodiment, the linker is represented by a moiety of the formula (XXa):

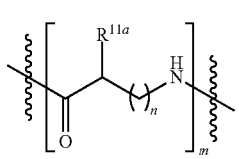

(XXa)

wherein
each occurrence of $R^{11a}$ is independently any side chain of a naturally occurring, derivatised or functionalised amino acid residue;
m is an integer from 3 to 80; and
n is an integer from 0 to 1.

In other embodiments, the linker is represented by a moiety of the formula (XXIa):

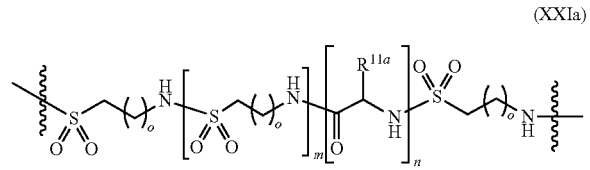

(XXIa)

wherein
m is an integer from 0 to 40;
n is an integer from 0 to 1;
each occurrence of o is independently an integer from 1 to 5;
each occurrence of $R^{11a}$ is independently any side chain of a naturally occurring, derivatised or functionalised amino acid residue; and
wherein the $SO_2$ terminus is bound to the lipid anchor and the N-terminus is bound to the modulator of an endosomal GPCR.

In another embodiment, the linker is represented by a moiety of the formula (XXIIa):

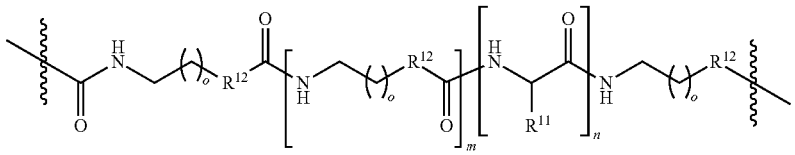

(XXIIa)

wherein
m is an integer from 0 to 40;
n is an integer from 0 to 1;
each occurrence of o is independently an integer from 1 to 5;
each $R^{12a}$ is independently NH or 0;
each occurrence of $R^{11a}$ is independently any side chain of a naturally occurring, derivatised or functionalised amino acid residue; and
wherein the C(O)-terminus is bound to the lipid anchor and the $R^{12a}$-terminus is bound to the modulator of an endosomal GPCR.

A number of suitable linker moieties have been described in WO2005/097199, the entirety of which is incorporated herein by reference.

The term "modulator of an endosomal GPCR" as herein used refers to agonists and antagonists or inhibitors of G protein-coupled receptors that are endocytosed into endosomes.

In one embodiment the GPCR modulator will be an agonist of the receptor. In another embodiment, the GPCR modulator will be an antagonist or inhibitor of the receptor.

The GPCR modulator may be in any form including, but not limited to, an organic molecule, a polypeptide sequence, a hormone, a protein fragment or a derivative of any of these.

In particular, the GPCR modulator optionally is an organic molecule, or, alternatively or additionally, a hormone, or a derivative of these.

The term "endosomal GPCR signaling" as herein used refers to the signal transduced by an activated G protein-coupled receptor that has been endocytosed into an endosome, optionally an early endosome.

In one embodiment endosomal GPCR signaling will be signaling that is first transduced at the plasma membrane and is maintained when the receptor is endocytosed into early endosomes.

In another embodiment, the endosomal GPCR signaling will be signaling that requires receptor endocytosis and/or occurs exclusively on endosomal membranes, for example, β-arrestin mediated signaling. It is believed that βarrs interact with agonist-occupied, G protein-coupled receptor kinase (GRK)-phosphorylated GPCRs at the cell surface and promote the transfer of ligand-bound receptor from the cell surface to early endosomes via dynamin- and clathrin-dependent endocytosis. It has recently been discovered that this pathway can mediate a second series of endosomal GPCR signaling that is distinct from G protein-dependent signaling at the plasma membrane. It is believed that the importance of this mechanism depends on the affinity with which GPCRs interact with βarrs, which varies depending on the extent of GPCR phosphorylation by GRKs. "Class A" GPCRs (e.g., $β_2AR$, $α_{1b}AR$) have few phosphorylation sites, and transiently interact with βarr1 and βarr2, mostly at the plasma membrane, with a higher affinity for βarr2. "Class B" GPCRs (e.g., $AT_{1A}R$, $NK_1R$) are phosphorylated at multiple sites and interact with both βarr1 and 2 with high affinity for prolonged periods at plasma and endosomal membranes. "Class C" GPCRs (e.g., bradykinin $B_2$ receptor) internalize with βarrs into endosomes followed by rapid dissociation of βarr upon agonist removal.

It is believed that the extent of βarr-induced MAPK signaling depends on the affinity of the receptor for βarrs, which depends on the receptor structure and on which of the seven mammalian GRKs phosphorylate the receptor. Thus, activation of $AT_{1A}R$ and $V_2R$ causes greater phosphorylation of βarr-bound ERK1/2 than activation of $α_{1b}AR$ and $β_2AR$, suggesting that the class B receptors signal more robustly through this pathway. Class B GPCRs include the secretin receptor, $VPAC_1$ receptor, $VPAC_2$ receptor, $PAC_1$ receptor, glucagon receptor, growth hormone releasing hormone (GHRH) receptor, glucagon-related peptide 1 (GLP-1) receptor, glucagon-related peptide 2 (GLP-2) receptor, gastric inhibitory polypeptide (GIP) receptor, corticotropin releasing factor 1 (CRF1) receptor, corticotropin releasing factor 2 (CRF2) receptor, parathyroid hormone 1 (PTH1) receptor, parathyroid hormone 2 (PTH2) receptor, calcitonin receptor-like receptor, calcitonin receptor, angiotensin II receptor type 1, vasopressin receptor 2, calcitonin gene related peptide (CGRP) receptor, neurokinin 1 receptor (NK$_1$R), and protease activated-2 receptor (PAR$_2$).

In some preferred embodiments of the invention, and with reference to the general formula (I) or (Ie), one or more of the following embodiments apply:

a) LA is a lipid anchor selected from cholesterol, cholestanol, sphingolipid, a GPI-anchor or a saturated fatty acid derivative.

b) LA is a lipid anchor selected from moieties of formulae (IIa), (IIIa), (VIIa), (VIIIa), (IXa), (Xa), (XIa), (XIIa), (XIIIa) and (IXa).

c) LA is a lipid anchor selected from moieties of formulae (IIa) or (IIIa).

d) L is a linker moiety comprising one or more subunits, the subunits comprising polyethelene glycol units, amino acid residues, derivatised or functionalised amino acid residues, polyethers, ureas, carbamates and/or sulphonamides.

e) L is a linker moiety represented by formulae (IVa), (XXa), (XXIa) or (XXIIa).

f) L is a linker moiety represented by formula (IVa).

g) X is an agonist of an endosomal GPCR, optionally of endosomal neurokinin-1 receptor.

h) X is an antagonist of an endosomal GPCR, optionally of endosomal neurokinin-1 receptor.

In a preferred embodiment LA is a lipid anchor represented by formulae (IIa) or (IIIa).

Accordingly, in one embodiment, the present invention provides tripartite compounds of the formula (I) represented by formula (Ia):

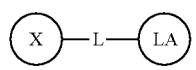

(Ia)

wherein

LA is a lipid anchor that promotes insertion of the compound into a plasma membrane represented by formulae (IIa) or (IIIa):

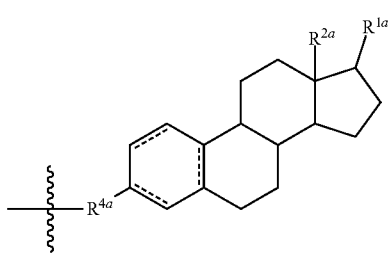

(IIa)

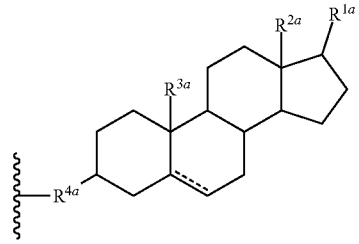

(IIIa)

wherein
R$^{1a}$ is an optionally substituted C$_{1-12}$ alkyl group;
R$^{2a}$ and R$^{3a}$ are independently H or C$_{1-3}$alkyl;
R$^{4a}$ is C, O, NH or S; and
===== represents a single or double bond;
L is a linker group of 1 nm to 50 nm in length; and
X is a modulator of an endosomal GPCR, optionally endosomal neurokinin-1 receptor; or pharmaceutically acceptable salts thereof.

In another preferred embodiment, LA is a lipid anchor represented by formulae (IIa) or (IIIa) and L is a linker represented by formula (IVa).

Accordingly, in another embodiment, the present invention provides tripartite compounds of the formula (I) represented by formula (Ib):

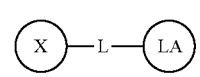

(Ib)

wherein
LA is a lipid anchor that promotes insertion of the compound into a plasma membrane represented by formulae (IIa) or (IIIa):

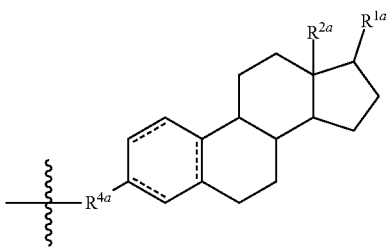

(IIa)

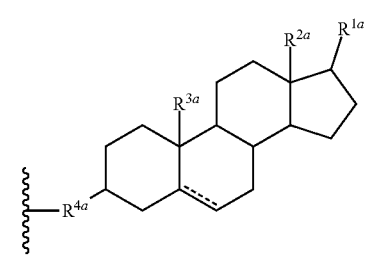

(IIIa)

wherein
R$^{1a}$ is an optionally substituted C$_{1-12}$ alkyl group;
R$^{2a}$ and R$^{3a}$ are independently H or C$_{1-3}$alkyl;
R$^{4a}$ is C, O, NH or S;
===== represents a single or double bond;

L is a linker represented by the formula (IVa):

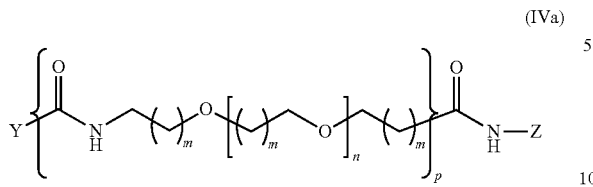

wherein

Z is the attachment group between the linker and the lipid anchor and is -$C_1$-$C_{10}$alkyl-, —$C_2$-$C_{10}$alkenyl-, —$C_2$-$C_{10}$alkynyl-, —$C_1$-$C_{10}$alkylC(O)—, —$C_2$-$C_{10}$alkenylC(O)— or —$C_2$-$C_{10}$alkynylC(O)—; or Z, together with the adjacent amine, is an optionally C-terminal amidated amino acid selected from aspartic acid, glutamic acid, asparagine, glutamine, histidine, cysteine, lysine, arginine, serine or threonine; wherein the amino acid is attached to the lipid anchor via its side-chain functional group;

Y is the attachment group between the linker and the modulator of an endosomal GPCR and is —O—, —NH—, —S—, —C(O)—, —C(O)NH—, —C(O)O— or —C(O)S—; or Y, together with the adjacent amido group is an amino acid selected from aspartic acid, glutamic acid, asparagine, glutamine, histidine, cysteine, lysine, arginine, serine or threonine; wherein the amino acid is attached to the modulator of an endosomal GPCR via its side-chain functional group;

or

Z is the attachment group of the linker to the lipid anchor LA; wherein Z is defined by:
- a1) $C_1$-$C_{10}$alkyl-, —$C_2$-$C_{10}$alkenyl-, —$C_2$-$C_{10}$alkynyl-, —$C_1$-$C_{10}$alkylC(O)—, —$C_2$-$C_{10}$alkenylC(O)— or —$C_2$-$C_{10}$alkynylC(O)—; or
- b1) together with the adjacent amine, an optionally C-terminally amidated amino acid selected from aspartic acid, glutamic acid, asparagine, glutamine, histidine, cysteine, lysine, arginine, serine or threonine; wherein the amino acid is attached to the lipid anchor via its side-chain functional group; and Y is the attachment group of the linker to the modulator X, which is a modulator of the endosomal neurokinin-1 receptor ($NK_1R$), wherein
- a2) Y is defined by —O—, —NH—, —S—, —C(O)—, —C(O)NH—, —C(O)O—, —O—C(O)—, —NH—C(O)—, or —C(O)S—; or
- b2) Y when taken together with the adjacent amido group, is defined by:
  - a. an alpha amino acid selected from aspartic acid, glutamic acid, asparagine, glutamine, histidine, cysteine, lysine, arginine, serine or threonine; wherein the alpha amino acid is optionally attached to the modulator of the endosomal $NK_1R$ via the side-chain functional group of at least one of said alpha amino acids; or
  - b. a beta, gamma or delta amino acid comprising a side-chain functional group which is also found in aspartic acid, glutamic acid, asparagine, glutamine, histidine, cysteine, lysine, arginine, serine or threonine; wherein said beta, gamma or delta amino acid is optionally attached to the modulator of the endosomal $NK_1R$ via at least one of said side-chain functional groups; or
  - c. a peptide formed from alpha, beta, gamma or delta amino acids, wherein the peptide comprises at least one alpha, beta, gamma or delta amino acid which has a side-chain functional group which is also found in aspartic acid, glutamic acid, asparagine, glutamine, histidine, cysteine, lysine, arginine, serine or threonine; or combinations thereof, wherein said peptide is optionally attached to the modulator of the endosomal $NK_1R$ via at least one of said side-chain functional groups;

m is 1 or 2;

n is from 1 to 20;

p is from 1 to 8; and

X is a modulator of an endosomal GPCR; or pharmaceutically acceptable salts thereof.

In a preferred embodiment, X is a modulator of the endosomal $NK_1$ receptor.

The substance P (SP) neurokinin 1 receptor ($NK_1R$) mediates pain and inflammation (Steinhoff, M. S. et al. *Physiol Rev* 2014, 94, 265-301). Although preclinical studies with antagonists of plasma membrane $NK_1R$ signaling support its involvement in neurological and inflammatory disorders, these antagonists are ineffective treatments for chronic diseases. The $NK_1R$ rapidly and completely redistributes to endosomes at sites of pain transmission in the spinal cord (Marvizon, J. C. et al. *J Neurosci* 1997, 17, 8129-8136) and inflammation in the vasculature (Bowden, J. J. et al. *Proc Natl Acad Sci USA* 1994, 91, 8964-8968), and is believed to internalize in patients with chronic pain and inflammation (Jarcho, J. M. et al. Pain, 2013).

It has surprisingly been found that endosomal $NK_1R$ signaling generates subcellular signals that underlie neuronal activation and hyperalgesia. Painful and pro-inflammatory stimuli, including the transient receptor potential vanilloid 1 agonist capsaicin, stimulate SP release from primary sensory nociceptors in laminae I, II of the dorsal horn, where SP stimulates $NK_1R$ endocytosis in spinal neurons. It was found that the $NK_1R$ antagonist spantide was unable to ameliorate capsaicin-evoked hyperalgesia, probably due to metabolism and clearance of the compound. However, when the same $NK_1R$ antagonist was incorporated into the tripartite compounds of the present invention, hyperalgesia was inhibited for more than 120 minutes, suggesting that antagonism of the $NK_1R$ in endosomes is an effective treatment against pain.

Modulation of SP-mediated $NK_1R$ activation has been implicated in the treatment and prevention of a wide variety of disorders including depression and mood disorders, anxiety disorders, substance addiction-related disorders, alcohol-related disorders, sleep disorders, eating disorders, autism spectrum disorders, attention-deficit/hyperactivity disorder personality disorders, and cancer. Modulators of $NK_1R$ may also be useful for the treatment and prevention of inflammation, allergic disorders, neurological disorders, emesis, pain and cancer.

In one embodiment, the present invention provides tripartite compounds of the formula (I) represented by formula (Ic):

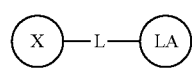

wherein

LA is a lipid anchor that promotes insertion of the compound into a plasma membrane;

L is a linker moiety of 1 nm to 50 nm in length; and

X is a modulator of the endosomal $NK_1R$;

wherein, in a preferred embodiment of the present invention, the lipid anchor partitions into lipid membranes that are insoluble in non-ionic detergent at 4° C.; or a pharmaceutically acceptable salt thereof.

In a preferred embodiment, the compound of formula (Ic) is selected from:

The individual moieties of the tripartite compound of the present invention including X, L, LA, Y, Z, the spacer between Y and Z, M, $F^1$, $F^2$, $R^1$ and $R^{2'}$ which are linked to each other as schematically described in FIG. 1.

Accordingly, the modulator X is formed from the moieties M, and $R^1$, wherein $R^1$ includes the moieties $F^1$, $R^{2'}$ and $F^2$. The part $F^1$ is used to covalently link M with $R^{2'}$, and $F^2$ is used to covalently link $R^{2'}$ with Y, Y being a part of the linker L.

Compound 1

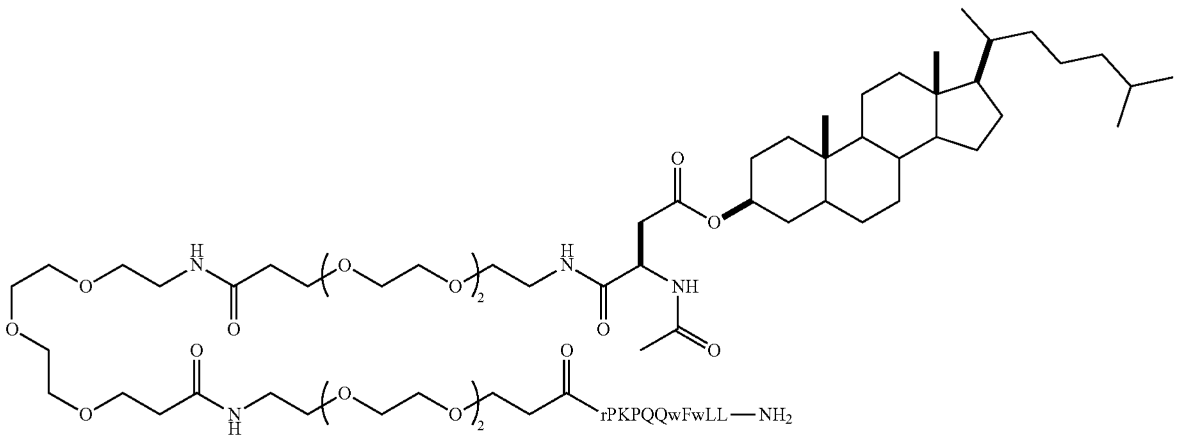

Compound 2 or

Compound 3

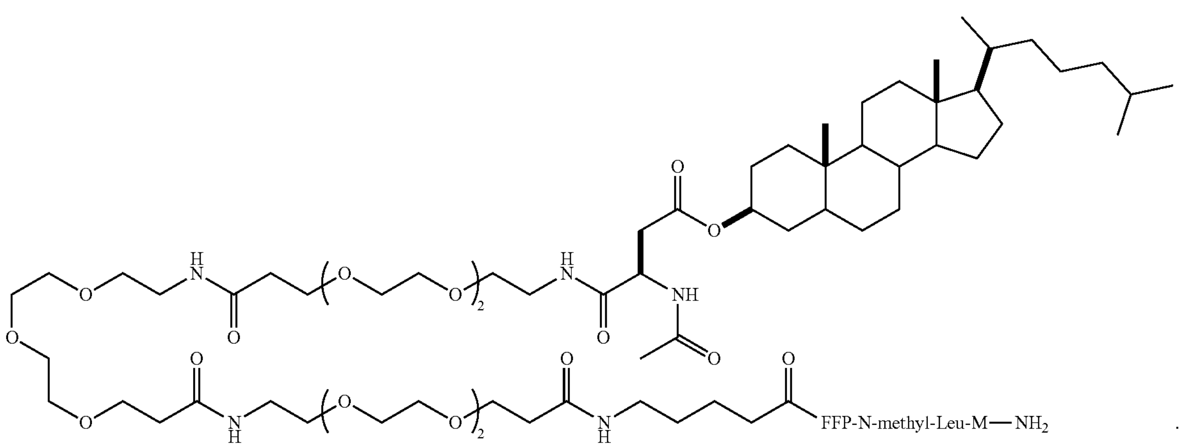

.

or pharmaceutically acceptable salts thereof.

Moieties F¹ and F² are covalently linked to R²' without being limited to any specific substitution pattern. The bonding pattern of F¹ and F² at R²' is only limited by the availability of the functional groups present on F¹, F² and R²'.

Preferred modulator moieties are as indicated by the following structures:

Moiety —R²'—F¹-M, which is covalently linked to the linker L by —F²— as shown in the following structure. Moiety —R²'—F¹-M under this definition does not include F² which is only indicated in the structure for further illustration:

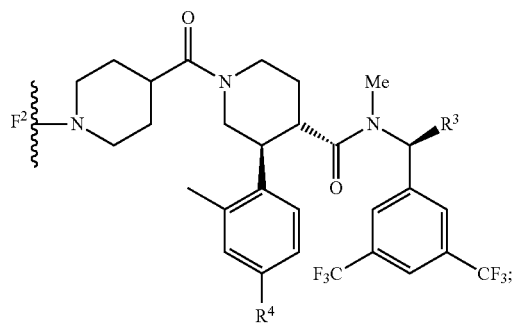

wherein R³ is hydrogen or —CH₃; R⁴ is hydrogen or fluorine; or a pharmaceutically acceptable salt thereof.

Moiety —R²'—F¹-M, which is covalently linked to the linker L by —F²— as shown in the following structure. Moiety —R²'—F¹-M under this definition does not include F² which is only indicated in the structure for further illustration:

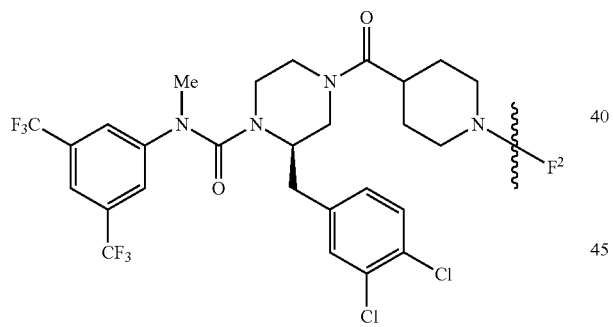

The following seven moieties —F²—R²'—F¹-M, which are covalently linked by Y to the linker L as shown in the following structures (Moieties —F—R²'—F¹-M under this definition do not include Y which is only indicated in the three structures for further illustration:

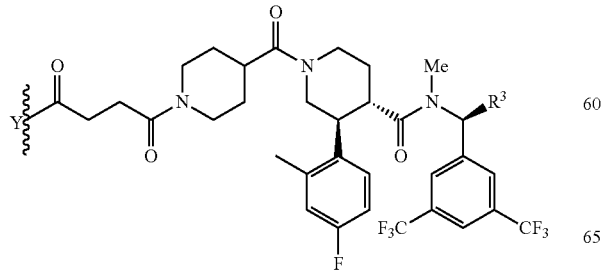

-continued

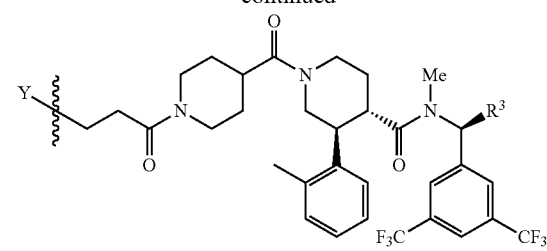

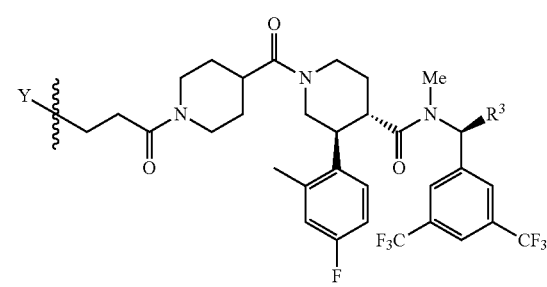

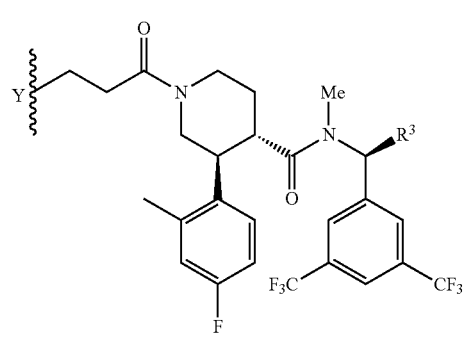

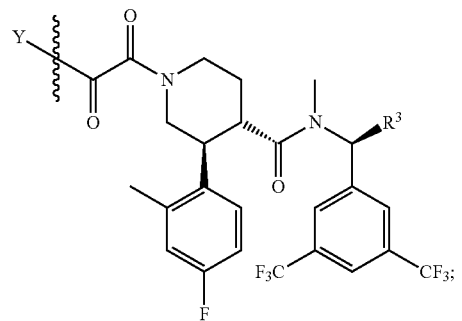

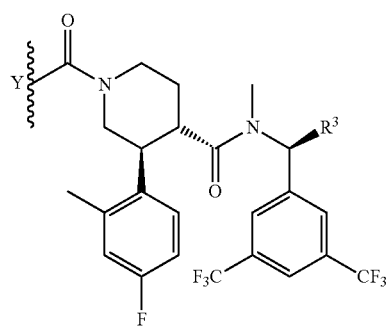

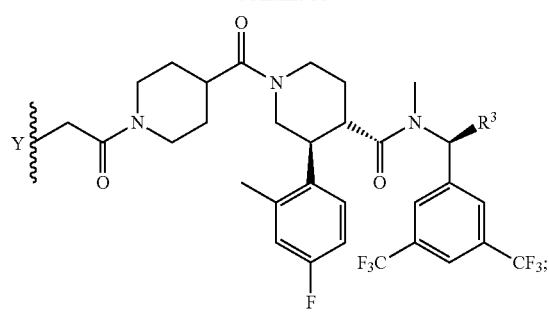

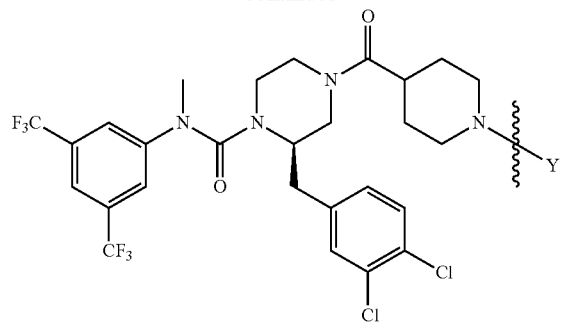

and combinations thereof, wherein $R^3$ is hydrogen atom or $CH_3$; $R^4$ is hydrogen atom or fluorine; or pharmaceutically acceptable salts thereof.

The following seven moieties —$F^2$—$R^{2'}$—$F^1$-M, which are covalently linked by Y to the linker L as shown in the following structures (Moieties —$F^2$—$R^{2'}$-FM under this definition do not include Y which is only indicated in the three structures for further illustration:

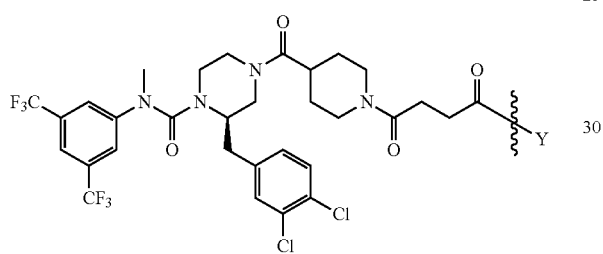

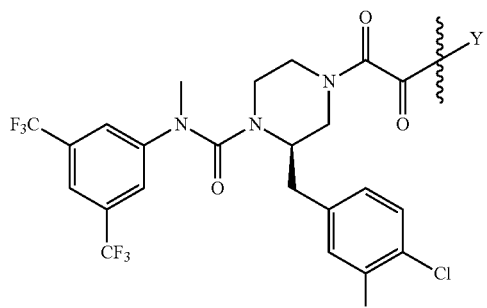

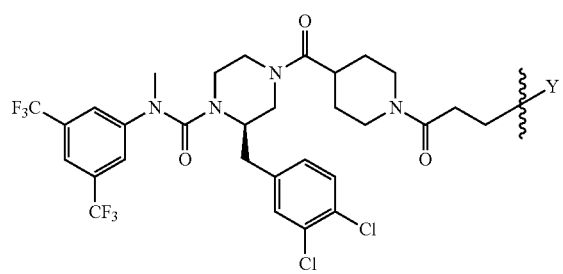

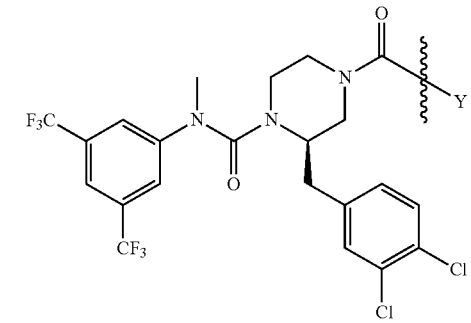

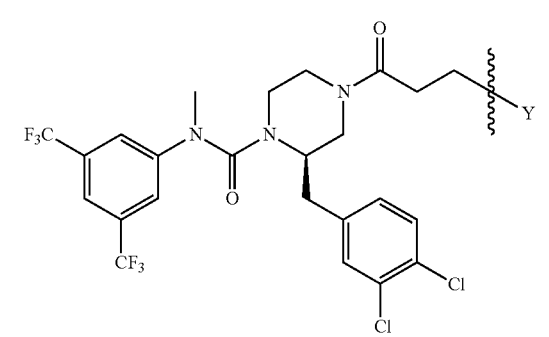

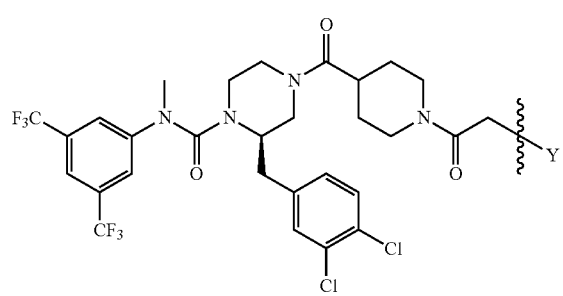

and combinations thereof; or pharmaceutically acceptable salts thereof.

The tripartite compounds X-L-LA having the following structures:

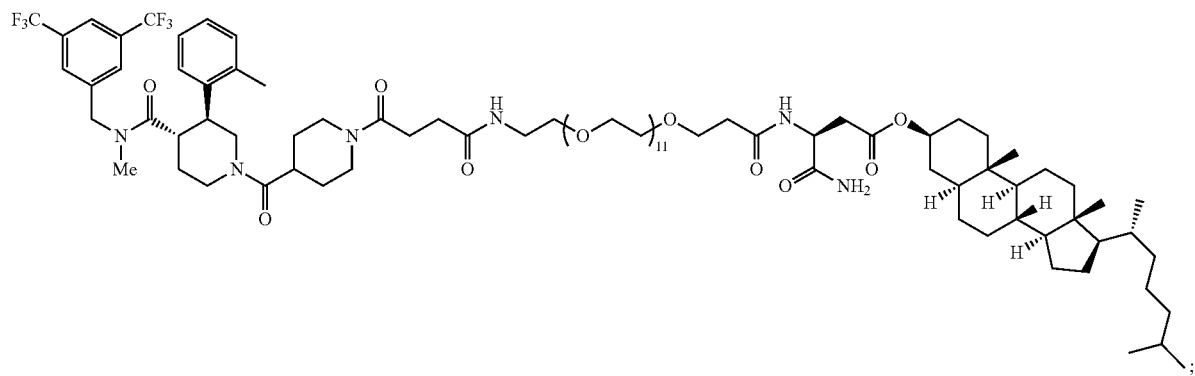
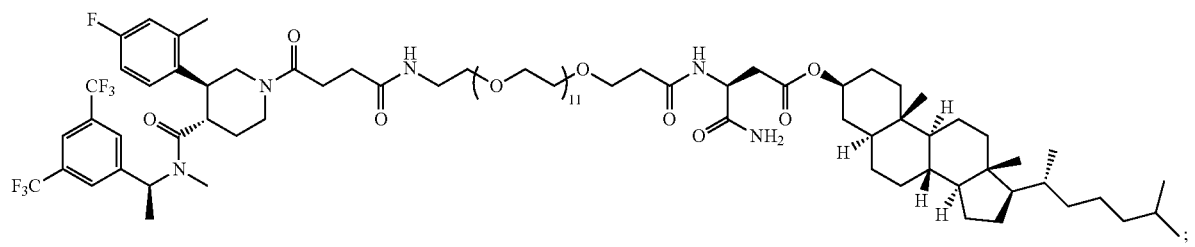
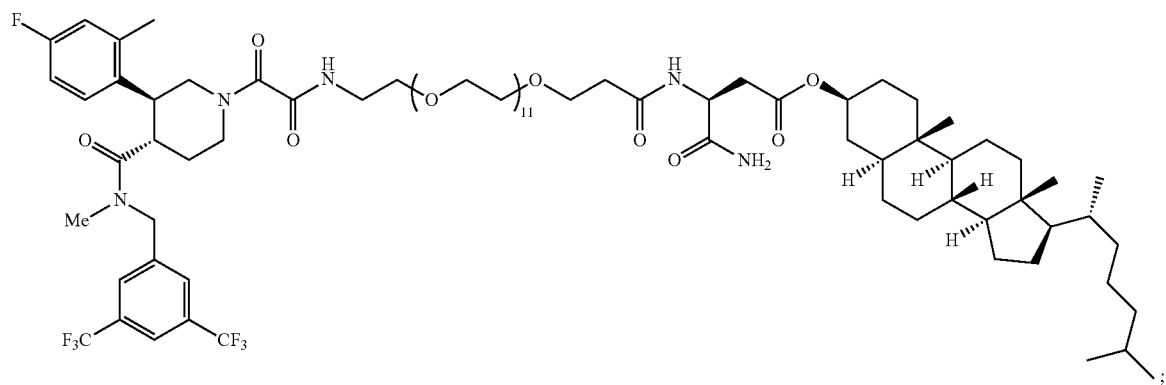
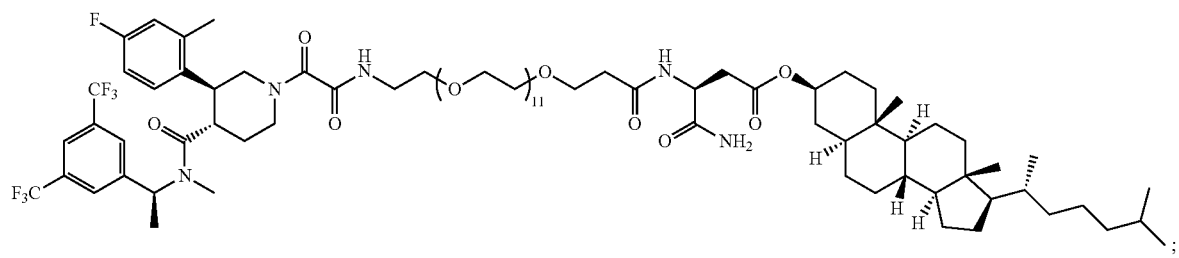
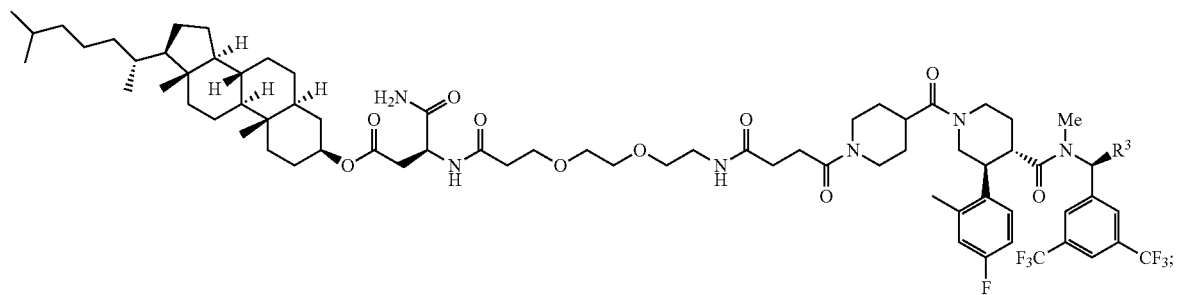

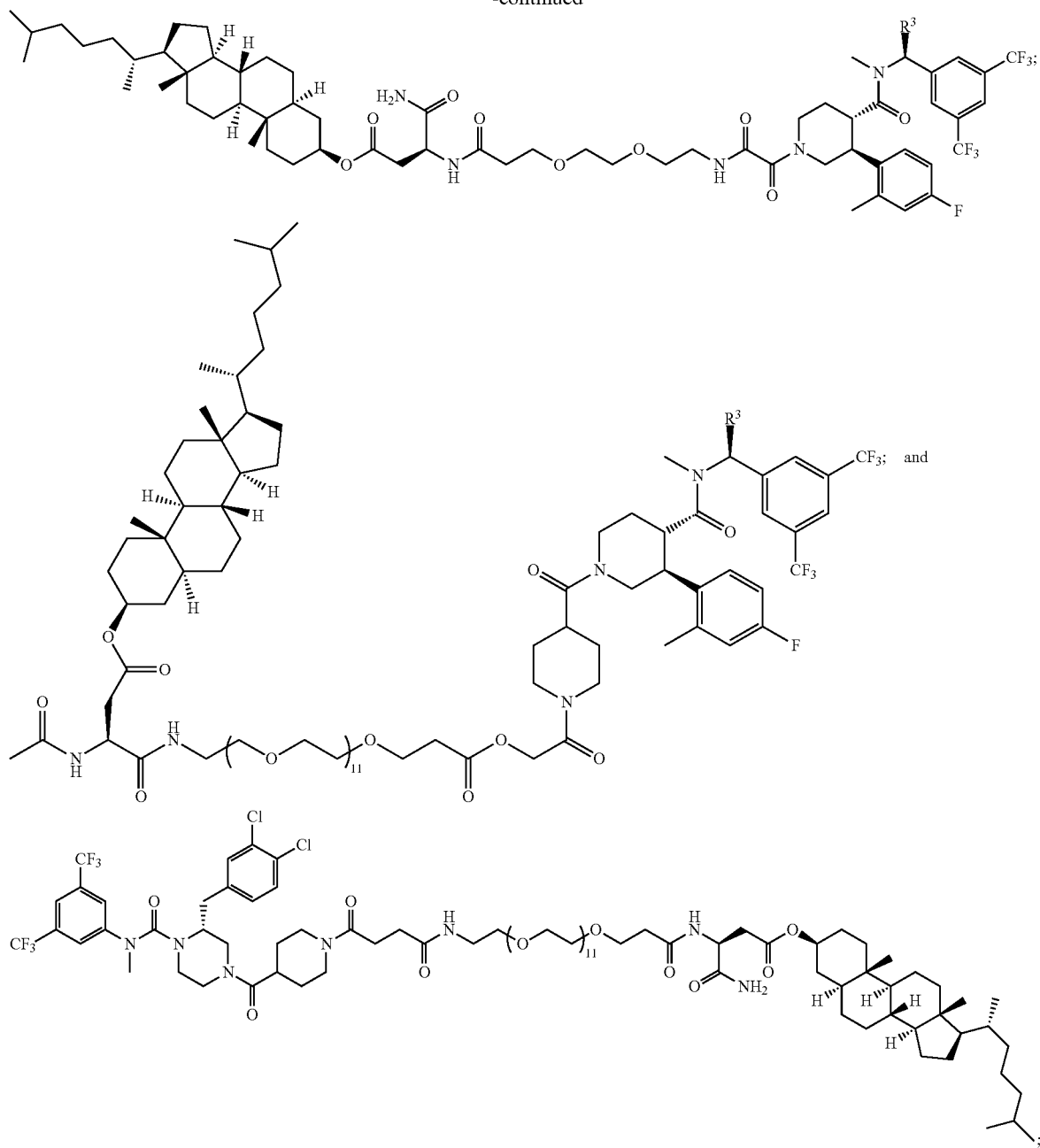

wherein R³ is hydrogen atom or —CH₃; or a pharmaceutically acceptable salt thereof.

In one embodiment the present invention provides a method for the treatment of a disease or disorder mediated by endosomal NK₁R signaling, comprising administering to a subject in need thereof an effective amount of a compound of formula (Ic) as herein defined.

In another embodiment, the present invention provides the use of a compound of formula (Ic) as herein defined in the manufacture of a medicament for the treatment of a disease or disorder mediated by endosomal NK₁R signaling.

In another embodiment the present invention provides the use of the tripartite compounds for the treatment of a disease or disorder mediated by endosomal NK₁R signalling.

In a further embodiment, the present invention provides a compound of formula (Ic) as herein defined for use in the treatment of a disease or disorder mediated by endosomal NK₁R signaling.

In a preferred embodiment, the disease or disorder mediated by endosomal NK₁R signaling is selected from chemotherapy-induced nausea and vomiting (CINV), cyclic vomiting syndrome, postoperative nausea and vomiting, affective and addictive disorders including depression and anxiety, generalised anxiety disorder (GAD), gastrointestinal disorders including inflammatory bowel disease, irritable bowel syndrome, gastroparesis and functional dyspepsia, respiratory disorders including COPD and asthma, urogenital disorders, sensory disorders and pain including somatic pain and visceral pain, pruritus, viral and bacterial infections and proliferative disorders (cancer).

Within the context of the present invention, the term "pain" includes chronic inflammatory pain (e.g. pain associated with rheumatoid arthritis, osteoarthritis, rheumatoid spondylitis, gouty arthritis and juvenile arthritis); musculoskeletal pain, lower back and neck pain, sprains and strains, neuropathic pain, sympathetically maintained pain, myositis, pain associated with cancer and fibromyalgia, pain associated with migraine, pain associated with cluster and chronic daily headache, pain associated with influenza or other viral infections such as the common cold, rheumatic fever, pain associated with functional bowel disorders such as non-ulcer dyspepsia, non-cardiac chest pain and irritable bowel syndrome, pain associated with myocardial ischemia, post-operative pain, headache, toothache, dysmenorrhea, neuralgia, fibromyalgia syndrome, complex regional pain syndrome (CRPS types I and II), neuropathic pain syndromes (including diabetic neuropathy, chemoterapeutically induced neuropathic pain, sciatica, non-specific lower back pain, multiple sclerosis pain, HIV-related neuropathy, post-herpetic neuralgia, trigeminal neuralgia) and pain resulting from physical trauma, amputation, cancer, toxins or chronic inflammatory conditions. In a preferred embodiment the pain is somatic pain or visceral pain.

In another preferred embodiment, the modulator of an endosomal GPCR is an inhibitor of the endosomal CGRP receptor.

The neuropeptide calcitonin gene related peptide (CGRP) is widely expressed in both the peripheral and central nervous systems by polymodal primary sensory neurons of the trigeminal ganglion. Release of CGRP in the dorsal spinal cord has been associated with nociceptive transmission and release of CGRP from perivascular nerve endings causes neurogenic vasodilation and release of inflammatory mediators from mast cells (Benemei, S. et al., *Curr. Opin. Pharmacol.* 2009, 9(1), 9-14; Durham P. L. *N. Engl, J. Med.* 2004, 350, 1073-1074). CGRP contributes to pain transmission and inflammation and is believed to play an integral role in the pathophysiology of migraine (Durham, P. L. *Headache*, 2006, 46, S3-S8). CGRP is also believed to contribute to the pain and inflammation associated with arthritis including osteoarthritis and rheumatoid arthritis (Walsh, D. A. et al., *Br. J. Clin. Pharmacol.*, 2015, 80(5), 965-978).

The CGRP receptor (CGRP-R) is comprised of two subunits, the calcitonin receptor-like receptor (CLR, a GPCR) and the receptor activity modifying protein-1 (RAMP1). Coexpression and dimerization of CLR and RAMP1 creates the CGRP-R, with high affinity for CGRP (Russell, F. A. et al., *Physiological Reviews*, 2014, 94, 1099-1142). CGRP binding and receptor activation has been shown to lead to phosphorylation of CLR and internalization of the CGRP-R as a stable complex (Hilairet, S. et al., *J. Biol. Chem.*, 2001, 276, 42182-42190). Internalization was found to be both dynamin- and β-arrestin dependent, indicating that the formation of a trinary complex between CLR, RAMP1 and β-arrestin leads to chathin-coated pit mediated endocytosis.

Early studies with the selective CGRP-R antagonist Telcagepant showed promising results with administration of the compound resulting in the effective treatment of moderate to severe migraine attacks with a primary endpoint of pain relief at 2 hours (Ho, T. W. et al., *Neurology*, 2008, 70(16) 1304-1312). Telcagepant also showed promise as an effective treatment for sustained pain relief over 24 hours and relief from migraine related symptoms such as photophobia, phonophobia and nausea. However, a Phase IIa clinical trial of the compound was ceased as Telcagepant was found to significantly increase levels of the hepatic liver enzyme alanine transaminase to an unacceptable level for the patient.

Another antagonist identified for the CGRP-R is $CGRP_{8-37}$. CGRP exists in two forms in humans, α-CGRP and β-CGRP. These forms are derived from separate genes and differ with respect to three amino acids, but exhibit similar biological functions (Durham, P. L and Vause, C. V. *CNSDrugs*, 2010, 24(7), 539-548). Binding studies of the 37-amino acid neuropeptide α-CGRP have revealed that the first seven N-terminal amino acids are essential for receptor activation. SAR studies have demonstrated that the remaining 18 amino acids ($CGRP_{8-37}$) are important for receptor recognition and docking. However, this sequence was found not to be involved in receptor activation. This finding led to the use of $CGRP_{8-37}$ as a CGRP-R inhibitor.

In one embodiment, the present invention provides compounds of the formula (I) represented by the formula (Id):

(Id)

wherein

A is a lipid anchor that promotes insertion of the compound into a plasma membrane;

L is a linker moiety of 1 nm to 50 nm in length; and

X is a modulator of the endosomal CGRP-R;

wherein, in a preferred embodiment of the present invention, the lipid anchor partitions into lipid membranes that are insoluble in non-ionic detergent at 4° C.; or a pharmaceutically acceptable salt thereof.

In one embodiment, X is the CGRP-R antagonist olcegepant.

In another embodiment, X is the CGRP-R antagonist $CGRP_{8-37}$ and the compound of formula (Id) is represented by Compound 4:

Compound 4

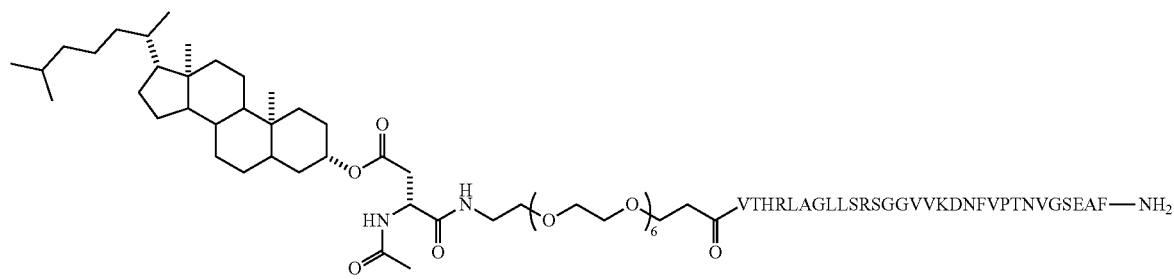

or a pharmaceutically acceptable salt thereof.

In one embodiment the present invention provides a method for the treatment of a disease or disorder mediated by endosomal CGRP receptor signaling, comprising administering to a subject in need thereof an effective amount of a compound of formula (Id) as herein defined.

In another embodiment, the present invention provides the use of a compound of formula (Id) as herein defined in the manufacture of a medicament for the treatment of a disease or disorder mediated by endosomal CGRP receptor signaling.

In a further embodiment, the present invention provides a compound of formula (Id) as herein defined for use in the treatment of a disease or disorder mediated by endosomal CGRP receptor signaling.

In one embodiment, the disease or disorder mediated by endosomal CGRP receptor signaling is migraine and symptoms associated with migraine including pain, photophobia, phonophobia, nausea and vomiting, sensory disorders, pain including somatic pain and visceral pain, pain associated with cluster and chronic daily headache, respiratory disorders including COPD and asthma, gastrointestinal disorders including inflammatory bowel disease, irritable bowel syndrome, gastroparesis and functional dyspepsia, and chronic inflammatory disorders including osteoarthritis and rheumatoid arthritis.

In a preferred embodiment, the disease or disorder mediated by endosomal CGRP receptor signaling is migraine and its associated symptoms.

Figure 2:
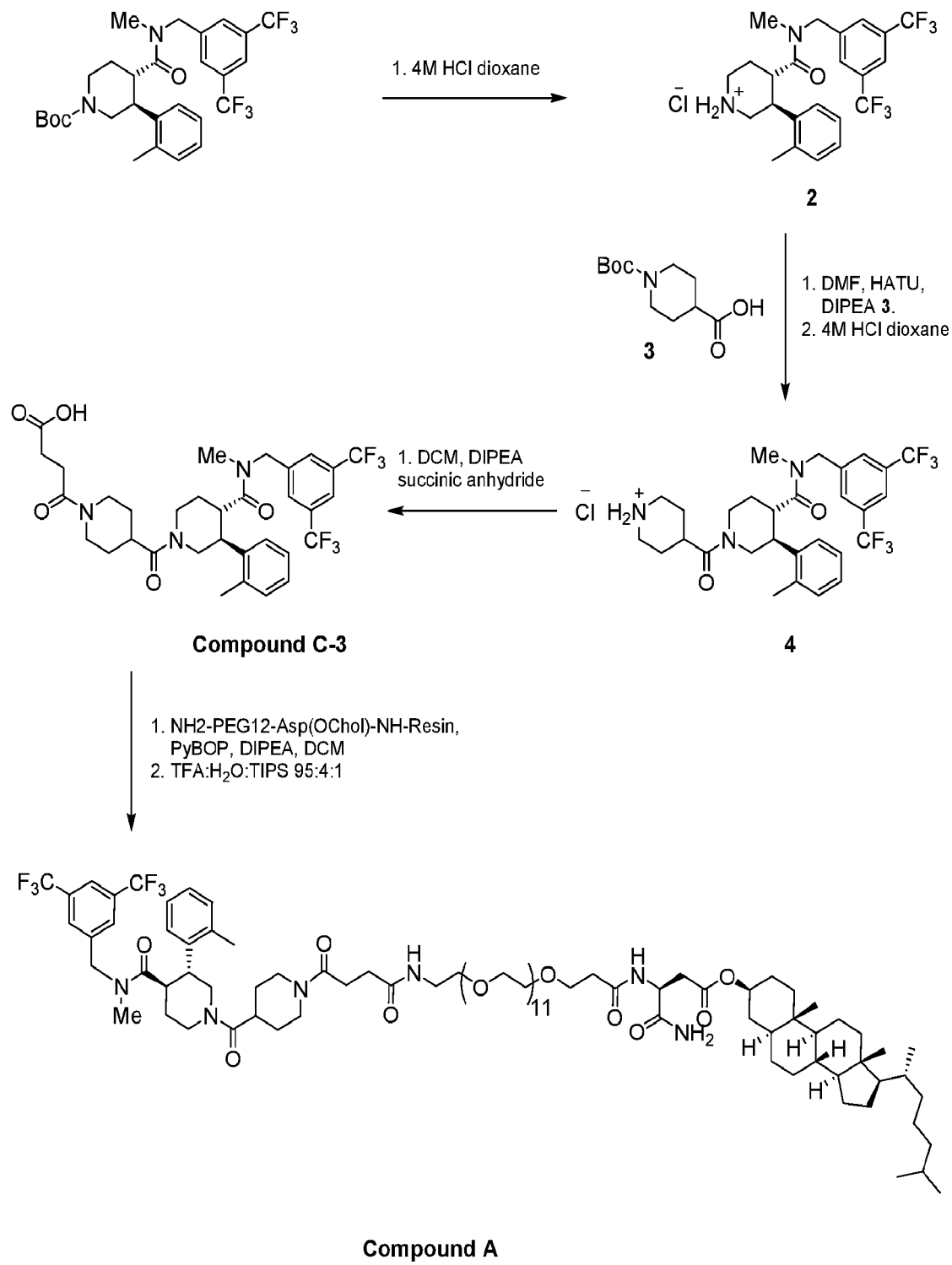
FIG. 2: Synthetic procedure for preparing the tripartite compound Compound A.
Figure 3:
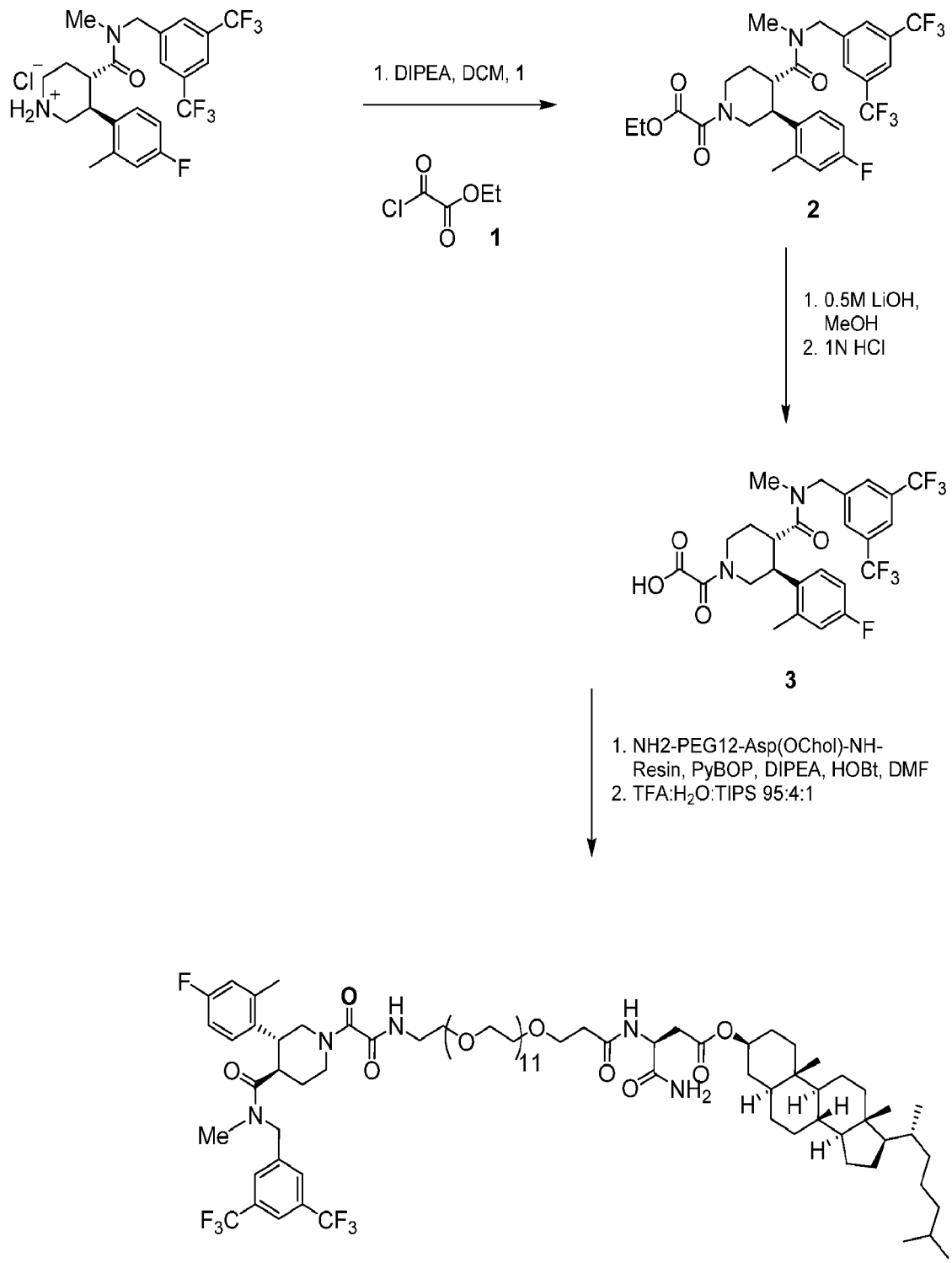
FIG. 3: Synthetic procedure for preparing the tripartite compound Compound B.
Figure 4:
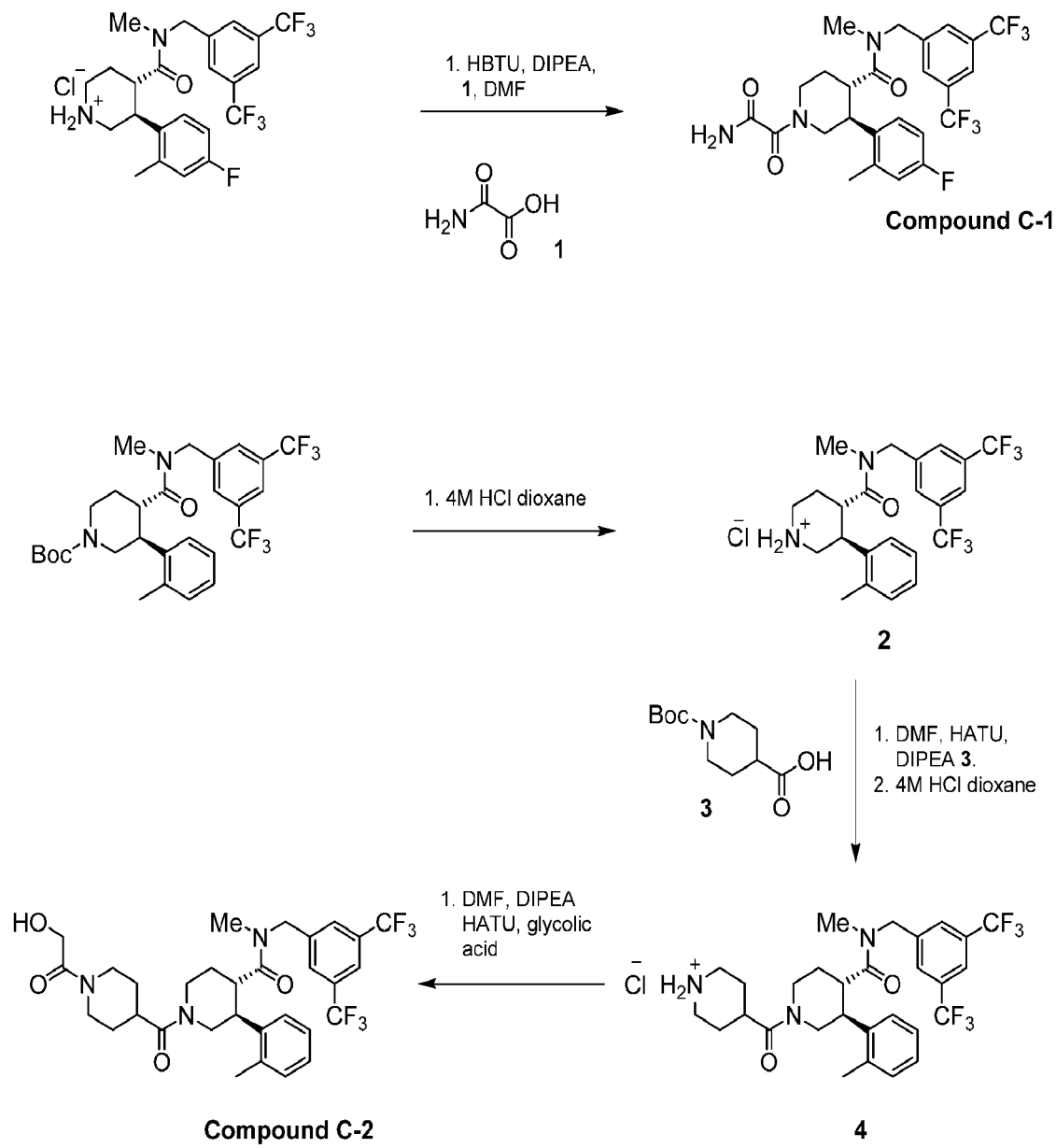
FIG. 4: Synthetic procedure for preparing the core modulator moieties Compound C-1 and Compound C-2, before coupling these modulators via —Y— to the linker.

General strategies for synthesising the compounds of the present invention rely on established methods of synthetic organic chemistry, as well as solid phase peptide chemistry with the usual operations applied when adding and removing protecting groups during the preparation. Key synthetic steps are illustrated in FIGS. 2 to 4, while FIG. 1 helps to further understand the various moieties and their pattern of linkage to form the final tripartite compound.

Synthesis of cholesteryl glycolic acid, 3-cholesterylamine, and cholesteryl glycine are described in the literature (Hussey, S. L. et al., *J. Am. Chem. Soc.* 2001, 123, 12712-12713; Hussey, S. L. et al., *Org. Lett.* 2002, 4, 415-418; Martin, S. E. et al., *Bioconjugate Chem.* 2003, 14, 67-74). Lipid anchors of the formula (IIIa) having an amide, sulfonamide, urea or carbamate functional group at position 3 of the steroid structure can be prepared from 3-cholesterylamine, for example, 3-cholesterylamine can be reacted with succinic anhydride in the presence of DMAP to afford the corresponding succinyl substituted compound. The corresponding sulfonamide can be obtained by reaction of 3-cholesterylamine with chlorosulfonylacetic acid, which can be prepared as described in the literature (Hinman, R. L. and Locatell, L. *J. Am. Chem. Soc.* 1959, 81, 5655-5658). The corresponding urea or carbamate can be prepared according to literature procedures via the corresponding isocyanate (Knolker, H.-J. T. et al., *Angew. Chem. Int. Ed.* 1995, 34, 2497; Knolker, H.-J. et al., *Synlett* 1996, 502; Knolker, H.-J. and. Braxmeier, T. *Tetrahedron Lett.* 1996, 37, 5861). Intermediates of compound (IIIa) having a phosphate or carboxymethylated phosphate at position 3 of the steroid structure can be prepared as described in the literature (Golebriewski, Keyes, Cushman, *Bioorg. Med. Chem.* 1996, 4, 1637-1648; Cusinato, Habeler, et al., *J. Lipid Res.* 1998, 39, 1844-1851; Himber, Missano, et al., *J. Lipid Res.* 1995, 36, 1567-1585). Lipid anchors of the formula (IIIa) having a thiol at position 3 of the steroid structure can be prepared as described in the literature (J. G. Parkes, J. G. et al., *Biochim. Biophys. Acta* 1982, 691, 24-29), the corresponding carboxymethylated thiols are obtainable by simple alkylation as described for the corresponding amines and alcohols. Lipid anchors of the formula (IIIa) having a difluoromethylenesulfone derivative at position 3 of the steroid structure can be prepared as described in the literature (Lapiene, J. et al., *Bioorg. Med. Chem. Lett.* 2004, 14, 151-155). Introduction of various side chains at position 17 of lipid anchors of the formula (IIIa) can be achieved by use of literature protocols starting from dehydroisoandrosterone or pregnenolone (Bergmann, E. D. et al., *J. Am. Chem. Soc.* 1959, 81, 1239-1243 and references therein). Lipid anchors of the formula (IIIa) which are derived from cholestane are obtainable from the corresponding precursors which are derived from cholesterol by reduction of the 5,6-double bond using literature protocols, e.g. hydrogenation in the presence of various transition metal catalysts.

Lipid anchors of the formula (IIa) having an oxygen derived substituent at position 3 are prepared in a similar manner as described for the lipid anchors of the formula (IIIa) starting from estrone. Lipid anchors of the formula (IIa) having nitrogen derived substitution at position 3 can be prepared in a similar manner as described for lipid anchors of the formula (IIIa) starting from 3-amino estrone, which can be prepared as described in the literature (Zhang, X. and Sui, Z. *Tetrahedron Lett.* 2003, 44, 3071-3073; Woo, L. W. L. et al., *Steroid Biochem. Molec. Biol.* 1996, 57, 79-88). Lipid anchors of the formula (IIa) having a sulfur derived substituent at position 3 can be prepared in a similar manner as described for lipid anchors of the formula (IIIa) starting from 3-thioestrone, which can be prepared as described in the literature (Woo, L. W. L. et al., *J. Steroid Biochem. Molec. Biol.* 1996, 57, 79-88). Introduction of various side chains at position 17 of the estrone structure can be achieved by a Wittig approach, followed by hydrogenation of the resulting double bond as described in the literature (Peters, R. H. et al., *J. Org. Chem.* 1966, 31, 24-26). Further manipulations within the side chain (e.g. double bond constructions, cycloalkyl decorations) can be achieved by standard protocols (Suzuki-couplings, etc.).

Lipid anchors of the formula (VIa) belonging to the class of ceramides, dehydroceramides and dihydroceramides with different hydrocarbon groups are obtainable as outlined in the literature (A. H. Merrill, Jr., Y. A. Hannun (Eds.), Methods in Enzymology, Vol. 311, Academic Press, 1999; Koskinen, P. M and Koskinen, A. M. P. *Synthesis* 1998, 1075). In particular, sphingosine base can be used as key intermediate for all lipid anchors of the formula (VIa) having oxygen derived substitution at position 1 of the sphingosine backbone. The corresponding amino derivatives are obtainable by substitution of the sulfonates, which can be prepared from the alcohols according to known protocols. Alkylation and acylation of 1-amino or 1-hydroxy derivatives can be achieved by reaction with bromo acetic acid and succinic anhydride, respectively. The thioacetylated derivative can be prepared by substitution of a sulfonate with mercapto acetic acid. Phosphate and sulfate derivatives are obtainable as described in the literature (A. H. Merrill, Jr., YA A. Hannun (Eds.), Methods in Enzymology, Vol. 311, Academic Press, 1999; Koskinen, P. M. and Koskinen, A. M. P. *Synthesis* 1998, 1075). Acylation, sulfonylation, urea and carbamate formation can be achieved by standard procedures. Lipid anchors of the formula (VIa) wherein $R^{5a}$ is an amino or amino derived function can be prepared starting from sphingosine base, which is available as published by Koskinen (Koskinen, *P. M. and Koskinen, A. M. P. Synthesis* 1998, 1075), using standard protocols. The corresponding 2-oxygen substituted sphingolipids can be obtained by a strategy published by Yamanoi (Yamanoi, T. et al., *Chem.*

Lett. 1989, 335). Lipid anchors of the formula (VIa), wherein both $R^{8a}$ represent a hydroxy group, are obtainable by bishydroxylation of the corresponding alkene using known protocols. The corresponding monohydroxy derivatives can be prepared as described in the literature (Howell, A. R. and Ndakala, A. J. *Curr. Org. Chem.* 2002, 6, 365-391). Modification of substituents $R^{6a}$ and $R^{9a}$ in lipid anchors of the formula (VIa) can be achieved by protocols and strategies outlined in various review articles (Harwood, H. J. Chem. Rev. 1962, 62, 99-154; Gensler, W. *J. Chem. Rev.* 1957, 57, 191-280).

Lipid anchors of the formula (VIIa) are obtainable by protocols described in the literature (Miller, S. et al., *J. Prakt. Chem.* 2000, 342, 779) and by combinations thereof with protocols described for the preparation of lipid anchors of the formula (VIIa).

Lipid anchors of the formula (VIIIa), wherein $R^{4a}$ and $R^{5a}$ are oxygen derived substituents, can be prepared starting from commercially available (R)-(−)-2,2-dimethyl-1,3-dioxolane-4-methanol as outlined by Fraser-Reid (Schlueter, U. Lu, *J. and Fraser-Reid, B. Org. Lett.* 2003, 5, 255-257). Variation of substituents $R^{6a}$ in compounds of formula (VIIIa) can be achieved by protocols and strategies outlined in various review articles (Harwood, H. J. *Chem. Rev.* 1962, 62, 99-154; Gensler, W. *J. Chem. Rev.* 1957, 57, 191-280). Lipid anchors of the formula (VIIIa), wherein $R^{4a}$ and $R^{5a}$ are nitrogen derived substituents, are obtainable either starting from the corresponding oxygen substituted systems by nucleophilic replacement of the corresponding sulfonates and further modifications as outlined above, or starting from 1,2,3-triaminopropane which is obtainable as described in the literature (Henrick, K. et al., *J Chem. Soc. Dalton Trans.* 1982, 225-227).

Lipid anchors of the formula (IXa) are obtainable in a similar fashion as lipid anchors of the formula (VIIa) or alternatively by ring closing metathesis of ω-ethenylated intermediates of lipid anchors of the formula (VIIIa).

Lipid anchors of the formulae (Xa) and (XIa) are obtainable by synthetic strategies described in the literature (Xue, J. and Guo, Z. *Bioorg. Med. Chem. Lett.* 2002, 12, 2015-2018; Xue, J. and Guo, Z. *J Am. Chem. Soc.* 2003, 16334-16339; Xue, J. et al., *J. Org. Chem.* 2003, 68, 4020-4029; Shao, N., Xue, J. and Guo, Z. *Angew. Chem. Int. Ed.* 2004, 43, 1569-1573) and by combinations thereof with methods described above for the preparation of lipid anchors of the formulae (VIa) and (VIIIa).

Lipid anchors of the formulae (XIIa), (XIIIa) and (XIVa) are obtainable by total synthesis following synthetic strategies described in the literature (Knolker, H.-J. *Chem. Soc. Rev.* 1999, 28, 151-157; Knolker, H.-J. and Reddy, K. R. *Chem. Rev.* 2002, 102, 4303-4427; Knolker, H.-J. and Knoll, *J. Chem. Commun.* 2003, 1170-1171; Knolker, H.-J. *Curr. Org. Synthesis* 2004, 1).

Lipid anchors of the formula (XVa) can be prepared by Nenitzescu-type indole synthesis starting from 4-methoxy-3-methylbenzaldehyde to afford 6-methoxy-5-methylindole. Ether cleavage, triflate formation and Sonogashira coupling leads to the corresponding 6-alkynyl substituted 5-methylindole. Nilsmeier formylation and subsequent nitromethane addition yields the 3-nitro vinyl substituted indole derivative which is subjected to a global hydrogenation resulting in the formation of the 6-alkyl substituted 5-methyltryptamine. Acylation of the amino group using succinyl anhydride completes the preparation.

Known solid or solution phase techniques may be used in the synthesis of the peptides of the present invention, such as coupling of the N- or C-terminus to a solid support (typically a resin) followed by step-wise synthesis of the linear peptide. Protecting group chemistries for the protection of amino acid residues, including side chains, are well known in the art and may be found, for example, in: Theodora W. Greene and Peter G. M. Wuts, *Protecting Groups in Organic Synthesis* (Third Edition, John Wiley & Sons, Inc, 1999), the entire contents of which is incorporated herein by reference.

Methods for the preparation of compounds as described herein will be apparent to those skilled in the art and will comprise the steps of a) defining the distance between (a) phosphoryl head group(s) or an equivalent head group of the lipid anchor and a binding and/or interaction site of the modulator of an endosomal GPCR; b) selecting a linker which is capable of spanning the distance as defined in (a); and c) bonding the lipid anchor and the modulator of an endosomal GPCR by the linker as selected in (b).

Corresponding working examples for such a method are given herein and are illustrated in the appended examples. The person skilled in the art is in a position to deduce relevant binding sites or interactions sites of a given or potential modulator of an endosomal GPCR and, accordingly, to determine the distance between (a) phosphoryl head group(s) or an equivalent head group of the lipid anchor and a binding and/or interaction site of the modulator of an endosomal GPCR. Such methods comprise, but are not limited to molecular modelling, in vitro and/or molecular-interaction or binding assays (e.g. yeast two or three hybrid systems, peptide spotting, overlay assays, phage display, bacterial displays, ribosome displays), atomic force microscopy as well as spectroscopic methods and X-ray crystallography. Furthermore, methods such as site-directed mutagenesis may be employed to verify deduced interaction sites of a given modulator of an endosomal GPCR or of a candidate modulator of an endosomal GPCR and its corresponding target.

As explained above, the modulator of an endosomal GPCR is a molecule which is involved in biological processes which take place in endosomes and is mediated by a G protein-coupled receptor.

The skilled addressee will understand that the selection of a linker comprises the selection of linkers known in the art as well as the generation and use of novel linkers, for example, by molecular modelling and corresponding synthesis or further methods known in the art. The term "spanning" as used herein with reference to step b) refers to the length of the linker selected to place the modulator of an endosomal GPCR at the correct locus on the a receptor when the lipid anchor forms part of the lipid layer of the endosome.

The skilled addressee is readily in the position to deduce, verify and/or evaluate the lipophilicity of a given tripartite compound as well as of the individual moiety as described herein. Corresponding test assays to determine endosomal GPCR targeting are provided herein in the examples.

The skilled addressee will understand that the purpose of the linker moiety is to connect the lipid anchor to the modulator of an endosomal GPCR in order to allow the modulator of an endosomal GPCR to interact with the receptor when the lipid anchor is anchored in the endosome membrane. The lipid anchor and the linker will contain functional groups allowing for the two to be covalently bonded. The nature of the functional group of the lipid anchor is in no way limited and may include, for example, an amine group that forms an amide bond with the linker, or a hydroxyl or carboxylic acid group that forms and ether or ester bond with the linker.

Similarly, the skilled addressee will understand that selection of the functional group at the end of the linker that connects with the endosomal GPCR will be dictated primarily by any available functional groups on the modulator for an endosomal GPCR of choice. For example, if the endosomal GPCR comprises a free amine or carboxylic acid group, it is envisaged that the functional group of the linker will comprise a complementary carboxylic acid or amine to form an amide bond.

It will be understood that the compounds of the present invention may exist in one or more stereoisomeric forms (e.g. diastereomers). The present invention includes within its scope all of these stereoisomeric forms either isolated (in, for example, enantiomeric isolation), or in combination (including racemic mixtures and diastereomic mixtures).

The present invention contemplates the use of amino acids in both L and D forms, including the use of amino acids independently selected from L and D forms, for example, where the peptide comprises two alanine residues, each alanine residue may have the same, or opposite, absolute stereochemistry. Unless stated otherwise, the amino acid is taken to be in the L-configuration.

The invention thus also relates to compounds in substantially pure stereoisomeric form with respect to the asymmetric centres of the amino acid residues, e.g., greater than about 90% de, such as about 95% to 97% de, or greater than 99% de, as well as mixtures, including racemic mixtures, thereof. Such diastereomers may be prepared by asymmetric synthesis, for example, using chiral intermediates, or mixtures may be resolved by conventional methods, e.g., chromatography, or use of a resolving agent.

Where the compounds of the present invention require purification, chromatographic techniques such as high-performance liquid chromatography (HPLC) and reverse-phase HPLC may be used. The compounds may be characterised by mass spectrometry and/or other appropriate methods.

Where the compound comprises one or more functional groups that may be protonated or deprotonated (for example at physiological pH) the compound may be prepared and/or isolated as a pharmaceutically acceptable salt. It will be appreciated that the compound may be zwitterionic at a given pH. As used herein the expression "pharmaceutically acceptable salt" refers to the salt of a given compound, wherein the salt is suitable for administration as a pharmaceutical. Such salts may be formed, for example, by the reaction of an acid or a base with an amine or a carboxylic acid group respectively.

Pharmaceutically acceptable acid addition salts may be prepared from inorganic and organic acids. Examples of inorganic acids include hydrochloric acid, hydrobromic acid, sulfuric acid, nitric acid, phosphoric acid and the like. Examples of organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutically acceptable base addition salts may be prepared from inorganic and organic bases. Corresponding counter ions derived from inorganic bases include the sodium, potassium, lithium, ammonium, calcium and magnesium salts. Organic bases include primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine.

Acid/base addition salts tend to be more soluble in aqueous solvents than the corresponding free acid/base forms.

The present invention also provides a pharmaceutical composition comprising a therapeutically effective amount of a tripartite compound as hereinbefore defined, or a pharmaceutically acceptable salt thereof, together with at least one pharmaceutically acceptable carrier or diluent.

The term "composition" is intended to include the formulation of an active ingredient with encapsulating material as carrier, to give a capsule in which the active ingredient (with or without other carrier) is surrounded by carriers.

While the compounds as hereinbefore described, or pharmaceutically acceptable salts thereof, may be the sole active ingredient administered to the subject, the administration of other active ingredient(s) with the compound is within the scope of the invention. In one or more embodiments it is envisaged that a combination of two or more of the compounds of the invention will be administered to the subject. It is envisaged that the compound(s) could also be administered with one or more additional therapeutic agents in combination. The combination may allow for separate, sequential or simultaneous administration of the compound(s) as hereinbefore described with the other active ingredient(s). The combination may be provided in the form of a pharmaceutical composition.

The term "combination", as used herein refers to a composition or kit of parts where the combination partners as defined above can be dosed dependently or independently or by use of different fixed combinations with distinguished amounts of the combination partners, i.e., simultaneously or at different time points. The combination partners can then, e.g., be administered simultaneously or chronologically staggered, that is at different time points and with equal or different time intervals for any part of the kit of parts. The ratio of the total amounts of the combination partners to be administered in the combination can be varied, e.g. in order to cope with the needs of a patient sub-population to be treated or the needs of the single patient which different needs can be due to age, sex, body weight, etc. of the patients.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the active compound care should be taken to ensure that the activity of the compound is not destroyed in the process and that the compound is able to reach its site of action without being destroyed. In some circumstances it may be necessary to protect the compound by means known in the art, such as, for example, micro encapsulation. Similarly the route of administration chosen should be such that the compound reaches its site of action.

Those skilled in the art may readily determine appropriate formulations for the compounds of the present invention using conventional approaches. Identification of preferred pH ranges and suitable excipients, for example antioxidants, is routine in the art. Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

The compounds as hereinbefore described, or pharmaceutically acceptable salts thereof, may be prepared in parenteral dosage forms, including those suitable for intravenous, intrathecal, and intracerebral or epidural delivery. The pharmaceutical forms suitable for injectable use include sterile injectable solutions or dispersions, and sterile powders for the extemporaneous preparation of sterile injectable solutions. They should be stable under the conditions of manufacture and storage and may be preserved against reduction or oxidation and the contaminating action of microorganisms such as bacteria or fungi.

The solvent or dispersion medium for the injectable solution or dispersion may contain any of the conventional solvent or carrier systems for the active compound, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolarity, for example, sugars or sodium chloride. Optionally, the formulation for injection will be isotonic with blood. Prolonged absorption of the injectable compositions can be brought about by the use in the compositions of agents delaying absorption, for example, aluminium monostearate and gelatin. Pharmaceutical forms suitable for injectable use may be delivered by any appropriate route including intravenous, intramuscular, intracerebral, intrathecal, epidural injection or infusion.

Sterile injectable solutions are prepared by incorporating the compounds of the invention in the required amount in the appropriate solvent with various of the other ingredients such as those enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

Other pharmaceutical forms include oral and enteral formulations of the present invention, in which the active compound may be formulated with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal or sublingual tablets, troches, capsules, elixirs, suspensions, syrups, wafers, and the like. The amount of active compound in such therapeutically useful compositions is such that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the compounds of the invention may be incorporated into sustained-release preparations and formulations, including those that allow specific delivery of the active peptide to specific regions of the gut.

Liquid formulations may also be administered enterally via a stomach or oesophageal tube. Enteral formulations may be prepared in the form of suppositories by mixing with appropriate bases, such as emulsifying bases or water-soluble bases. It is also possible, but not necessary, for the compounds of the present invention to be administered topically, intranasally, intravaginally, intraocularly and the like.

Pharmaceutically acceptable vehicles and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate the compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically acceptable vehicle. The specification for the novel dosage unit forms of the invention are dictated by and directly dependent on (a) the unique characteristics of the active material and the particular therapeutic effect to be achieved, and (b) the limitations inherent in the art of compounding active materials for the treatment of disease in living subjects having a diseased condition in which bodily health is impaired as herein disclosed in detail.

As mentioned above the principal active ingredient may be compounded for convenient and effective administration in therapeutically effective amounts with a suitable pharmaceutically acceptable vehicle in dosage unit form. A unit dosage form can, for example, contain the principal active compound in amounts ranging from 0.25 µg to about 2000 mg. Expressed in proportions, the active compound may be present in from about 0.25 µg to about 2000 mg/mL of carrier. In the case of compositions containing supplementary active ingredients, the dosages are determined by reference to the usual dose and manner of administration of the said ingredients.

As used herein, the term "effective amount" refers to an amount of compound which, when administered according to a desired dosing regimen, provides the desired therapeutic activity. Dosing may occur once, or at intervals of minutes or hours, or continuously over any one of these periods. Suitable dosages may lie within the range of about 0.1 ng per kg of body weight to 1 g per kg of body weight per dosage. A typical dosage is in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

The terms "treatment" and "treating" as used herein cover any treatment of a condition or disease in an animal, optionally a mammal, like a human, and includes treating any disease or disorder that is mediated by endosomal GPCR signaling. The terms "prevention" and "preventing" as used herein cover the prevention or prophylaxis of a condition or disease in an animal, optionally a mammal, like a human and includes prevention of a disease or disorder that is mediated by endosomal GPCR signaling.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention will now be described with reference to the following non-limiting examples:

Example 1: Preparation Procedures of the Tripartite Compounds

The following examples are representative of the present invention, and provide detailed methods for preparing exemplary compounds of the present invention.

The tripartite compounds according to the present invention have been prepared by the following experimental procedures:

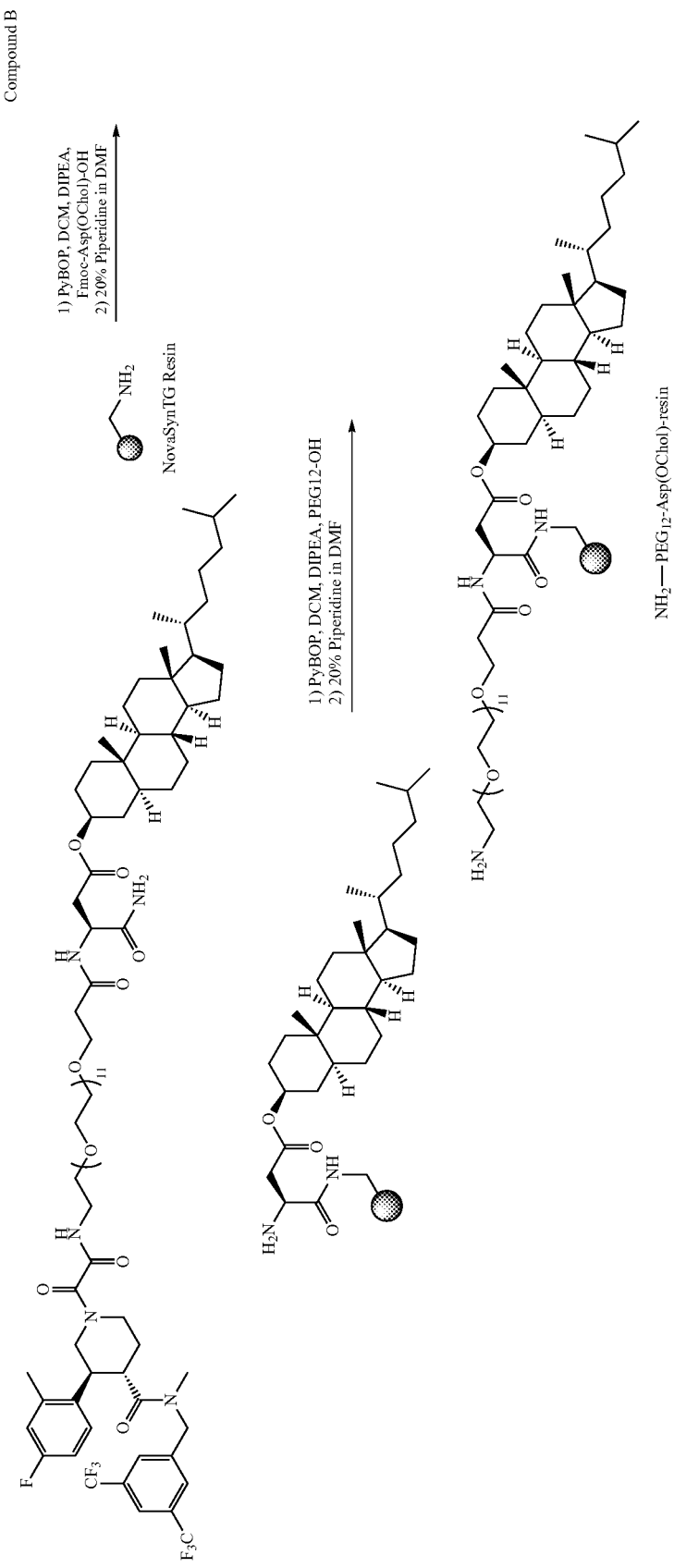

NH$_2$-PEG12-Asp(OChol)-Resin

Synthesis of the spacer-lipid conjugate was prepared by manual peptide synthesis with standard Fmoc chemistry on NovaSyn®TG$^R$ R resin (loading 0.18 mmol/g from NovaBiochem). Coupling of the Fmoc-Asp(OChol)-OH (1.5 eq) with (1H-Benzotriazol-1-yloxy)(tri-1-pyrrolidinyl)phosphonium hexafluorophosphate (PyBOP, 2 eq) in dichloromethane (DCM) with activation in situ using diisopropylethylamine (DIPEA, 3 eq) for 3 h. Fmoc deprotection was achieved using 20% piperidine in N,N-dimethylformamide (DMF). Fmoc-PEG12-OH (2 eq) was coupled to resin-bound NH$_2$-Asp(OChol) with PyBOP (2 eq) and DIPEA (3 eq) in DCM. Fmoc deprotection was achieved using 20% piperidine in N,N-dimethylformamide (DMF). Following final deprotection the NK1R antagonists were coupled to the spacer-lipid conjugate on resin.

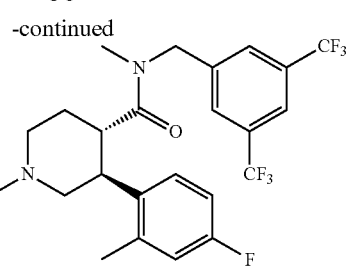

Compound B (3S,4S)—N-(3,5-bis(trifluoromethyl)benzyl)-3-(4-fluoro-2-methylphenyl)-N-methylpiperidine-4-carboxamide (500 mg, 1.0 mmol) in DCM (15 mL) was added DIPEA (3.47 mL, 2.0 mmol) followed by ethyl chloroxoacetate (1.67 mL, 1.5 mmol) and stirred at rt for 1 h. The mixture was diluted with DCM and washed with saturated bicarbonate and then 1N HCl. The organic layer was dried (MgSO$_4$), filtered, and concentrated to a residue and used directly in the next step.

The residue was dissolved in MeOH (5 mL) and 0.5M LiOH (4 mL, 2 mmol) was added and allowed to stir at rt for 2 h. The mixture was partitioned between 1N HCl and DCM. The organic layer was dried (MgSO$_4$), filtered, and concentrated to a residue that was purified by silica gel chromatography (DCM:MeOH, 95:5 to 80:20), providing 2-((3S,4S)-4-((3,5-bis(trifluoromethyl)benzyl)(methyl)carbamoyl)-3-(4-fluoro-2-methylphenyl)piperidin-1-yl)-2-oxoacetic acid as an amorphous foam (432 mg, 79%).

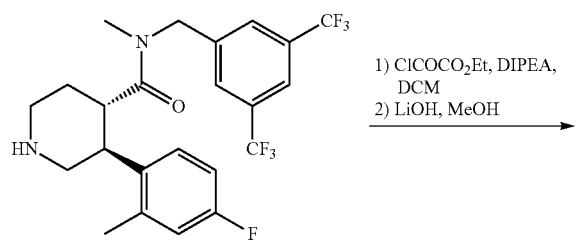

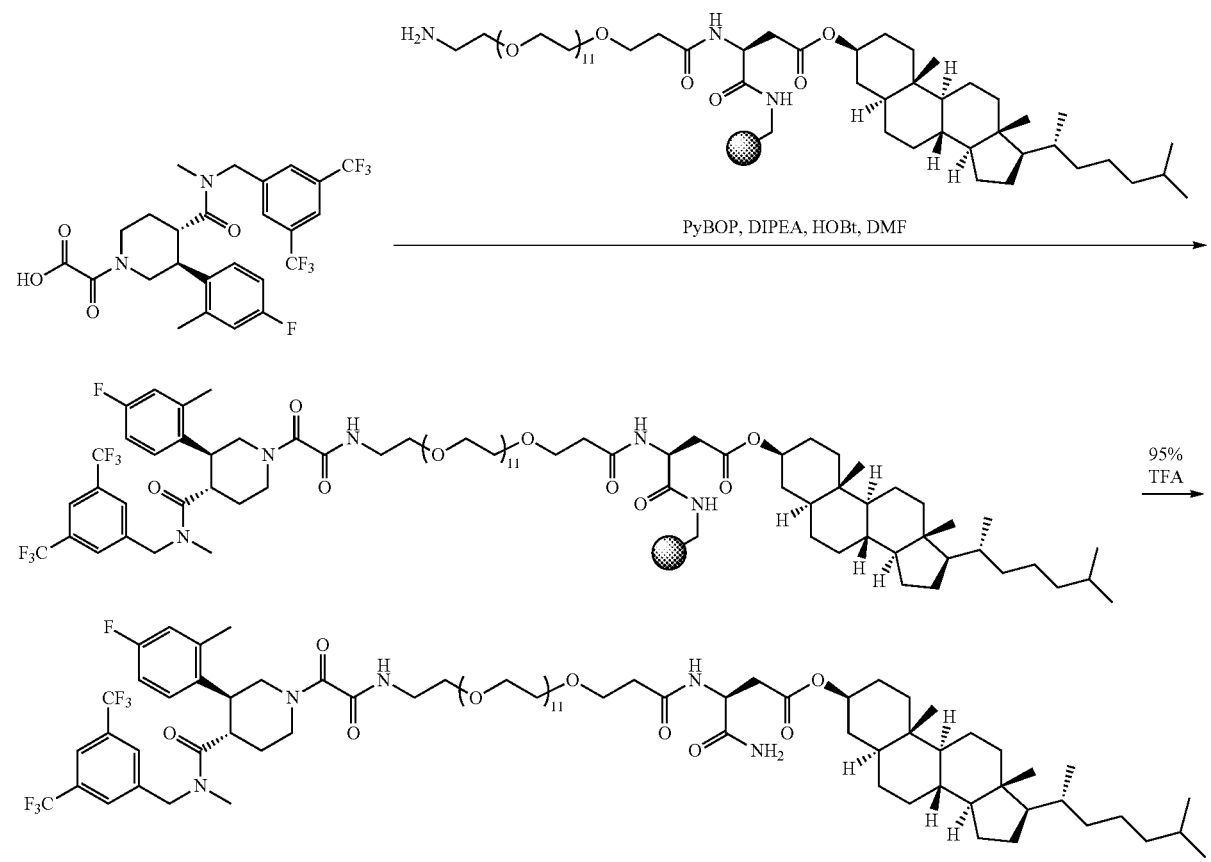

2-((3S,4S)-4-((3,5-bis(trifluoromethyl)benzyl)(methyl)carbamoyl)-3-(4-fluoro-2-methylphenyl)piperidine-4-carbyl)-2-oxoacetic acid (10 eq compared to resin loading) was coupled to resin-bound NH$_2$-PEG12-Asp(OChol)-resin (250 mg) with PyBOP (10 eq) and DIPEA (10 eq), HOBt (10 eq) in DMF overnight. The construct was then cleaved from resin using 95% trifluoroacetic acid and purified by silica gel chromatography (DCM:MeOH, 98:2 to 80:20), providing the tripartite probe Compound B as a viscous oil (34.8 mg).

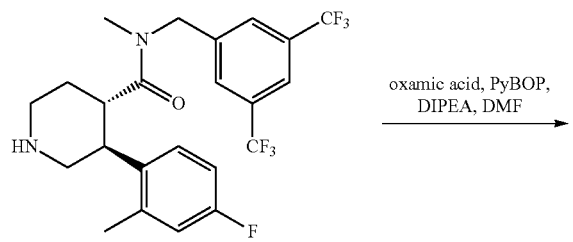

oxamic acid, PyBOP, DIPEA, DMF

Compound C-1

(3S,4S)—N-(3,5-bis(trifluoromethyl)benzyl)-3-(4-fluoro-2-methylphenyl)-N-methylpiperidine-4-carboxamide (50 mg, 0.1 mmol) in DMF (1.5 mL) was added oxamic acid (17 mg, 0.2 mmol), followed by PyBOP (104 mg, 0.2 mmol) and finally DIPEA (34 µL, 0.2 mmol) and stirred at rt overnight. The mixture was diluted with EtOAc and washed with saturated bicarbonate and then 1N HCl. The organic layer was dried (MgSO$_4$), filtered, and concentrated to a residue that was purified by reverse-phase high-performance liquid chromatography (HPLC) (Phenomenex Luna C8 column, Lane Cove, Australia) with 0.1% TFA/H$_2$O and 0.1% TFA/ACN as solvents, providing 2-((3S,4S)-4-((3,5-bis(trifluoromethyl)benzyl)(methyl)carbamoyl)-3-(4-fluoro-2-methylphenyl)piperidin-1-yl)-2-oxoacetic acid as an amorphous solid (47 mg, 88%).

Compound A

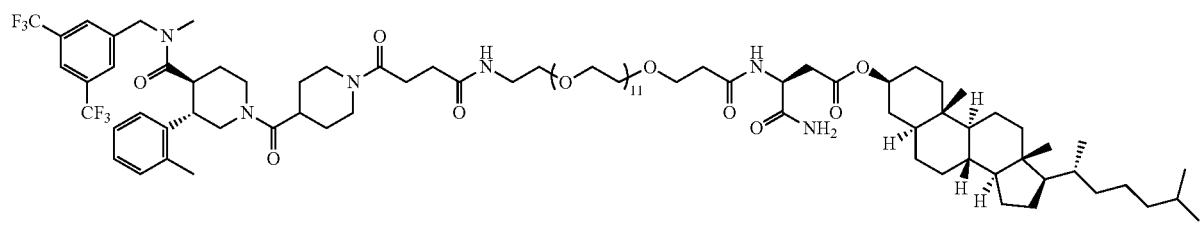

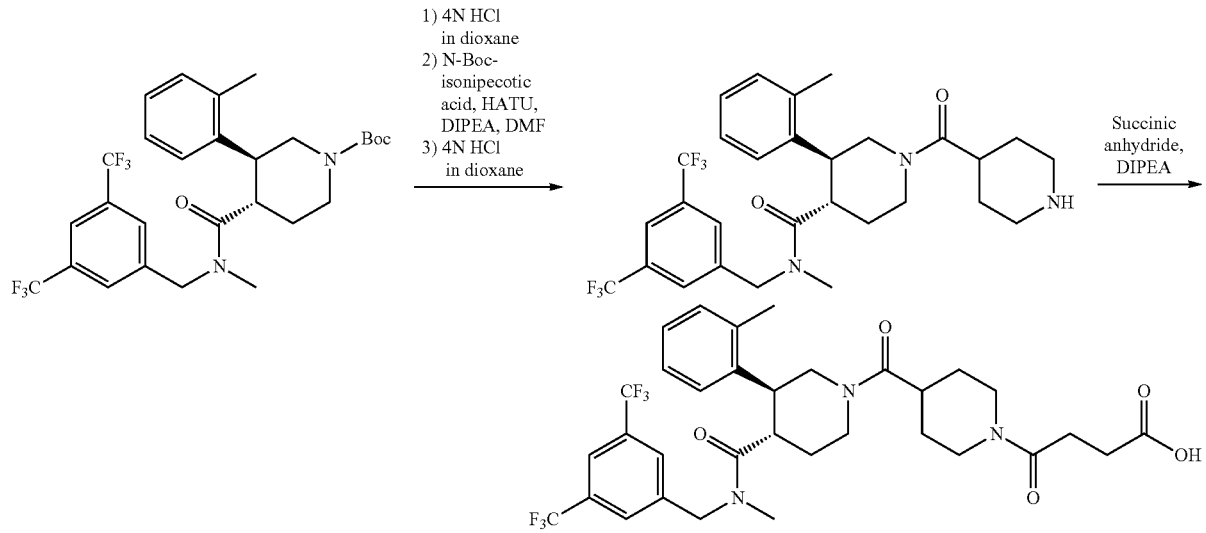

1) 4N HCl in dioxane
2) N-Boc-isonipecotic acid, HATU, DIPEA, DMF
3) 4N HCl in dioxane Succinic anhydride, DIPEA

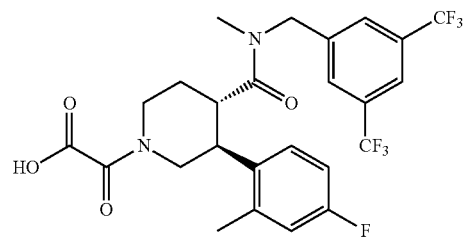

-continued

Compound C-3 tert-butyl (3S,4S)-4-((3,5-bis(trifluoromethyl)benzyl)(methyl)carbamoyl)-3-(o-tolyl)piperidine-1-carboxylate (200 mg, 0.36 mmol) was Boc deprotected with 4M HCl in dioxane (6 mL) at rt for 4 h. The mixture was concentrated and triturated with EtOAc to provide a solid (170 mg 96%). The de-Boc material (150 mg, 0.303 mmol) was coupled to N-Boc isonipecotic acid (76 mg, 0.334 mmol) with 1-[Bis(dimethylamino)methylene]-1H-1,2,3-triazolo[4,5-b]-pyridinium 3-oxide hexafluorophosphate (HATU) H (127 mg, 0.334 mmol), in DMF (3 mL) with activation in situ using DIPEA (158 µL, 0.909 mmol) for 3 h. The mixture was diluted with EtOAc and washed with water the saturated bicarbonate and finally brine. The organic layer was dried (MgSO₄), filtered, and concentrated to a residue that was purified by silica gel chromatography (EtOAc:pet ether, 50:50 to 100:0) providing a clear colorless resin (205 mg) that was immediately Boc deprotected with 4M HCl in dioxane (6 mL). Concentration after 3 h provides the deprotected intermediate 4 to a residue (180 mg, 98%). The (3S,4S)—N-(3,5-bis(trifluoromethyl)benzyl)-N-methyl-1-(piperidine-4-carbonyl)-3-(o-tolyl)piperidine-4-carboxamide (130 mg, 0.215 mmol) was coupled to succinic anhydride (24 mg, 0.236 mmol)) in DCM (3 mL) with activation in situ using DIPEA (112 µL, 0.644 mmol) for 3 h. The mixture was diluted with DCM washed with 1N HCl then brine. The organic layer was dried (MgSO₄), filtered, and concentrated to provide Compound C-3,4-(4-((3S,4S)-4-((3,5-bis(trifluoromethyl)benzyl)(methyl)carbamoyl)-3-(o-tolyl)piperidine-1-carbonyl)piperidin-1-yl)-4-oxobutanoic acid an amorphous foam (157 mg).

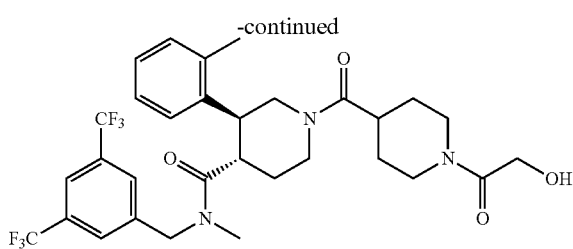

Compound C-2

(3S,4S)—N-(3,5-bis(trifluoromethyl)benzyl)-N-methyl-1-(piperidine-4-carbonyl)-3-(o-tolyl)piperidine-4-carboxamide (50 mg, 0.083 mmol) was dissolved in DMF (2 mL) and to this mixture was added glycolic acid (7 mg, 0.091 mmol), HATU (35 mg, 0.091 mmol) followed by DIPEA (43 µL, 0.248 mmol) and stirred at rt for 2 h. The mixture was diluted with ether and washed with water then 1N HCl. The organic layer was dried (MgSO₄), filtered, and concentrated to a residue that was purified by silica gel chromatography (MeOH:EtOAc, 10:90) providing a clear opaque resin (36 mg). The resin was triturated with pet ether to provide Compound C-2 (3S,4S)—N-(3,5-bis(trifluoromethyl)benzyl)-1-(1-(2-hydroxyacetyl)piperidine-4-carbonyl)-N-methyl-3-(o-tolyl)piperidine-4-carboxamide as an amorphous solid (26 mg, 50%).

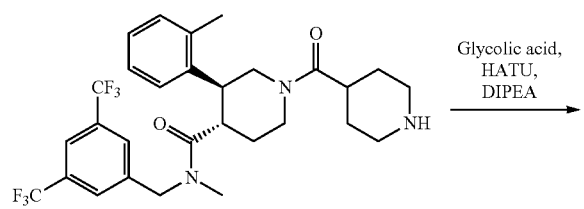

Glycolic acid, HATU, DIPEA ⟶

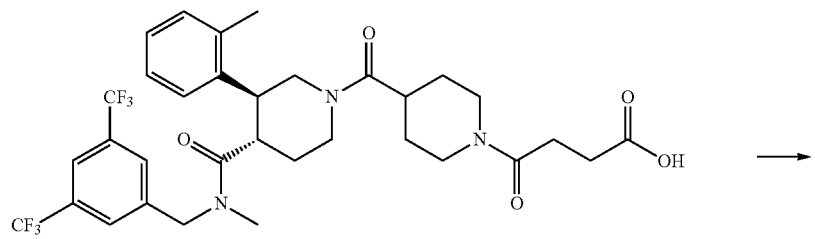

Compound C-3

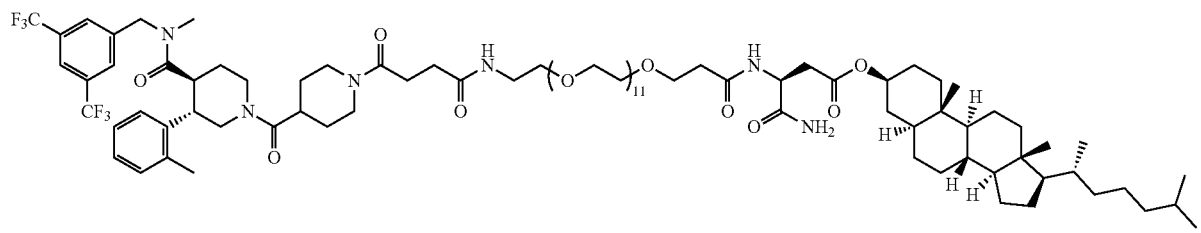

A. The acid Compound C-3 4-(4-((3S,4S)-4-((3,5-bis(trifluoromethyl)benzyl)(methyl)carbamoyl)-3-(o-tolyl)piperidine-1-carbonyl)piperidin-1-yl)-4-oxobutanoic acid (130 mg) was coupled to resin-bound NH$_2$-PEG12-Asp(OChol)-resin (250 mg) with PyBOP (2 eq) and DIPEA (3 eq) in DCM overnight. The construct was then cleaved from resin using 95% trifluoroacetic acid and purified by reverse-phase high-performance liquid chromatography (HPLC) (Phenomenex Luna C8 column, Lane Cove, Australia) with 0.1% TFA/H$_2$O and 0.1% TFA/ACN as solvents, providing the tripartite probe Compound A as a viscous oil (30.2 mg).

The following compounds can be made using the same chemistry and starting from the indicated NK1 antagonist.

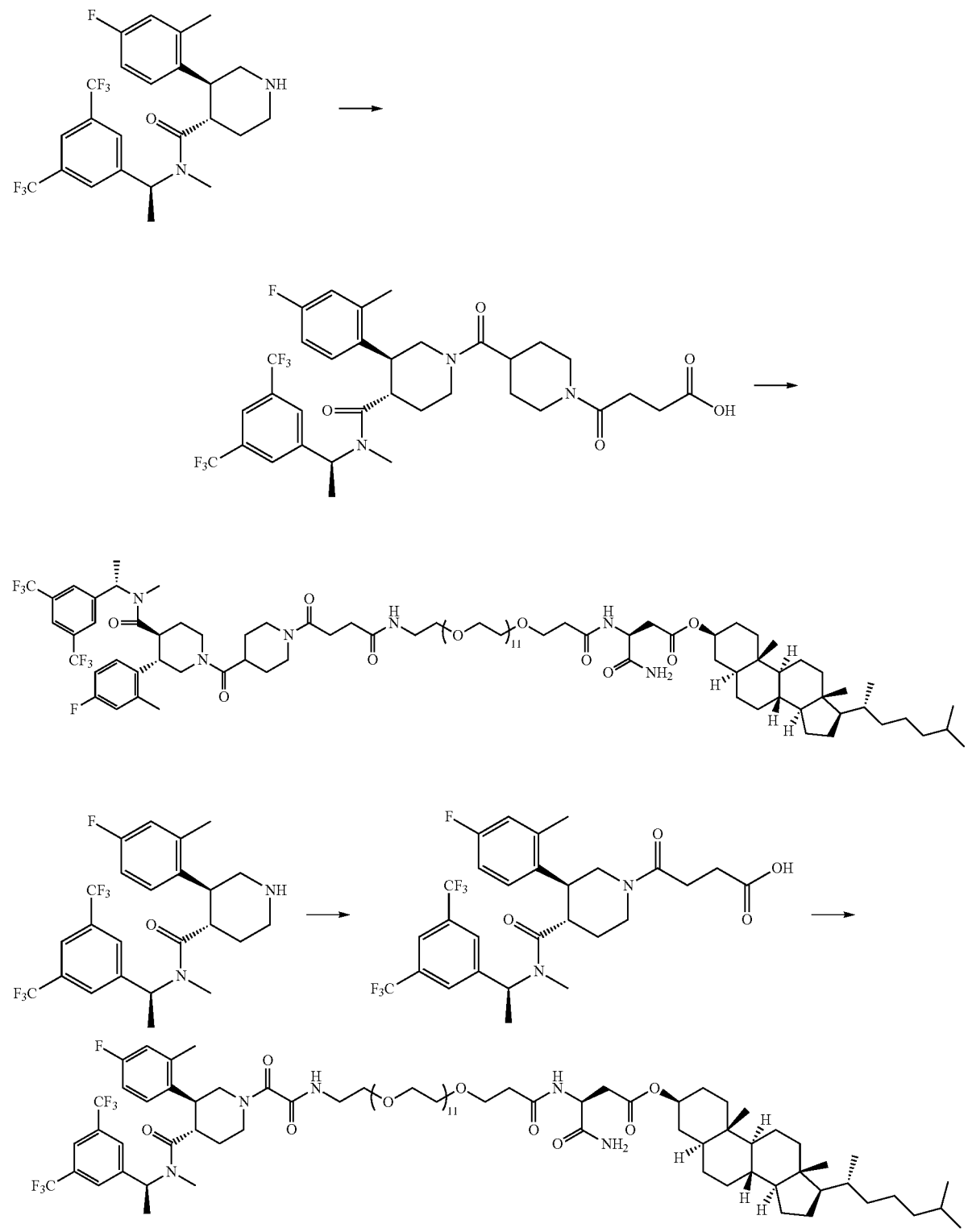

67
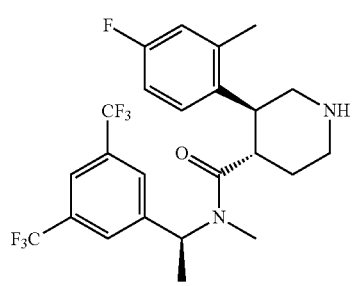 →
-continued
68
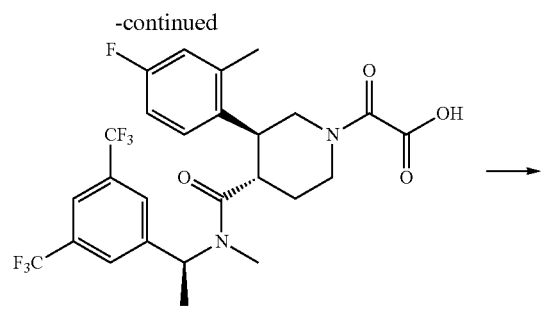 →
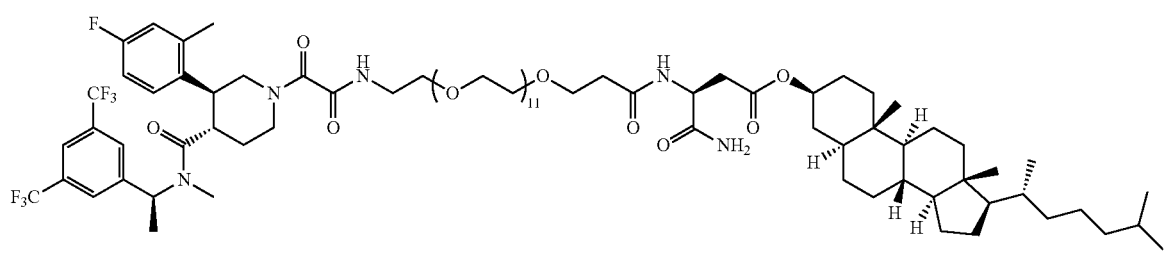
Compound D
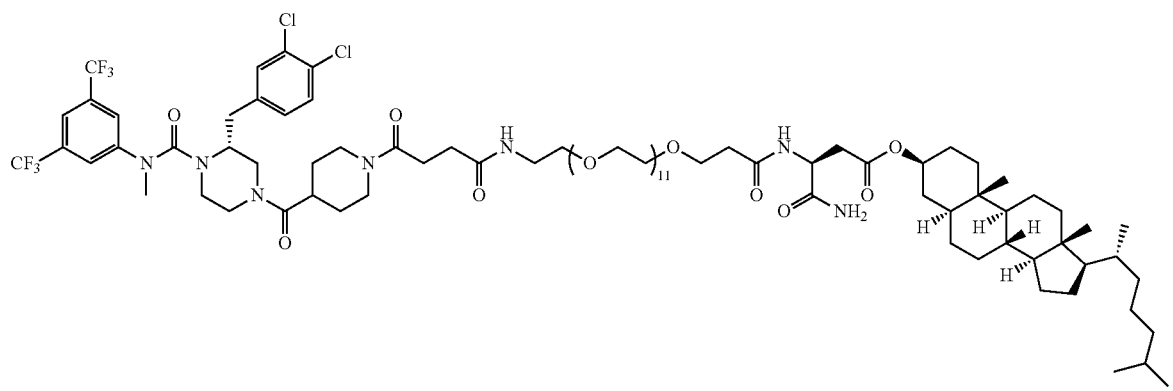
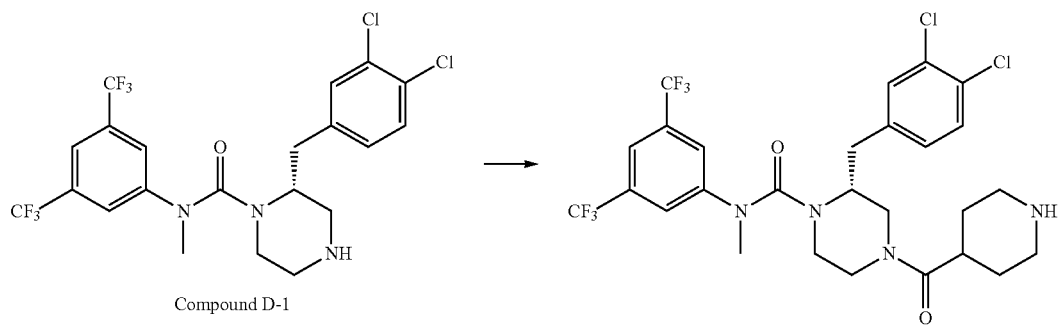
Compound D-1 → Compound D-2
↓

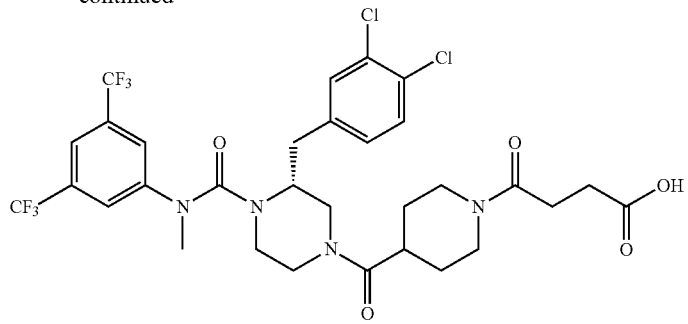

Compound D-3

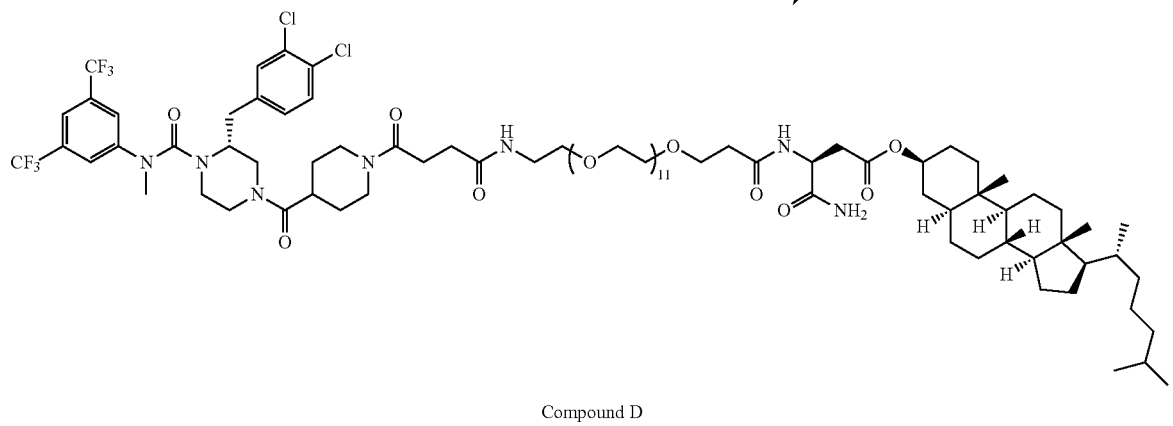

Compound D

Intermediate D-1 (1.0 g, 1.94 mmol) was coupled to N-Boc-isonipecotic acid (459 mg, 2.0 mmol) with 1-[Bis(dimethylamino)methylene]-1H-1,2,3-triazolo[4,5-b]-pyridinium 3-oxide hexafluorophosphate (779 mg, 2.05 mmol), in DMF (10 mL) with activation in situ using Et$_3$N (554 µL, 4.0 mmol) at rt overnight. The mixture was slowly diluted with water providing a ppt that was stirred for 2 h and then filtered. The filter cake was washed with copious amounts of water and dried to provide an off-white solid (1.43 g) that was immediately Boc deprotected with 4M HCl in dioxane (10 mL). Concentration after 3 h provides the deprotected intermediate D-2 as an amorphous solid (1.28 g, 99%).

Intermediate D-2 (100 mg, 0.151 mmol) was coupled to succinic anhydride (15 mg, 0.151 mmol)) in DCM (5 mL) with activation in situ using Et$_3$N (63 µL, 0.453 mmol) at rt overnight. The mixture was diluted with DCM washed with 1N HCl then brine. The organic layer was dried (MgSO$_4$), filtered, and concentrated to provide intermediate D-3 as a clear colourless resin (119 mg).

The acid D-3 (119 mg) was coupled to resin-bound NH$_2$-PEG12-Asp(OChol)-resin (300 mg) with PyBOP (2 eq) and DIPEA (6 eq) in DCM:DMF (1:1) for 2 h. The construct was then cleaved from resin using 95:5 TFA:TIPS, concentrated to a esidue that was taken up in DCM and washed with bicarbonate, dried (MgSO$_4$), filtered, and concentrated to a residue (118 mg) and purified by silica gel chromatography (MeOH:EtOAc:Et$_2$NH 10:90:1) providing Compound D as a clear colourless viscous oil (68 mg, 69%).

HRMS: m/z calculated; $C_{89}H_{137}C_2F_6N_7O_{20}$ [M+H]$^+$ 1809.9306, [M+2H]$^{2+}$ 905.4689; observed: [M+H]$^+$ 1809.9361, [M+2H]$^{2+}$ 905.4735.

Example 2: Therapeutic Targeting of Endosomal NK$_1$R

Endosomal NK$_1$R signaling generates subcellular signals that underlie neuronal activation and hyperalgesia. Painful and pro-inflammatory stimuli, including the transient receptor potential vanilloid 1 agonist capsaicin, stimulate substance P (SP) release from primary sensory nociceptors in laminae I, II of the dorsal horn, where SP stimulates NK$_1$R endocytosis in spinal neurons.

A tripartite probe based on the present invention can be synthesised comprising the lipid cholestanol or ethyl ester (negative control, no membrane anchoring), a polyethylene glycol linker and the fluorescent dye Cyanine 5 (Cy5), in addition to the tripartite compounds of the present invention.

In a first experimental approach the targeting of the tripartite compound to endosomal NK$_1$R can be studied as follows:

After incubation with HEK293 cells, Cy5-cholestanol will insert into the plasma membrane by 5 min and can be detected in endosomes by 30-60 min by which time >50% of probe will be internalized, whereas the Cy5-ethyl ester will remain in the extracellular fluid. After 4 h, Cy5-cholestanol will redistribute from the plasma membrane to Rab5a-positive early endosomes containing NK$_1$R-GFP.

A FRET assay can be used to quantitatively assess the capacity of a tripartite probe to target the $NK_1R$ in endosomes as follows:

HEK293 cells are transfected with 50 ng/well of $NK_1R$ with extracellular N-terminal Snap-Tag®. After 48 h, the cell surface $NK_1R$ is labeled with SNAP-Surface™ 549 photostable fluorescent substrate (New England Biolabs) (1 µM, 30 min, 37° C. in DMEM, 0.5% BSA). Cells were washed, recovered in DMEM for 30 min, and stimulated with substance P (SP) (10 nM, 30 min, 37° C.) to induce $NK_1R$ endocytosis. Cells are incubated with Cy5-cholestanol (200 nM, 37° C.). SNAP-549/Cy5 sensitized emission FRET is analysed by confocal microscopy using sequential excitation with Argon (514 nm)/HeNe (633 nm) lasers and emission at 570-620 nm (SNAP-549 donor) and 670-750 nm (Cy5 FRET and Cy5 acceptor) before and after addition Cy5-cholestanol. Controls include non-transfected HEK293 cells (acceptor only) and HEK293 cells not treated with Cy5-cholestanol (donor only). FRET is analysed as described and expressed as emission ratios relative to controls ($F/F_0$).

$NK_1R$ with extracellular N-terminal Snap-Tag can be expressed in HEK293 cells and cell-surface $NK_1R$ is labelled with non-membrane permeant SNAP-Surface™ 549 photostable fluorescent substrate. SP (10 nM, 30 min) evokes translocation of all detectable SNAP-549 to endosomes. SNAP-549-$NK_1R$ and Cy5-cholestanol FRET can be detected after adding Cy5-cholestanol, and increased for >75 min. Analysis of the subcellular origin of FRET can then confirm that most of the signal will be intracellular, proving probe association with endosomal $NK_1R$.

When cells are preincubated with a tripartite compound of the present invention, e.g. for 30 min, and then immediately challenged with SP, suitable antagonists will be shown to block activation of nuclear and cytosolic ERK indicating effective antagonism of cell-surface $NK_1R$. In contrast, when cells are pulse incubated with antagonists for 30 min, washed and then stimulated with SP 4 h later, the tripartite compound alone will inhibit nuclear ERK and none of the antagonists inhibit cytosolic ERK. The tripartite compound of the present invention does not affect isoprenaline-induced activation of nuclear ERK, which is mediated by the endogenous $\beta_2$-adrenergic receptor.

Thus, it can be shown by such approach that conjugation to cholestanol delivers probes to NKiR-positive early endosomes, and after pulse incubation the tripartite compounds of the present invention are capable of causing sustained and selective antagonism of the endosomal not cell-surface $NK_1R$.

In a second experimental approach, slices of rat spinal cord can be incubated with the tripartite compound of the present invention to assess whether antagonism of the endosomal $NK_1R$ blocks sustained SP-induced excitation of spinal neurons.

After incubation for 60 min, spinal cord slices are washed, incubated in antagonist-free medium for 60 min, and then challenged with SP. In vehicle- or spantide-pretreated slices, SP will cause brisk action potential discharge that is sustained after SP removal. The tripartite compound does not suppress the initial excitation, but will prevent the action potential discharge that is sustained after SP removal. Thus, an endosomally-targeted and membrane-anchored $NK_1R$ antagonist effectively blocks persistent SP-induced activation of spinal neurons and causes long-lasting analgesia.

To additionally evaluate whether antagonism of endosomal $NK_1R$ also blocks nociception, intrathecal injections of Cy5-cholestanol, spantide or the tripartite compound of the present invention can be made to mice. After 3 h, capsaicin is injected into the paw. The tripartite compound of the present invention, but not spantide or Cy5-cholestanol will markedly inhibit capsaicin-evoked hyperalgesia.

When administered 30 min after capsaicin, intrathecal spantide will have a small and transient analgesic effect, whereas the tripartite compound will cause a delayed, persistent and substantial inhibition analgesia. Cy5-cholestanol will be detected in laminae I-III neurons after 6 h, suggesting effective probe delivery. When injected intrathecally 3 hi before intraplantar formalin, the tripartite compound will markedly inhibit both phases of nocifensive behavior more effectively than spantide. When injected intrathecally 36 h after intraplantar CFA, the tripartite compound is analgesic after 4 h, and analgesia is sustained for >6 h, whereas the analgesic actions of spantide will be minor and transient.

To assess the general utility of endosomal targeting, the small molecule $NK_1R$ antagonist L733-0660 can be also tested by conjugation to cholestanol via a polyethylene glycol linker. When injected intrathecally 3 h before intraplantar capsaicin, this conjugate will show sustained analgesia for >4 h, whereas the effect of L-733,060 is only small and transient.

Thus, an endosomally-targeted and membrane-anchored $NK_1R$ antagonist effectively blocks persistent SP-induced activation of spinal neurons and causes long-lasting analgesia. Although spantide and the tripartite compound are similarly stable in human CSF for >4 h, after intrathecal injection to mice spantide will be extensively metabolized whereas the tripartite compound is stable. Endosomal targeting and retention may contribute to the in vivo stability.

The above studies can be done by use of the following techniques:

Parasagittal slices (340-400 µm) are prepared using a vibratome from the lumbar region of the rat spinal cord in ice-cold sucrose-based artificial CSF (sACSF) (mM: 100 sucrose, 63 NaCl, 2.5 KCl, 1.2 $NaH_2PO_4$, 1.2 $MgCl_2$, 25 glucose, 25 $NaHCO_3$; 95% $O_2$/5% $CO_2$). Slices are transferred to N-Methyl-D-Glucamine (NMDG)-based recovery ACSF (rACSF) (mM: 93 NMDG, 93 HCl, 2.5 KCl, 1.2 $NaH_2PO_4$, 30 $NaHCO_3$, 20 HEPES, 25 glucose, 5 Na ascorbate, 2 thiourea, 3 Na pyruvate, 10 $MgSO_4$, 0.5 $CaCl_2$; 95% $O_2$/5% $CO_2$, 15 min, 34° C.). Slices are transferred to normal ACSF (mM: 125 NaCl, 2.5 KCl, 1.25 $NaH_2PO_4$, 1.2 $MgCl_2$, 2.5 $CaCl_2$, 25 glucose, 11 $NaHCO_3$; 95% $O_2$/5% $CO_2$) containing 10 µM MK-801 (45 min, 34° C.), then maintained at RT.

Slices of rat spinal cord are transferred to a recording chamber and superfused with normal ACSF (2 ml·min$^{-1}$, 36° C.). Dodt-contrast optics are used to identify large (capacitance ≥20 pF), putative NKiR-positive neurons in lamina I based on their position, size and fusiform shape with dendrites that are restricted to lamina I. Slices are preincubated with Dy4 or Dy4 inact (both 30 µM, 0.03% DMSO) for 10 min before recording, or are preincubated with the tripartide compound of the present invention and spantide, (both 1 µM in 0.01% DMSO) for 60 min, washed and incubated in antagonist-free ACSF for a further 60 min before recording. PS2 will not be soluble in the low concentrations of DMSO required for electrophysiology. Large, NKiR-positive, presumed nociceptive lamina I neurons are visually identified as described (Imlach, W. L., et al., *Molecular Pharmacology*, 2015, 88, 460-428). Spontaneous currents are recorded in cell-attached configuration (Multiclamp 700B, Molecular Devices, Sunnyvale, Calif.), sampled at 10 kHz, high pass filtered at 1 Hz, and capacitatively coupled action potential events are analyzed using Axograph X, V 1.4.4 (Axograph). Patch electrodes (resistance 2.5-3.5 MΩ) should contain KMES-based internal solution (mM: 105 KMES, 20 NaCl, 5 HEPES, 10 BAPTA, 1.5 $MgCl_2$, 4 MgATP, 0.4 NaGTP, 0.1% biocytin; 285-295 mosmol·$l^{-1}$) to facilitate subsequent recordings of action potential properties in whole-cell configuration. Recordings are made in the presence of CNQX (6-cyano-7-nitroquinoxaline-2,3-dione) (10 µM; AMPA/kainate receptor antagonist), picrotoxin (100 µM; $GABA_A$ receptor antagonist), strychnine (0. µM; glycine and acetylcholine receptor antagonist), and AP5 ((2R)-amino-5-phosphonovaleric acid; (2R)-amino-5-phosphonopentanoate) (100 µM; NMDA receptor antagonist) to minimize presynaptic influences on action potential properties. Slices are then challenged by superfusion with SP (1 µM) for 2 min. Recordings are sampled at 10 kHz and filtered with a high pass filter at 1 Hz and firing rate is measured in two-minute interval bins. At the end of each cell-attached recording, whole-cell recordings are made in current-clamp mode to confirm retention of normal action potential firing. Data are only included in the analysis if cells have action potential amplitudes that are ≥50 mV above threshold to ensure viable neurons are included. Cells are filled with biocytin and sections are processed to confirm $NK_1R$ expression by immunofluorescence. The firing rate for each cell is normalized to the response at the 2 min time point, which will not be significantly different between groups. The firing time is determined as the duration of the response to last action potential. To assess synaptic transmission, whole-cell configuration recordings are made under control conditions or after exposure to Dy4 or Dy4 inact; a bipolar stimulating electrode is placed at the dorsal root entry zone, and electrically-evoked excitatory postsynaptic currents are recorded as described (Imlach, W. L., et al., *Molecular Pharmacology*, 2015, 88, 460-428). To additionally assess $NK_1R$ endocytosis, spinal cord slices (400 µm) are incubated with SP (1 µM, 5 min), fixed in PFA (4 h, RT), cryoprotected, and are processed to localize the $NK_1R$.

Mice are acclimatized to the experimental apparatus and environment for 1-2 h on 2 successive days before experiments. Mechanical hyperalgesia is assessed by paw withdrawal to stimulation of the plantar surface of the hind-paw with graded von Frey filaments. On the day before the study, von Frey scores are measured in triplicate to establish a baseline for each animal. To assess edema of the paw, hindpaw thickness is measured using digital calipers before and after treatments. For intraplantar injections, mice are sedated (5% isoflurane). Capsaicin (5 µg), Complete Freund's Adjuvant (CFA, 2 mg/ml), or vehicle (capsaicin, 20% ethanol, 10% Tween 80, 70% saline; CFA, saline) is injected subcutaneously into the plantar surface of the left hindpaw (10 µl). von Frey scores (left and right paws) and paw thickness (left paw) are measured for 30-240 min after capsaicin, and 36-40 h after injection of CFA. Results are expressed as percent pre-injected values. For assessment of nocifensive behavior, mice are sedated and formalin (4%, 10 µl) is injected subcutaneously into the plantar surface of the left hindpaw. Mice are placed in a Perspex container and nocifensive behavior (flinching, licking, biting of the injected paw) is recorded for 60 min. The total number of nocifensive events is subdivided into acute (I, 0-10 min) and tonic (II, 10-60 min) phases. At the end of experiments, mice are transcardially perfused with PBS and PFA, and the spinal cord is removed and processed to localize the $NK_1R$ by immunofluorescence, as described for rats. Investigators are unaware of test agents.

Intrathecal injections (5 µl, L3/L4) are made into conscious mice. Dy4, Dy4 inact, PS2, PS2 inact (all 50 µM), SR-140333 (15 µM), SM-19712 (8 mM), U0126 (100 µM), or vehicle (1% DMSO/saline) is injected intrathecally 30 min before intra-plantar injection of capsaicin or formalin, or 36 h after CFA. Spantide (50 µM), the tripartite compound (50 µM), L-733,060 (100 nM), or Cy5-cholestanol (10 µM) is injected intrathecally 3 h before or 30 min after intraplantar injection of capsaicin, 3 h before formalin, or 36 h after CFA.

Example 3: Methods for Preparing Compounds of the General Formula (Ie)

The following examples are representative of the present invention, and provide detailed methods for preparing exemplary compounds of the present invention.

General Experimental Details

Fmoc-PAL-PEG-PS resin for SPPS was obtained from Applied Biosciences. PEG amino acids (Fmoc-PEG3-OH and Fmoc-PEG4-OH) were obtained from Polypeptide Group (France). Fmoc-Asp(OChol)-OH and Fmoc-Asp(OEt)-OH were synthesized from commercially-available Fmoc-Asp-Ot-Bu using standard chemistry (side-chain esterification, followed by acid-deprotection of the C-terminus). All other Fmoc amino acids (with suitable protecting groups) were obtained from Chem-Impex or Auspep. Coupling agents (HBTU, HCTU) and solvents were used as received.

Liquid chromatography-mass spectrometry (LC-MS) data was obtained using a Shimadzu LCMS-2020 spectrometer equipped with a Phenomenex Luna C8 (2) 3 µm analytical (100 Å, 100×2 mm) eluted with mixtures of buffers A and B consisting of 0.05% TFA/$H_2O$ and 0.05% TFA/ACN, respectively. Preparative high-pressure liquid chromatography (HPLC) was carried out using a Waters Prep LC system consisting of a solvent pump, system controller and UV absorbance detector, using a Phenomenex Luna C8 (2) 10 µm column (10 Å, 50×21.2 mm) for larger-scale preparative purifications and a Phenomenex Luna C8 (2) 5 µm column (100 Å, 250×10 mm) for smaller-scale semi-preparative purifications. All separations used buffers A and B consisting of 0.1% TFA/$H_2O$ and 0.1% TFA/ACN, respectively as solvent.

General SPPS Methods:

Automated SPPS was carried out using a Rainin PS3 instrument by standard methods, using 20% v/v piperidine in DMF as deprotection mixture and 7% v/v DIPEA in DMF as activating mixture. Fmoc-protected amino acids (3 equivalents relative to resin loading) were pre-mixed in vials with HCTU (3 eq) as a coupling agent and standard coupling times of 50 minutes were used.

Manual SPPS was carried out in a 5 mL filtration column that could be enclosed within a 250 mL round-bottomed flask and agitated on a standard rotary evaporator. For N-Fmoc-deprotection, 20% v/v piperidine in DMF (2 mL) was added to the resin and the mixture agitated for 15 minutes. The deprotection mixture was then removed by filtration and the resin washed with DMF (5×2 mL). This process was repeated a total of three times to ensure complete deprotection, with the resin washed with DMF (5×2 mL), MeOH (5×2 mL) and $CH_2Cl_2$ (5×2 mL) on the final occasion. For amino acid coupling, a solution of the appropriate amino acid (3 equivalents), HBTU or HCTU (3 eq) and DIPEA (3.5 eq) in DMF (2 mL) was added to the deprotected resin and the mixture agitated for 15-20 hours to ensure complete deprotection. The coupling mixture was then removed by filtration and the resin washed with DMF (5×2 mL), MeOH (5×2 mL) and $CH_2Cl_2$ (5×2 mL) and dried under reduced pressure.

After assembly of the peptide on resin was completed, cleavage from the solid support was achieved by exposure of the resin to a 95:2.5:2.5 v/v mixture of TFA/TIPS/$H_2O$ (3 mL) for 2-3 hours with occasional agitation. For syntheses involving amino acids with side-chain protecting groups, 92.5:2.5:2.5:2.5 v/v mixture of TFA/TIPS/$H_2O$/EDT was used instead to prevent unwanted side-reactions. The resin was then filtered off and the TFA solution concentrated under a stream of $N_2$ to give the crude peptide.

Synthesis of Exemplified Compounds

Compound 1

The protected linear peptide $^D$Arg-Pro-Lys-Pro-Gln-Gln-$^D$Trp-Phe-$^D$Trp-Leu-Leu-$NH_2$ (Spantide I) was synthesised by automated SPPS as described above starting with N-deprotection of Fmoc-PAL-PEG-PS resin (278 mg, 0.18 mmol/g, 50.0 µmol). After the final N-deprotection step, a portion of the material was cleaved from resin to give a crude residue that was suspended in a 1:1 mixture of ACN/$H_2O$ containing 0.1% TFA to ensure complete side-chain deprotection. Purification of this crude product by semi-preparative HPLC (20-90% Buffer B over 35 minutes) gave Spantide I, which was confirmed by mass spectrometry, m/z calculated: 749.5 for $C_{75}H_{110}N_{20}O_{13}$ [M+2H$^+$]; observed: m/z 749.4.

Next, a portion of the N-deprotected resin bound compound (375 mg, 50.0 µmol) was transferred a 5 mL filtration column and subjected to manual SPPS with Fmoc-PEG4-OH, Fmoc-PEG3-OH, Fmoc-PEG4-OH and Fmoc-Asp(OChol)-OH, respectively. Following the final N-deprotection step, the N-terminus of the peptide was capped by exposure of the resin to a solution of DIPEA (100 µL) and acetic anhydride (1.5 mL) in DMF (1.5 mL) with continuous agitation for two hours. The resin was then washed in the usual way and the peptide cleaved from resin to give the crude product. Purification by preparative HPLC (50-100% Buffer B over 35 minutes) gave Compound 1 (5.5 mg).

Compound 1 was confirmed by mass spectrometry, m/z calculated: 908.9 for $C_{139}H_{223}N_{24}O_{31}$ [M+3H$^+$]; observed: m/z 908.2; m/z calculated: 1362.7 for $C_{139}H_{223}N_{24}O_{31}$ [M+2H$^+$]; observed: m/z 1361.8.

Compound 2

Synthesis was carried out by manual SPPS as described above, starting with Fmoc-PAL-PEG-PS resin (loading 0.17 mmol/g from Life Technologies) on a 0.025 mmol scale (147 mg of resin). The coupling/deprotection cycle was repeated a total of 4 times, using Fmoc-Asp(OChol)-OH, Fmoc-PEG4-OH, Fmoc-PEG3-OH and Fmoc-PEG4-OH, respectively.

After the final N-deprotection step, half of the resin-bound peptide (85.7 mg, 12.5 µmol assuming complete conversion) was coupled with 3 mol eq. of 8-bromooctanoic acid, 3 mol eq. of HCTU and 5 mol eq. of DIPEA in DMF (3 mL) with constant agitation for 45 minutes, at which point the TNBS test showed a positive result. The coupling solution was then filtered off and the resin washed with DMF, MeOH and DCM (5×5 mL each) and dried under vacuum. Finally, the bromo-terminated resin bound compound was reacted with the $NK_1R$ antagonist L-733,060-HCl (0.8 mol eq.) in a solution of tetra-n-butylammonium iodide (TBAI, 0.5 mol eq.) and DIPEA (5 mol eq.) of over the course of 3 days. The coupling solution was then filtered off and the resin washed with DMF, MeOH and DCM (5×5 mL each) and dried under vacuum. The product was cleaved from the resin using 2 mL of a mixture of TFA/TIPS/$H_2O$ (95:2.5:2.5) for 1.5 h, after which time the resin was filtered, washed with 2 mL of TFA, and the solvent removed under a stream of nitrogen. The crude residue was then taken up in a mixture of milli-Q water (1 mL) and acetonitrile (0.5 mL) and subjected to RP-HPLC purification. Compound 2 was confirmed as having the correct molecular weight by ESI-MS analysis: m/z calculated: 864.53 for $C_{90}H_{144}F_6N_6O_{19}$ [M+2H]$^{2+}$; observed: m/z 864.70.

Compound 3

$NK_1R$ agonist GR73632 [Ava-Phe-Phe-Pro-N-MeLeu-Met-$NH_2$] was prepared by automated SPPS starting with N-deprotection of Fmoc-PAL-PEG-PS resin as described above. After final N-deprotection, a portion of the material was cleaved from the resin using TFA solution (95:2.5:2.5 TFA:TIPS:H2O) to give the desired agonist peptide. The product was confirmed by mass spectrometry: m/z 766.4, calcd for $C_{40}H_{59}N_7O_6S$ [M+H$^+$] m/z 766.4.

Compound 3 was derived from a portion of resin-bound GR73632. The N-deprotected GR73632 resin was subjected to manual SPPS using Fmoc-PEG4-OH, Fmoc-PEG3-OH, Fmoc-PEG4-OH and Fmoc-Asp(OChol)-OH as the amino acids. Following final deprotection, the N-terminus of the peptide was capped by exposure to DIPEA and $Ac_2O$ in DMF for 2 h. The construct was cleaved from the resin as above and purified by repeated HPLC. Compound 3: m/z 996.6, calcd for $C_{104}H_{173}N_{11}O_{24}S$ [M+2H$^+$] m/z 996.1.

Compound 4

Synthesis of the protected linear peptide VTHRLAGLLSRSGGVVKDNFVPTNVGSEAF-$NH_2$ (CGRP$_{8-37}$) was carried out via manual SPPS as explained above. Synthesis started with NovaSyn®TG$^R$ R resin (loading 0.18 mmol/g) on a 0.18 mmol scale (1 g of resin). A small portion of the completed CGRP$_{8-37}$ peptide on resin (100 mg) was cleaved, filtered and washed with 2 mL of the cleavage solution, and solvent was removed under a stream of nitrogen. The crude peptide was subjected to RP-HPLC purification providing CGRP$_{8-37}$ as a white amorphous solid in a yield of 7 mg. The compound was confirmed as having the correct molecular weight by ESI-MS analysis. m/z (monoisotopic) calculated; $C_{139}H_{230}N_{44}O_{38}$ [M+2H]$^{2+}$ 1563.83, [M+3H]$^{3+}$ 1042.89, [M+4H]$^{4+}$782.42, [M+5H]$^{5+}$ 626.14; observed: [M+2H]$^{2+}$ 1563.85, [M+3H]$^{3+}$ 1043.00, [M+4H]$^{4+}$782.55, [M+5H]$^{5+}$626.30.

A portion of the completed CGRP$_{8-37}$ peptide on resin (100 mg; 0.018 mmol assumed for 100 mg of peptide bound resin) was sequentially deprotected and coupled with N-Fmoc-Peg$_{12}$-acid, and Fmoc-Asp(OCholestanol)-OH, respectively. The resin bound compound was then treated with acetic anhydride (3 mol eq.) in DMF activated with DIPEA (6 mol eq.) for 20 min. The compound was then cleaved using 2 mL of a mixture of TFA/TES/$H_2O$ (95:2.5:2.5) for 3 h in which the protecting groups were simultaneously removed. The crude compound was taken up in milli-Q water and subjected to RP-HPLC purification providing Compound 4 as white amorphous powder in a yield of 1.3 mg. The compound was confirmed as having the correct molecular weight by ESI-MS analysis. Compound 4, m/z (monoisotopic) calculated: $C_{199}H_{336}N_{46}O_{55}$ $[M+3H]^{3+}$ 1418.84, $[M+4H]^{4+}$1064.38, $[M+5H]^{5+}$851.71, $[M+6H]^{6+}$ 709.92; observed: $[M+3H]^{3+}$ 1418.85, $[M+4H]^{4+}$1064.45, $[M+5H]^{5+}$851.80, $[M+6H]^{6+}$710.05.

Example 4: $NK_1R$ Endosomal Trafficking

Bioluminescence Resonance Energy Transfer (BRET) was employed to quantitatively assess the proximity of the $NK_1R$ to key regulators of GPCR trafficking (βarrs), and resident proteins of plasma (KRas) and early endosomal (Rab5a) membranes in HEK293 cells (FIG. 1A). Substance P (SP, 1, 10 nM) stimulated BRET between $NK_1R$-RLuc8 and βarr1-YFP and βarr2-YFP (FIG. 1B, C). SP decreased $NK_1R$-RLuc8/KRas-Venus BRET and concomitantly increased $NK_1R$-RLuc8/Rab5a-Venus BRET (FIG. 1D), consistent with $NK_1R$ endocytosis. Endocytosis was dynamin- and clathrin-dependent because the dynamin inhibitor Dyngo 4a (Dy4), the clathrin inhibitor PitStop 2 (PS2) and expression of dominant negative dynamin K44E all blocked the decrease in $NK_1R$-RLuc8/KRas-Venus BRET and the increase in $NK_1R$-RLuc8/Rab5a-Venus BRET (FIG. 1E, F). Dy4 inactive (Dy4 inact), PS2 inactive (PS2 inact), and wild-type (WT) dynamin had no effect. Dynamin K44E increased the $NK_1R$-RLuc8/βarr1-YFP and βarr2-YFP BRET, suggesting that endocytosis initiates $NK_1R$/βarr dissociation.

$NK_1R$ was localised by studying trafficking of Alexa568-SP in HEK-$NK_1R$ cells. In vehicle-treated cells (Veh), Alexa568-SP bound to the plasma membrane receptor at 4° C., and completely redistributed to endosomes after 30 min at 37° C. Dy4 and PS2, but not inactive controls, caused retention of Alexa568-SP in vesicles close to the plasma membrane (data not shown). Thus, SP promotes $NK_1R$ association with βarrs, and induces clathrin- and dynamin-dependent endocytosis of the $NK_1R$.

Example 5: $NK_1R$ Endosomal Signaling

To study the link between $NK_1R$ trafficking and signaling, the $NK_1R$ and Förster Resonance Energy Transfer (FRET) biosensors targeted to detect activated ERK in the cytosol (CytoEKAR) or nucleus (NucEKAR, FIG. 2A), activated PKC at the plasma membrane (pmCKAR) or in the cytosol (CytoCKAR, FIG. 2C), and cAMP at the plasma membrane (pmEpac2) or in the cytosol (CytoEpac2, FIG. 2E) were expressed in HEK293 cells. SP (1 nM) rapidly and transiently activated cytosolic ERK (not shown) and caused a delayed and sustained activation of nuclear ERK (FIG. 2B). SP did not affect plasma membrane PKC activity (not shown) but caused a rapid and sustained increase in cytosolic PKC activity (FIG. 2D). SP transiently increased plasma membrane cAMP (not shown) and caused a sustained increase in cytosolic cAMP (FIG. 2F). PS2 and Dy4, but not inactive controls, abolished SP stimulation of nuclear ERK (FIG. 2B), cytosolic PKC (FIG. 2D) and cytosolic cAMP (FIG. 2F). PS2 and Dy4 did not suppress SP activation of cytosolic ERK or plasma membrane cAMP, but caused both responses to become sustained. PS2 and Dy4 amplified plasma membrane PKC activity. Dynamin WT magnified SP activation of nuclear ERK, whereas dynamin K44E abolished activation of nuclear ERK (FIG. 2G). Dynamin K44E did not block activation of cytosolic ERK but caused the response to become sustained. Dynamin and clathrin siRNA inhibited expression and prevented SP activation of nuclear ERK (FIG. 2H). Thus, clathrin- and dynamin-dependent $NK_1R$ endocytosis is required for activation of nuclear ERK, which also depends on βarrs and for activation of cytosolic PKC and cAMP.

Since PKC and cAMP signaling via GPCRs depends on heterotrimeric G-proteins, the capacity of SP to activate G-proteins in endosomes of HEK293 cells was examined. BRET was used to determine the proximity of the $NK_1R$ and $G\alpha_q$ to Rab5a and $G\gamma_2$. SP (0.1-10 nM) decreased $NK_1R$-RLuc8/KRas-Venus BRET, which mirrored the increase in $NK_1R$-RLuc8/Rab5a-Venus BRET (FIG. 3A, B). SP decreased $G\alpha_q$-RLuc8/$G\gamma_2$-Venus BRET, which was maintained for 15 min (FIG. 3C), and increased $G\alpha_q$-RLuc8/Rab5a-Venus BRET at 15 min (FIG. 3D). Immunofluorescence and super-resolution microscopy were used to determine whether $G\alpha_q$ co-localized with the $NK_1R$ at the plasma membrane or in endosomes of HEK-$NK_1R$ cells. After incubation with SP (10 nM) at 4° C., $NK_1R$ immunoreactivity ($NK_1R$-IR) and $G\alpha_q$-IR were colocalized at the plasma membrane. After washing and warming to 37° C. for 15 min, $NK_1R$-IR and $G\alpha_q$-IR were co-localized with early endosomal antigen 1 (EEA1) (data not shown). Thus, SP activates this G protein complex by its dissociation and recruits $G\alpha_q$ to endosomes.

The $G\alpha_q$ inhibitor UBO-QIC prevented SP activation of nuclear ERK (FIG. 3E), which also depends on βarrs and PKC and is independent of epidermal growth factor receptor transactivation. UBO-QIC, the PLC inhibitor U73122 and the $Ca^{2+}$ chelator EGTA prevented activation of cytosolic PKC (FIG. 3F), consistent with activation of the $G\alpha_q$, PLC and $Ca^{2+}$-dependent PKC pathway. UBO-QIC, the PKC inhibitor GF109203X and EGTA, but not the $G\alpha_q$ inhibitor NF449, prevented SP generation of cytosolic cAMP (FIG. 3G), which implicates $G\alpha_q$-mediated activation of $Ca^{2+}$-dependent PKC in the generation of cAMP. UBO-QIC did not affect $NK_1R$ endocytosis. These results suggest that activated $NK_1R$ and $G\alpha_q$ translocate to endosomes, where $G\alpha_q$ generates nuclear ERK and cytosolic PKC and cAMP.

Example 6: $NK_1R$ Endocytosis and Activation of Spinal Neurons

Painful and proinflammatory stimuli, including capsaicin (transient receptor potential vanilloid 1 agonist), trigger SP release from primary sensory nociceptors in laminae I, II of the dorsal horn, where SP stimulates $NK_1R$ endocytosis in spinal neurons[10-11]. SP causes persistent NKiR-dependent excitation of spinal neurons[20]. To evaluate whether $NK_1R$ endosomal signaling mediates this sustained activation, cell-attached patch clamp recordings were made from NKiR-positive neurons in lamina I of the dorsal horn in slices of rat spinal cord. SP (1 μM, 5 min) stimulated $NK_1R$ endocytosis, that was prevented by Dy4 (FIG. 4A). SP (1 μM, 2 min) triggered a rapid onset firing of action potentials that was sustained after washout (FIG. 4B, C, D). Dy4, but not Dy4 inact, did not affect the initial excitation, but prevented the sustained action potential discharge that persisted after SP removal (FIG. 6B, C, D) and inhibited $NK_1R$ endocytosis. These findings support a role for $NK_1R$ endocytosis in persistent neuronal excitation.

Dy4 did not affect glutaminergic primary afferent synaptic transmission or synaptic rundown in slices of rat spinal cord (not shown). PS2 and Dy4 did not affect basal or capsaicin-stimulated release of SP-IR and CGRP-IR from segments of mouse dorsal spinal cord.

Example 7: $NK_1R$ Endocytosis and Pain Transmission

To determine the involvement of dynamin and clathrin in $NK_1R$ endocytosis in vivo, Sprague-Dawley rats (male, 3-8 weeks) were injected intrathecally (L3/L4) with vehicle (Veh), Dy4, Dy4 inact, PS2 or PS2 inact. Intraplantar injections of vehicle or capsaicin were made after 30 min into the left hind paw. The spinal cord was collected 10 min later for localization of the $NK_1R$. In controls (intrathecal, intraplantar vehicle), $NK_1R$-IR was mostly at the plasma membrane of the soma and neurites of lamina I neurons (80.7±1.6% of total $NK_1R$-IR within 0.5 m of the soma plasma membrane). Capsaicin stimulated $NK_1R$ endocytosis (42.1±5.6% $NK_1R$-IR at plasma membrane, P<0.001 to control; FIG. 4A). Dy4 or PS2, but not Dy4 inact or PS2 inact, inhibited capsaicin-stimulated $NK_1R$ endocytosis (% membrane: Dy4 59.6±0.2, Dy4 inact 49.9±0.8, P<0.001; PS2 69.0±1.1, PS2 inact 51.9±1.3, P<0.05; FIG. 4A).

Figure 5:
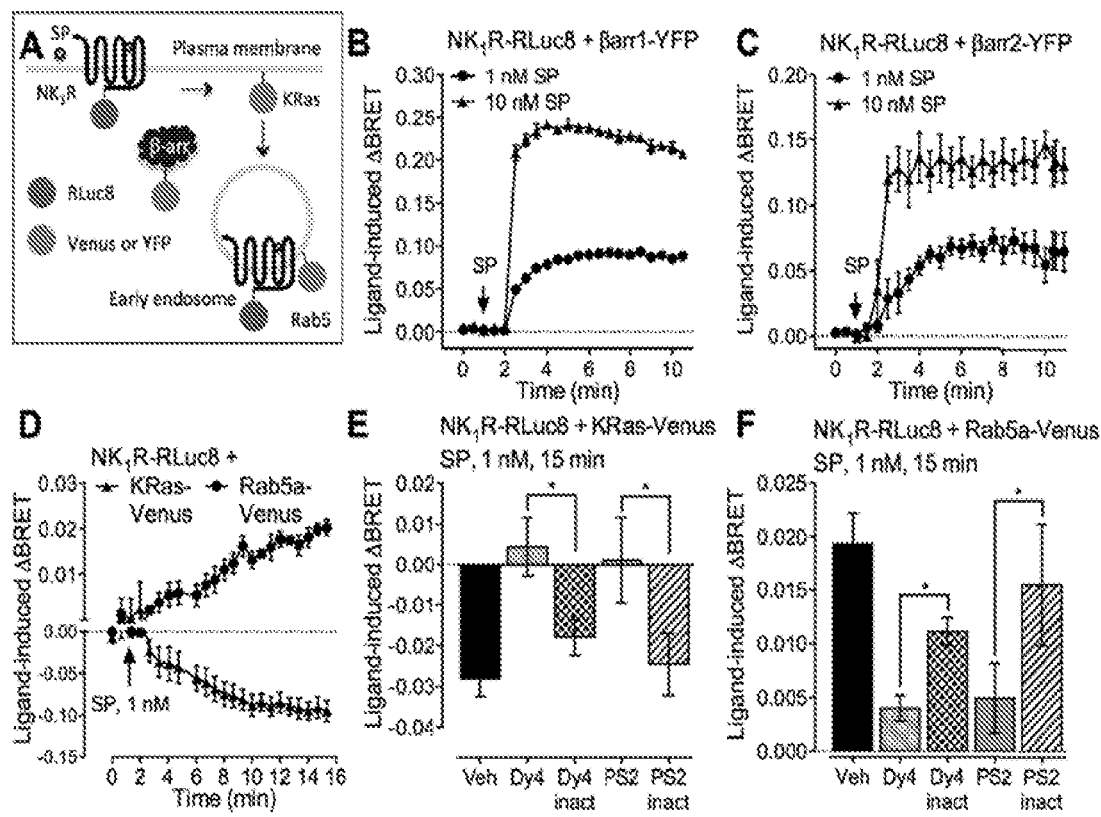
FIG. 5: Graphical representations of $NK_1R$ subcellular trafficking. A. BRET analysis of the proximity between $NK_1R$-RLuc8, β-arr1/2-YFP, KRas-Venus or Rab5a-Venus. B-C. SP-induced BRET in HEK293 cells between $NK_1R$-RLuc8 and β-arr1-YFP (B) or 3-arr2-YFP (C). D-F. SP-induced BRET in HEK293 cells between $NK_1R$-RLuc8 and KRas-Venus (D, E) or Rab5a-Venus (D, F). E, F show effects of endocytic inhibitors. *P<0.05, ***P<0.001. Triplicate observations, n>3 experiments.

Painful peripheral stimuli activate ERK in NKiR-expressing spinal neurons, which coincides with receptor endocytosis and contributes to hyperalgesia. Intraplantar capsaicin stimulated ERK phosphorylation in lamina I dorsal horn neurons (FIG. 5B). Dy4 or PS2, but not the inactive analogues, prevented capsaicin-evoked activation of spinal ERK. Thus, capsaicin stimulates clathrin- and dynamin-dependent $NK_1R$ endocytosis and ERK activation in spinal neurons in vivo.

Figure 6:
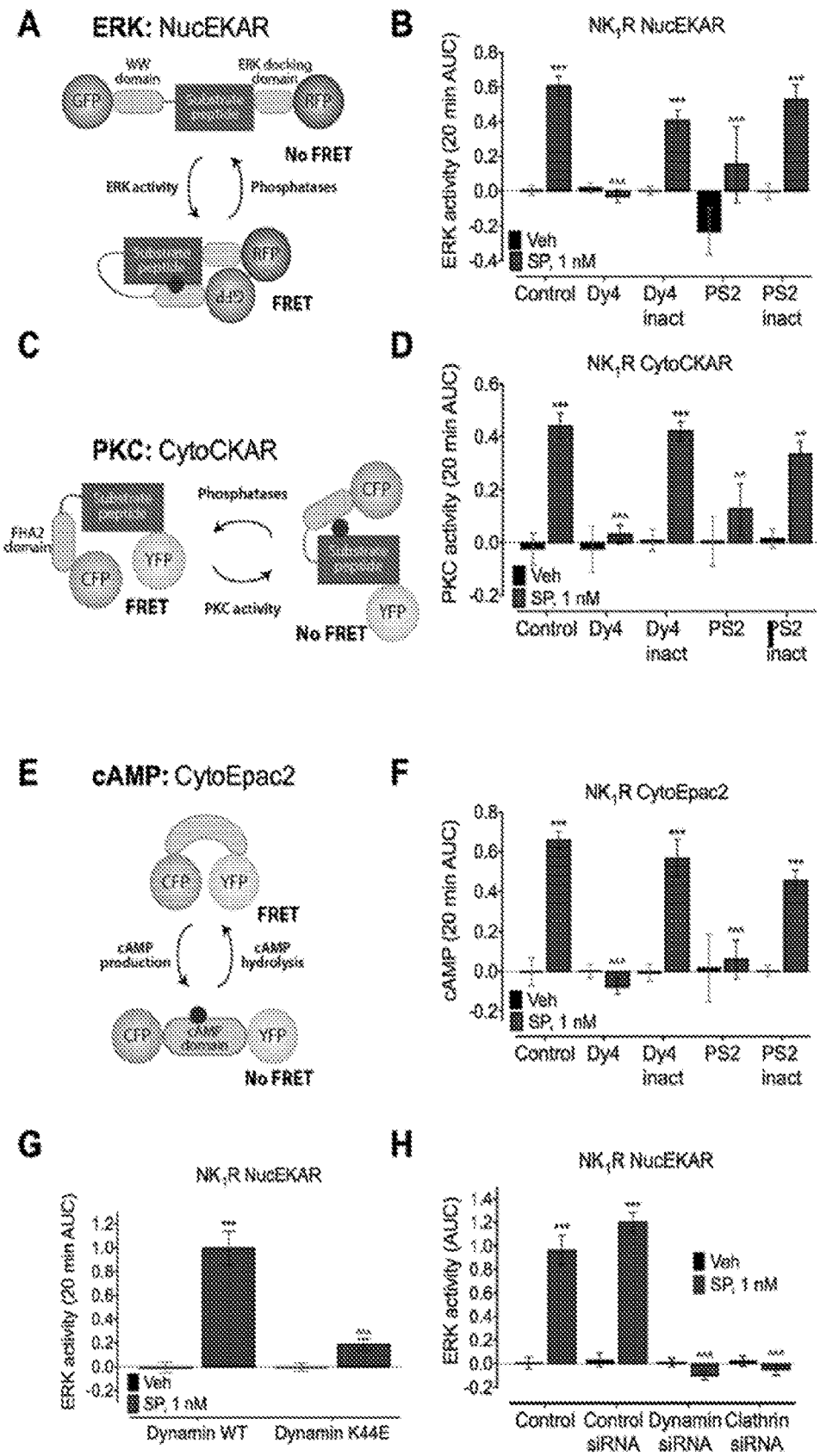
FIG. 6: Graphical representations of $NK_1R$ subcellular signaling A, C, E. FRET biosensors for detection of activated ERK in the nucleus (NucEKAR), activated PKC in the cytosol (CytoCKAR), and cAMP in the cytosol (CytoEpac2). SP-induced FRET in NKiR-expressing HEK293 cells using biosensors for nuclear ERK (B, G, H), cytosolic PKC (D), and cytosolic cAMP (F). Effects of endocytic inhibitors are shown. B, D, E, G, H show area under curve (AUC). P<0.01, *P<0.001 SP to vehicle; ^^P<0.01, ^^^P<0.001 SP control to SP with Dy4, PS2, dynamin K44E, dynamin siRNA, or clathrin siRNA. n=30-170 cells.

To evaluate the importance of $NK_1R$, clathrin and dynamin, mice (C57BL/6, male, 6-10 weeks) were injected intrathecally (L3/L4) with vehicle, $NK_1R$ antagonist SR140, 333, Dy4, Dy4 inact, PS2 or PS2 inact. After 30 min, intraplantar injections of vehicle or capsaicin were made into the left hindpaw. Mechanical hyperalgesia was measured by stimulation of the plantar surface of the left and right paws with von Frey filaments, and inflammatory edema was assessed by measuring left paw thickness with calipers. In vehicle (intrathecal)-treated mice, capsaicin caused mechanical hyperalgesia and edema of the left paw. SR140,333, Dy4 and PS2, but not Dy4 inact and PS2 inact, inhibited hyperalgesia (FIG. 6A, B). Edema was unaffected, confirming their local action in the spinal cord (FIG. 6C). Dy4 and PS2 did not affect paw withdrawal responses of the uninjected right hind paw or rotarod latency, suggesting normal motor behaviour (FIG. 5D Intrathecal injection of dynamin-1 siRNA reduced spinal dynamin-1 levels, and inhibited capsaicin-evoked hyperalgesia at 24 h and 48 h (FIG. 6E, F). Intrathecal βarr1+2 siRNA reduced spinal levels of βarr1 and 2 and also inhibited capsaicin-evoked hyperalgesia at 36 h (FIG. 5G-H). siRNAs did not affect paw withdrawal responses of the uninjected right hind paw (not shown). Intrathecal MEK inhibitor U0126 inhibited capsaicin-evoked hyperalgesia (FIG. 6I). Intrathecal SM-19712, an inhibitor of endothelin-converting enzyme-1 that prevents $NK_1R$ recycling and resensitization, had no effect on hyperalgesia, suggesting that the analgesic action of endocytic inhibitors is not due to inhibited resensitization. Intrathecal Dy4 and PS2 inhibited both phases of nocifensive behavior in mice evoked by intraplantar injection of formalin (FIG. 6J, K). Intraplantar injection of complete Freund's adjuvant (CFA) caused sustained mechanical hyperalgesia in mice, that was partially reversed by intrathecal Dy4 and PS2 within 1-5 h (FIG. 6L). Intraplantar capsaicin, formalin and CFA all evoked $NK_1R$ endocytosis in neurons of mouse dorsal horn, that was inhibited by intrathecal Dy4 (data not shown).

These results are consistent with the hypothesis that $NK_1R$ endocytosis and resultant ERK activation contribute to hyperalgesia, since dynamin, clathrin, βarr and MEK inhibitors were analgesic. The analgesic actions of endocytic inhibitors are unlikely due to disrupted neuropeptide release, synaptic transmission or motor coordination, which were unaffected.

Example 8: Therapeutic Targeting of Endosomal $NK_1R$

Figure 7:
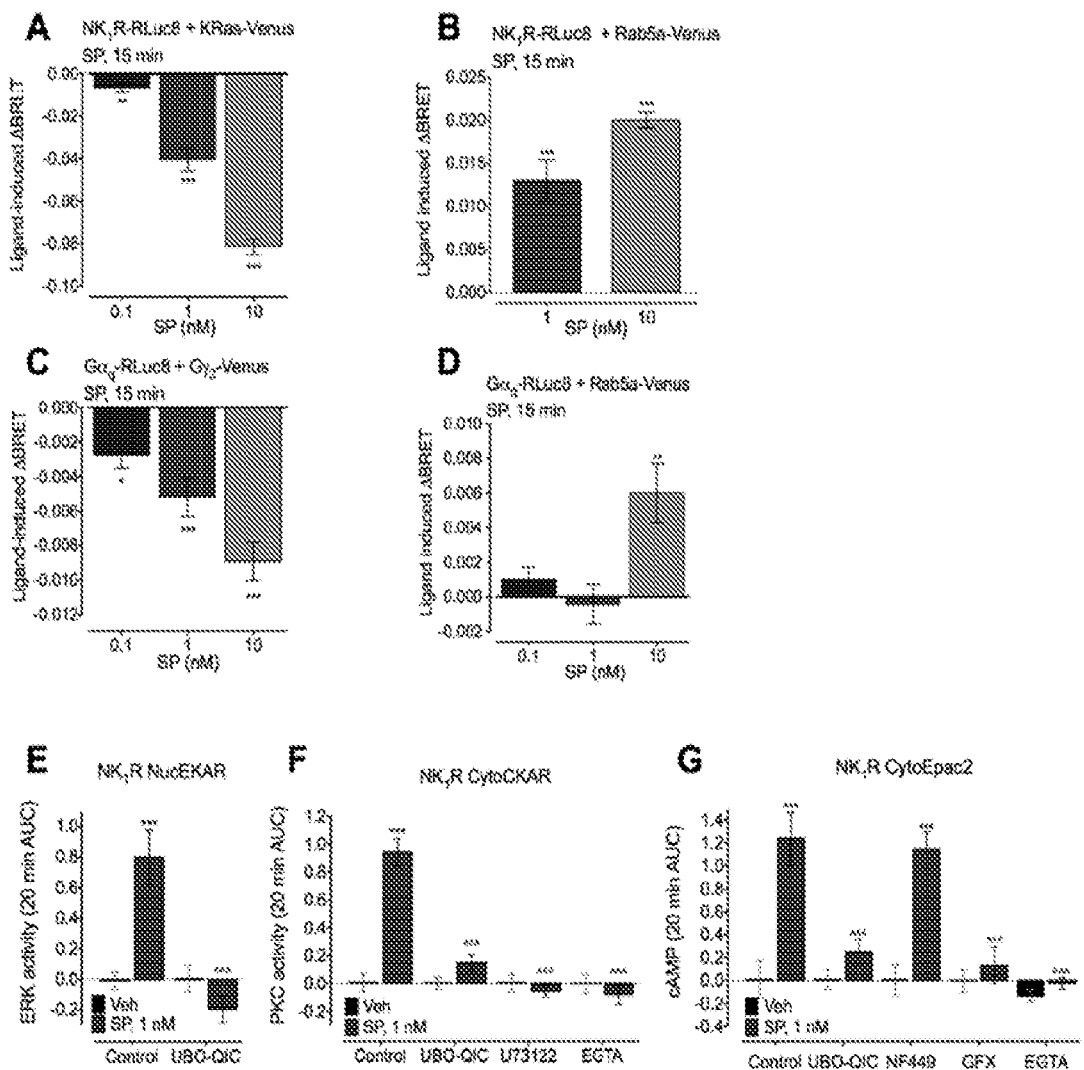
FIG. 7: Graphical representations of G-protein-dependent NK$_1$R signaling. A-D. SP-induced BRET in HEK293 cells between NK$_1$R-RLuc8 and KRas-Venus (A), NK$_1$R-RLuc8 and Rab5a-Venus (B), G$\alpha_q$-RLuc8 and G$\gamma_2$-Venus (C), and G$\alpha_q$-RLuc8 and Rab5a-Venus (D) after 15 min. *P<0.05, P<0.01, *P<0.001 to baseline. Triplicate observations, n>3 experiments. E-G. SP-induced FRET in NKiR-expressing HEK293 cells for nuclear ERK (E), cytosolic PKC (F), and cytosolic cAMP (G). ***P<0.001 SP to vehicle; ^^^P<0.001 SP control to SP with inhibitor. n=35-67 cells.

The finding that the endosomal $NK_1R$ generates compartmentalized signals that underlie neuronal activation and sustained hyperalgesia suggested that antagonism of the $NK_1R$ in endosomes may provide an effective treatment for pain. To explore the usefulness of this approach, a tripartite probe was synthesised comprising the lipid cholestanol or ethyl ester (control, no membrane anchoring), a polyethylene glycol linker and the fluorescent dye Cyanine 5 (Cy5), in addition to the compounds of the invention. After incubation with HEK293 cells, Cy5-cholestanol inserted into the plasma membrane by 5 min and was detected in endosomes by 30-60 min by which time >50% of probe was internalized, whereas Cy5-ethyl ester remained in the extracellular fluid (FIG. 7B). After 4 h, Cy5-cholestanol had redistributed from the plasma membrane to Rab5a-positive early endosomes containing $NK_1R$-GFP.

FRET was used to quantitatively assess the capacity of a tripartite probe to target the $NK_1R$ in endosomes. $NK_1R$ with extracellular N-terminal Snap-Tag was expressed in HEK293 cells and cell-surface $NK_1R$ was labelled with non-membrane permeant SNAP-Surface™ 549 photostable fluorescent substrate. SP (10 nM, 30 min) evoked translocation of all detectable SNAP-549 to endosomes. SNAP-549-$NK_1R$ and Cy5-cholestanol FRET was detected within 5 min of adding Cy5-cholestanol, and increased for >75 min (data not shown). Analysis of the subcellular origin of FRET confirmed that >75% of the signal was intracellular, consistent with probe association with endosomal $NK_1R$.

Compound 1 antagonized SP (3 nM, $EC_{80}$)-stimulated $Ca^{2+}$ signaling in HEK-$NK_1R$ cells ($pIC_{50}$ spantide I: 8.23±0.21: Compound 1: 8.44±0.29) and thus retains antagonist activity. Since the tripartite probe was depleted from the plasma membrane and redistributed to endosomes after 4 h, the capacity of Compound 1 and spantide to influence $NK_1R$ endosomal signaling was compared 4 h after preincubation with HEK293.

When cells were preincubated with Compound 1, spantide or SR140333 for 30 min, and then immediately challenged with SP, all antagonists blocked activation of nuclear and cytosolic ERK (FIG. 7C), indicating effective antagonism of cell-surface $NK_1R$. In contrast, when cells were pulse incubated with antagonists for 30 min, washed and then stimulated with SP 4 h later. Compound 1 alone inhibited nuclear ERK and none of the antagonists inhibited cytosolic ERK. Compound 1 did not affect isoprenaline-induced activation of nuclear ERK, which is mediated by the endogenous $1β_2$-adrenergic receptor (not shown). Thus, conjugation to cholestanol delivers probes to $NK_1R$-positive early endosomes, and after pulse incubation Compound 1 causes sustained and selective antagonism of the endosomal not cell-surface NKiR.

Figure 8:
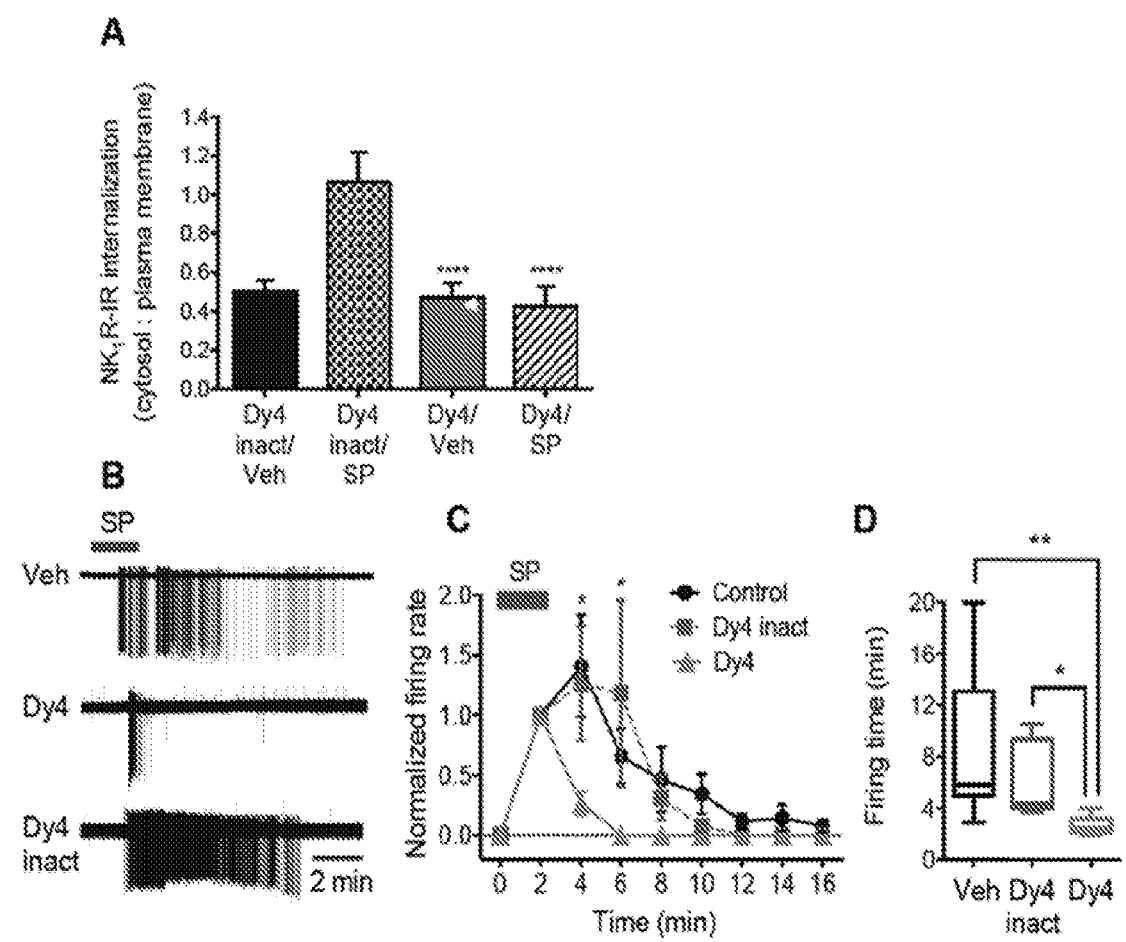
FIG. 8: Graphical representations of SP-evoked NK$_1$R endocytosis and excitability in spinal neurons. A. Effects of endocytic inhibitors on SP-stimulated NK$_1$R-IR endocytosis in lamina I dorsal horn neurons of rat spinal cord slices. Results show ratio of cytosolic to plasma membrane NK$_1$R-IR in rat spinal neurons. ****P<0.0001, n=6 neurons per treatment. Veh, vehicle. B-D. Effects of endocytic inhibitors on SP-evoked firing of rat spinal neurons. B shows representative traces. C shows firing rate normalized to response at 2 min (P>0.05). D shows firing time as duration of response to last action potential. n=7 cells per treatment, 17 rats, *P<0.05, **P<0.01.

Next, slices of rat spinal cord were incubated with Compound 1 or spantide to assess whether antagonism of the endosomal $NK_1R$ blocks sustained SP-induced excitation of spinal neurons. After incubation for 60 min, the spinal cord slices were washed, incubated in antagonist-free medium for 60 min, and then challenged with SP. In vehicle- or spantide-pretreated slices, SP caused brisk action potential discharge that was sustained after SP removal (FIG. 8A-C). Compound 1 did not suppress the initial excitation, but prevented the action potential discharge that was sustained after SIP removal. Thus, an endosomally-targeted and membrane-anchored $NK_1R$ antagonist effectively blocks persistent SP-induced activation of spinal neurons and causes long-lasting analgesia.

To evaluate whether antagonism of endosomal $NK_1R$ blocks nociception, intrathecal injections of Cy5-cholestanol, spantide or Compound 1 were made to mice. After 3 h, capsaicin was injected into the paw. Compound 1, but not spantide or Cy5-cholestanol markedly inhibited capsaicin-evoked hyperalgesia for >120 min (FIG. 8D). When administered 30 min after capsaicin, intrathecal spantide had a small and transient (I h) analgesic effect, whereas Compound 1 caused a delayed (3 h), persistent (>6 h) and substantial (>50% inhibition) analgesia (FIG. 8E). Cy5-cholestanol was detected in laminae I-III neurons after 6 h, suggesting effective probe delivery (not shown). When injected intrathecally 3 h before intraplantar formalin, Compound 1 markedly inhibited both phases of nocifensive behavior more effectively than spantide or SR140333 (FIG. 8F, G). When injected intrathecally 36 h after intraplantar CFA, Compound 1 was analgesic after 4 h, and analgesia was sustained for >6 h, whereas the analgesic actions of SR140333 and spantide were minor and transient (FIG. 8H, I).

To assess the general utility of endosomal targeting, the small molecule $NK_1R$ antagonist L733-0660 was conjugated to cholestanol via a polyethylene glycol linker (Compound 2). When injected intrathecally 3 h before intraplantar capsaicin, Compound 2 showed sustained analgesia for >4 h, whereas the effect of L-733,060 was small and transient (FIG. 8J).

Thus, an endosomally-targeted and membrane-anchored $NK_1R$ antagonist effectively blocks persistent SP-induced activation of spinal neurons and causes long-lasting analgesia. Although spantide and Compound 1 were similarly stable in human CSF for >4 h, after intrathecal injection to mice spantide was extensively metabolized whereas Compound 1 was stable (not shown). Endosomal targeting and retention may contribute to the in vivo stability of spantide-cholestanol.

Example 9: CLR Signaling and Pain Transmission

CGRP and SP can be co-released from primary sensory neurons to evoke pain and neurogenic inflammation. In view of the fact that CGRP has been shown to stimulate βarr-dependent endocytosis of CLR, an investigation as to whether CLR signals from endosomes was conducted. CGRP (1 nM) was found to decrease CLR-RLuc8/KRas-Venus BRET and increase CLR-RLuc8/Rab5a-Venus BRET (not shown), consistent with CLR endocytosis. PS2 and dynaminK44E inhibited these effects. CGRP stimulated nuclear and cytosolic ERK. Dy4 and dynaminK44E prevented activation of nuclear but not cytosolic ERK. Compound 4, comprising the CLR antagonist $CGRP_{8-37}$ was found to effectively antagonise CGRP-stimulated $Ca^{2+}$ signaling in HEK-CLR/RAMP1 cells. After preincubation with HEK293 cells for 30 min, both $CGRP^{8-37}$ and Compound 4 inhibited CGRP-stimulated activation of nuclear and cytosolic ERK (data not shown). When cells were pulse incubated with antagonists for 30 min, washed and then stimulated with CGRP 4 h later, Compound 4 alone strongly inhibited nuclear ERK and neither antagonist strongly inhibited cytosolic ERK.

Figure 9:
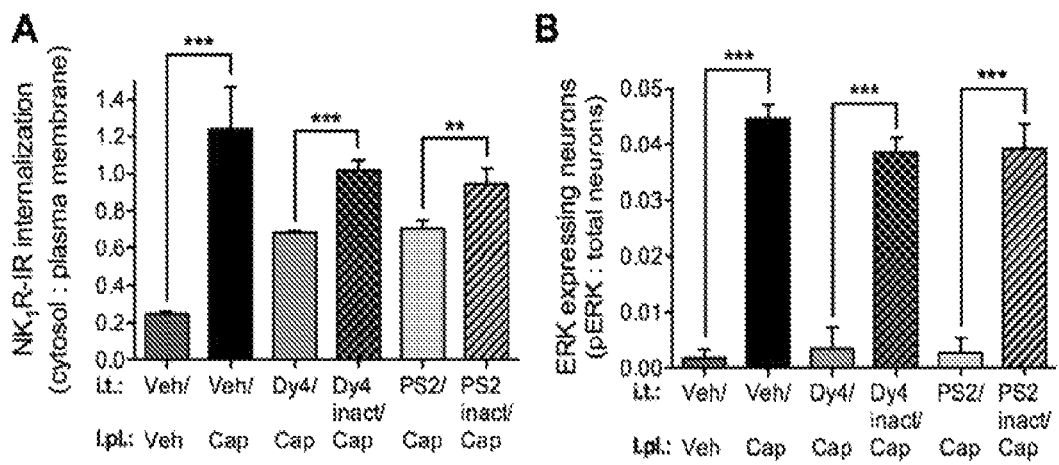
FIG. 9: Graphical representations of NK$_1$R endocytosis and ERK signaling in spinal neurons. Vehicle (Veh), Dy4, Dy4 inact, PS2 or PS2 inact was injected intrathecally (i.t.) to rats 30 min before intraplantar (i.pl.) injection of vehicle or capsaicin (Cap). A shows ratio of cytosolic to plasma membrane NK$_1$R-IR, and B shows ratio of pERK-IR to NeuN-IR neurons. LI, LII, lamina I, II. Scale A, 10 μm; C, 25 μm. P<0.01, *P<0.001. n=3 rats; NK$_1$R, analysis of 6 cells per condition, p-ERK analysis of 6 fields per condition.
Figure 10:
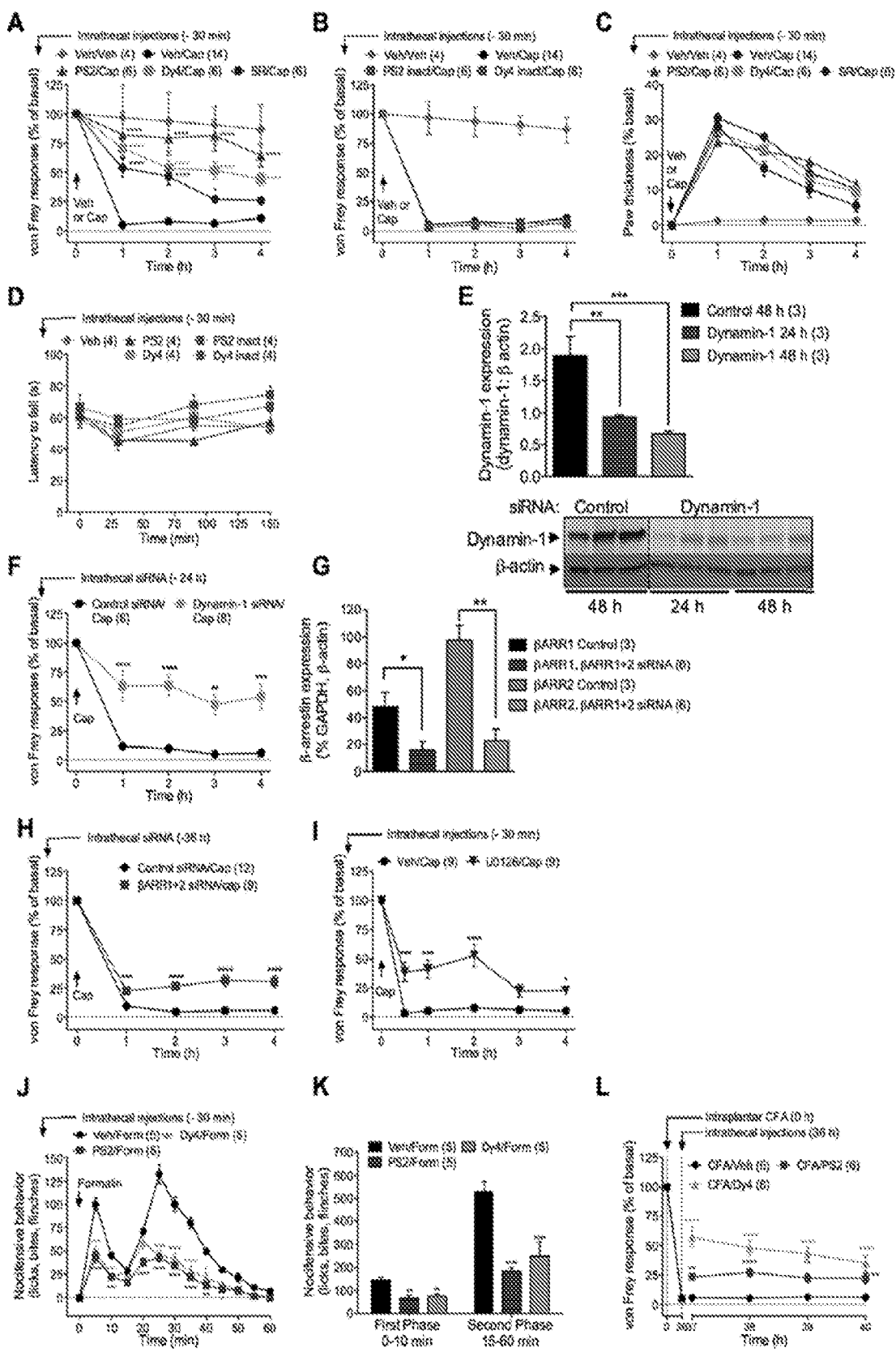
FIG. 10: Graphical representations of mechanical hyperalgesia, inflammatory edema and motor coordination in mice. A-D. Vehicle (Veh) or endocytic inhibitor was injected intrathecally 30 min before intraplantar injection of capsaicin (Cap) or vehicle into the left paw. A, B show von Frey withdrawal responses of injected left paw, C shows edema responses of injected left paw. D. Vehicle or endocytic inhibitor was injected intrathecally 30 min before measurement of rotarod latency. E-H. siRNA to dynamin-1 (E, F), βarr1+2 (G, H) or control siRNA was injected intrathecally 24-48 h before intraplantar injection of capsaicin into the left paw. E, G show knockdown in the dorsal horn of dynamin-1 determined by Western blot (E), and (arr1+2 determined by RT-PCR (G). F, H show von Frey withdrawal responses of injected left paw. I. Vehicle or U0126 was injected intrathecally 30 min before intraplantar injection of capsaicin or vehicle into the left paw. von Frey withdrawal responses of injected left paw were measured. J, K. Vehicle or endocytic inhibitor was injected intrathecally 30 min before intraplantar injection of formalin (Form). Nocifensive behavior was measured for 60 min. J shows response kinetics. K shows responses during first and second phases. L. CFA was injected into the left paw 36 h before intrathecal injection of vehicle or endocytic inhibitor. von Frey withdrawal responses of injected left paw were measured. *P<0.05, P<0.01, *P<0.001, ****P<0.0001 compared to Veh/Cap, control siRNA, Veh/Form or CFA/Veh. (n), mouse number.
Figure 11:
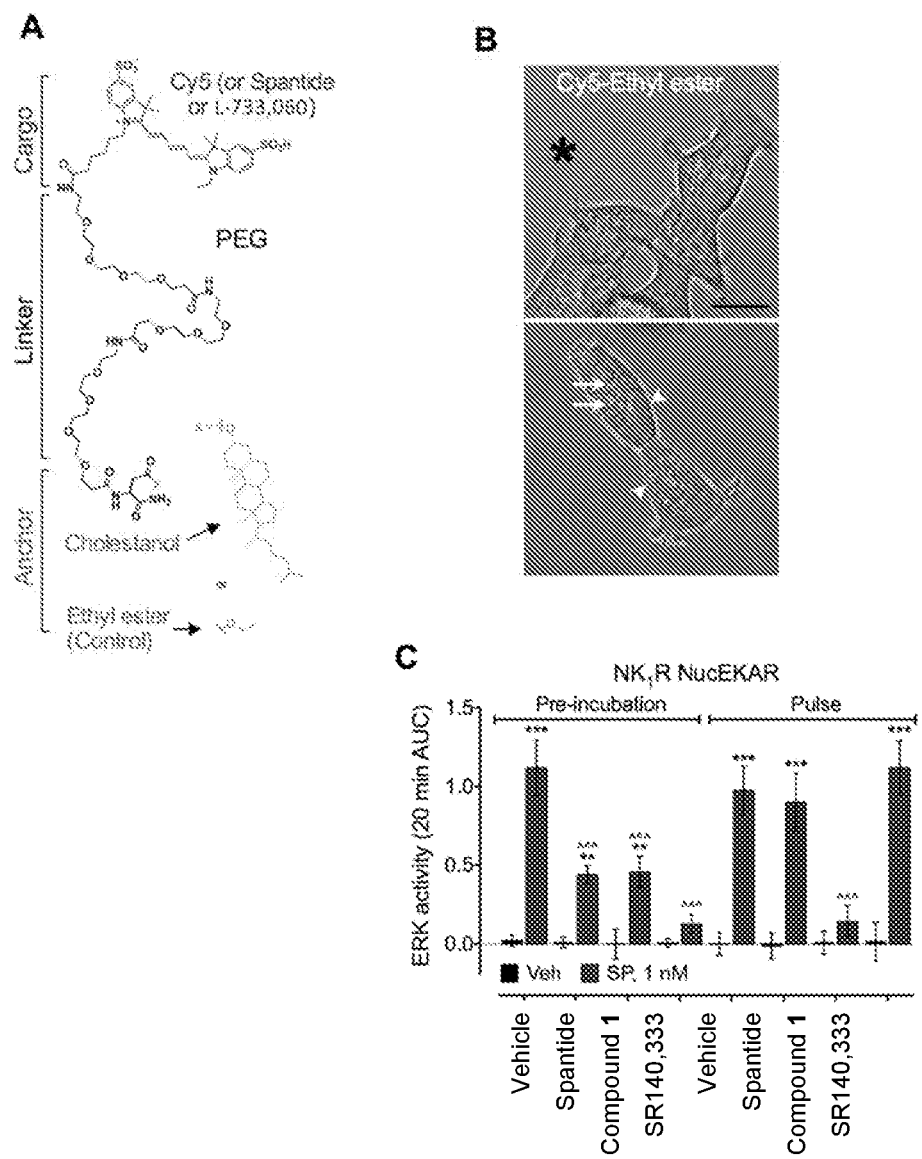
FIG. 11: Graphical representations of targeting endosomal NK$_1$R using tripartite probes. A. Structure of tripartite probes with Cy5, spantide or L-733,060 cargo. B. Uptake of Cy5-ethyl ester or Cy5-cholestanol (Cy5-Chol) (30 min, 37° C.) in HEK293 cells. Asterisk, extracellular; arrowheads, plasma membrane; arrows, endosomes. Scale, 10 m. C. SP activation of nuclear ERK in HEK293 cells. Pre-incubation: Cells were pre-incubated with spantide (Span), Compound 1 or SR140,333 (SR) for 30 min, and then immediately stimulated with SP (in the presence of inhibitors). Pulse incubation: Cells were pulse incubated with spantide, Compound 1 or SR140,333 for 30 min, washed, and stimulated with SP 240 min after washing. Results shows area under curve (AUC) over 20 min. P<0.01, *P<0.001 SP to vehicle (Veh); ^^^P<0.001 SP with vehicle to SP with spantide, spantide-cholestanol, or SR140,333. n=31-83 cells.
Figure 12:
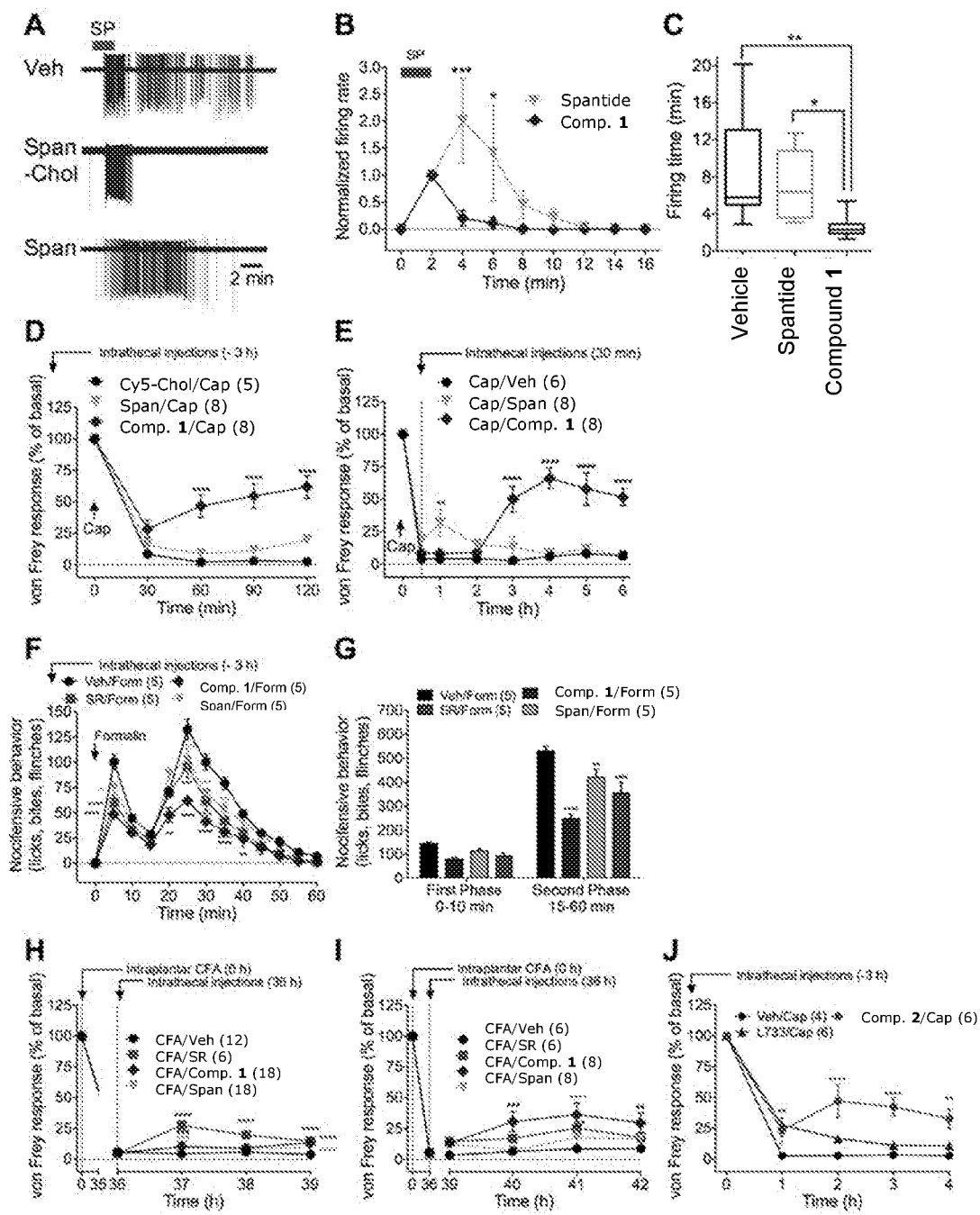
FIG. 12: Graphical representations of Targeting of endosomal NK$_1$R in spinal neurons using tripartite probes. A-C. SP-evoked firing of rat spinal neurons. A shows representative traces. B shows firing rate normalized to response at 2 min (events. 2 min$^{-1}$: Compound 1, 196.6±81.6; spantide, 242.6±95.9; P>0.05). C shows firing time as duration of response to last action potential. n=7 cells per treatment, 18 rats, *P<0.05, P<0.01, *P<0.001. D, E. Vehicle (Veh), Cy5-cholestanol (Cy5-Chol), spantide (Span) or Compound 1 was injected intrathecally to mice 3 h before (D) or 30 min after (E) intraplantar injection of capsaicin (Cap) into the left paw. von Frey withdrawal responses of injected left paw are shown. F, G. Vehicle, SR140,333 (SR), spantide or Compound 1 was injected intrathecally to mice 30 min before intraplantar injection of formalin (Form). Nocifensive behavior was measured for 60 min. F shows response kinetics, G shows responses during first and second phases. H, I. CFA was injected into the left paw of mice 36 h before intrathecal injection of vehicle, SR140,333 (SR), spantide or Compound 1. von Frey withdrawal responses of injected left paw were measured in different groups of mice 36-39 h (H) or 39-42 h (I) after CFA. J. Vehicle (Veh), L-733,060 (L733) or Compound 4 was injected intrathecally to mice 3 h before intraplantar injection of capsaicin into the left paw. von Frey withdrawal responses of injected left paw are shown. P<0.01, **P<0.0001 to Cy5-cholestanol or vehicle. (n), mouse number.
Figure 13:
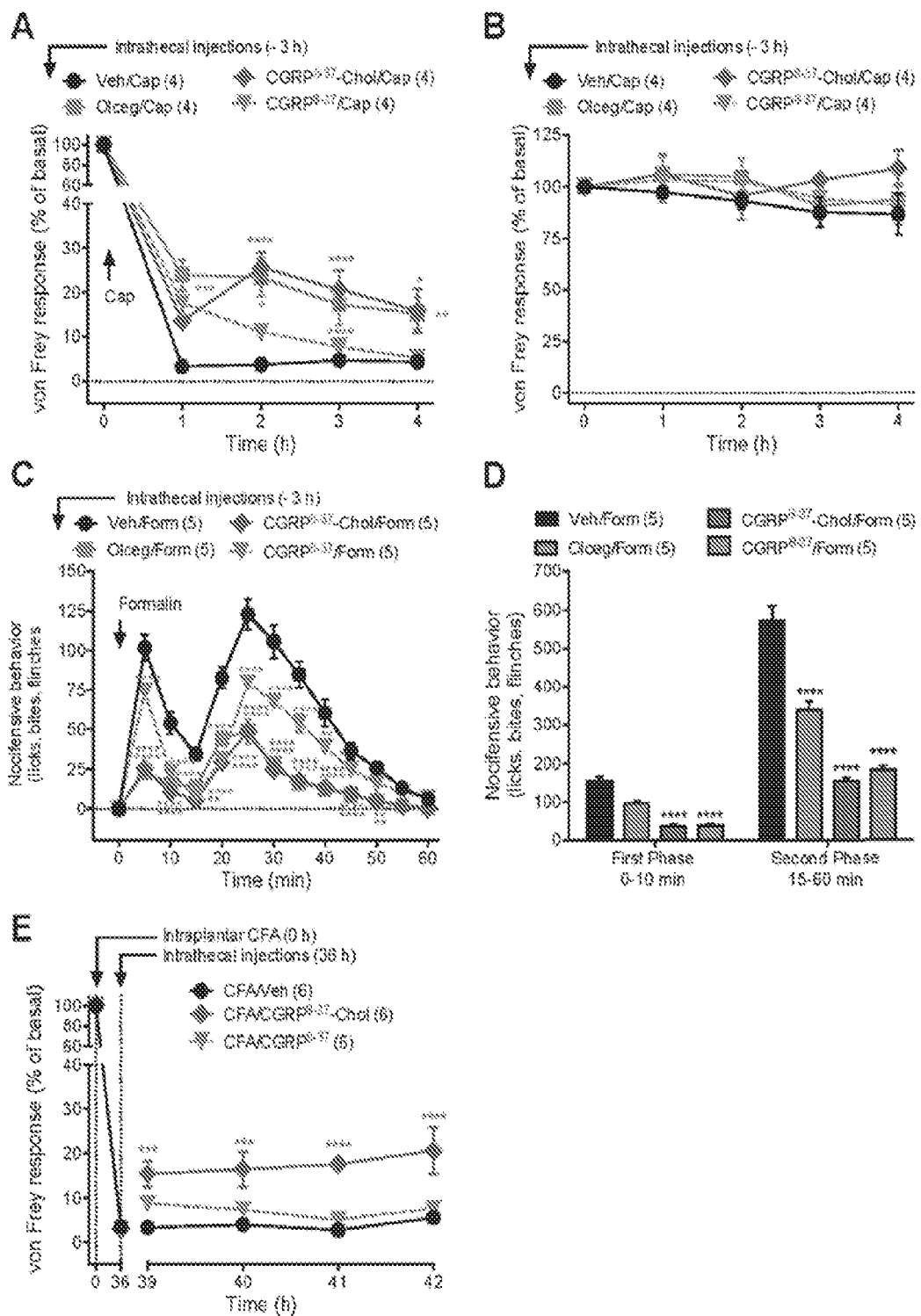
FIG. 13: Graphical representations of CGRP-mediated mechanical hyperalgesia in mice. A, B. Vehicle (Veh), Olcegepant (Olceg), Compound 4 or free CGRP$^{8-37}$ was injected intrathecally 3 h before intraplantar injection of capsaicin (Cap) into the left paw. A shows von Frey withdrawal responses of the injected left paw, and B shows von Frey withdrawal responses of the non-injected right paw. C, D. Vehicle, Olcegepant, Compound 4 or free CGRP$^{8-37}$ was injected intrathecally 3 h before intraplantar injection of formalin into the left paw. Nocifensive behavior was measured for 60 min. C shows response kinetics, D shows responses during first and second phases. E. Complete Freund's adjuvant (CFA) was injected into the left paw of mice 36 h before intrathecal injection of vehicle, Compound 4 or free CGRP$^{8-37}$. von Frey withdrawal responses of injected left paw were measured 39-42 h after Complete Freund's adjuvant. *P<0.05, P<0.01, *P<0.001, ****P<0.0001 to vehicle. (n), mouse number.

When injected intrathecally to mice, Compound 4 and the small molecule CLR antagonist olcegepant similarly inhibited capsaicin-evoked mechanical hyperalgesia and both phases of formalin-evoked nocifensive behavior more completely than $CGRP_{8-37}$ (FIG. 9). Treatments did not affect paw withdrawal of the non-injected paw (FIG. 9B). Compound 4 but not $CGRP_{8-37}$ reversed CFA-induced hyperalgesia (FIG. 9E). Compound 4 also inhibited formalin-evoked nocifensive behaviour (FIG. 9C, D).

These results suggest that endosomal CLR signaling controls excitability of spinal neurons and pain transmission.

Example 10: Activation of Endosomal $NK_1R$

GR73632 [Ava-Phe-Phe-Pro-N-MeLeu-Met-$NH_2$] is a neurokinin 1 receptor agonist that is not susceptible to cleavage by the endothelin converting enzyme 1 (Hagan R. M. et al., *Neuropeptides* 1991, 19, 127-35). GR73632 was conjugated to cholestanol (Compound 3) or ethyl ester (GR73632-ethyl ester) via a flexible PEG linker. The effect of these compounds in HEK293 cells expressing NK1R was then studied.

Calcium mobilization assays revealed an approximate 100 fold decrease in potency of GR73632-ethyl ester ($\log_{EC50}$=−7.28) and Compound 3 ($\log_{EC50}$=−6.80) when compared to the free agonist ($\log_{EC50}$=−9.03). Bioluminescence resonance energy transfer (BRET) assays show that Compound 3, compared to GR73632, does not induce recruitment of βarrs. These data suggest that Compound 3 bypasses the plasma membrane neurokinin 1 receptor.

Forster resonance energy transfer (FRET) assays were performed using extracellular-regulated kinase activity reporter (EKAR) biosensors targeted towards the cytosol and the nucleus for the spatiotemporal delineation of extracellular signal related kinase (ERK) activation (Harvey C. D. et al, *PNAS* 2008, 105, 19264-9). Preliminary data in FRET assays imaged over 20 minutes showed that the free GR73632 agonist stimulated sustained cytosolic and nuclear ERK phosphorylation whereas no ERK phosphorylation was observed in response to the GR73632-ethyl ester. Compound 3 stimulates sustained nuclear ERK phosphorylation but no cytosolic ERK.

These results indicate that Compound 3 is a selective agonist of the endosomal $NK_1R$.

Example 11: Biological Methods

Alexa568-SP.

AlexaFluor568 NHS ester (Invitrogen, Carlsbad, Calif.; 6.3 μmol) was incubated with SP (1.48 μmol) and triethylamine (2.9 μmol) in DMF (500 μl) (15 h, room temperature, RT). Alexa568-SP was purified by reverse-phase HPLC. The product was confirmed by mass spectrometry: m/z 1012.8, calcd for $C_{96}H_{127}N_{19}O_{24}S_3[M+2H^+]$ m/z 1012.9.

cDNAs.

BRET probes $NK_1R$-RLuc8, KRas-Venus, Rab5a-Venus, βarr1-YFP, βarr2-YFP, $G\alpha_q$-RLuc8 and $G\gamma_2$-Venus have been described (Kocan, M., et al., *Frontiers in Endocrinology*, 2010, 1, 12; Lan, T. H., et al., *Traffic*, 2012, 13, 1450-1456). CytoEKAR and NucEKAR and CytoCKAR and pmCKAR were from Addgene (plasmids 18680, 18681, 14870, 14862, respectively). CytoEpac2-camps was from M Lohse (University of Wurzburg) and pmEpac2-camps was from D Cooper (University of Cambridge). GFP-dynamin and GFP-dynamin K44E have been described (Schmidlin, F. et al., *J Biol Chem*, 2001, 276, 25427-25437). Human $NK_1R$ with extracellular N-terminal Snap-Tag® was from Cisbio. Full length and truncated 6312 rat HA-$NK_1R$ have been described (Dery, O., Defea, K. A. & Bunnett, N. W., *Ameri-* can *Journal of Physiology*, 2001, 280, C1097-1106). RLuc8 fusions of these constructs were generated by removal of the stop codon by PCR and subcloning into a pcDNA3.1-RLuc8 vector. HA-CLR and Myc-RAMP1 have been described (Cottrell, G. S. et al., *J Biol. Chem.*, 2007, 282, 12260-12271). CLR-RLuc was from M. Bouvier (University de Montreal).

Cell Lines, Transfection.

HEK293 cells stably expressing rat $NK_1R$ with N-terminal HA11 epitope have been described (Roosterman, D. et al. *P.N.A.S.*, 2007, 104, 11838-11843). HEK293 cells were transiently transfected using polyethylenimine (Polysciences) or FuGene (Promega). Cells were grown in Dulbecco's modified Eagle's medium (DMEM) supplemented with 5% FBS (37° C., 5% $CO_2$).

BRET.

HEK293 cells were transfected with the following cDNAs: 1 µg $NK_1R$-RLuc8 or 1 µg CLR-RLuc8+1 µg Myc-RAMP1+4 µg KRas-Venus, 4 µg Rab5a-Venus, 4 µg βarr1-YFP, or 4 µg βarr2-YFP; or 1 µg $NK_1R$+0.5 µg $Gα_q$-RLuc8+1 µg Gβ$_1$+4 µg Gγ$_2$-Venus; or 1 µg $NK_1R$+0.5 µg $Gα_q$-RLuc8+1 µg Gβ$_1$+1 µg Gγ$_2$+4 µg Rab5a-Venus. After 48 h, cells were equilibrated in Hank's balanced salt solution (HBSS) at 37° C., and incubated with the RLuc substrate coelenterazine h (5 µM, 15 min). BRET ratios were determined using a microplate reader LUMIstar Omega (BMG LabTech) before and after challenge with SP (0.1-10 nM) or vehicle (d$H_2O$).

FRET Biosensors of Compartmentalized Signaling.

HEK293 cells were transfected with 55 ng/well rat $NK_1R$ with N-terminal HA. 11 epitope tag (HA-$NK_1R$) or CLR plus RAMP1 and 40 ng/well FRET biosensors. FRET was assessed 48 h after transfection, following serum restriction (0.5% FBS overnight). For experiments using clathrin or dynamin siRNA, cells were transfected with 55 ng/well rat HA-$NK_1R$, 40 ng/well FRET biosensor and 25 nM/well scrambled, clathrin or dynamin ON-TARGETplus SMARTpool siRNA (GE Dharmacon). FRET was assessed 72 h after transfection, following serum restriction (0.5% FBS overnight). Cells were equilibrated in HBSS at 37° C. and FRET was analyzed using a GE Healthcare INCell 2000 Analyzer. For GFP/RFP emission ratio analysis, cells were sequentially excited using a FITC filter (490/20) with emission measured using dsRed (605/52) and FITC (525/36) filters, and a polychroic optimized for the FITC/dsRed filter pair (Quad4). For CFP/YFP emission ratio analysis, cells were sequentially excited using a CFP filter (430/24) with emission measured using YFP (535/30) and CFP (470/24) filters, and a polychroic optimized for the CFP/YFP filter pair (Quad3). Cells were imaged every 1 min, allowing image capture of 14 wells per minute. Baseline emission ratio images were captured for 4 min. Cells were challenged with an $EC_{50}$ concentration of SP (1 nM), GGRP (1 nM) or vehicle, and images were captured for 20 min. Cells were then stimulated with the positive control (200 nM phorbol 12,13-dibutyrate for ERK; 200 nM phorbol 12,13-dibutyrate with phosphatase inhibitor cocktail for PKC; 10 µM forskolin, 100 µM 3-isobutyl-1-methylxanthine, 100 nM $PGE_1$ for cAMP) for 10 min to generate a maximal increase, and positive emission ratio images were captured for 4 min. Data were analyzed as described and expressed as emission ratios relative to baseline for each cell ($F/F_0$). Cells with >10% change in $F/F_0$ after stimulation with positive controls were selected for analysis.

FRET Assays of Endosomal $NK_1R$ Targeting.

HEK293 cells were transfected with 50 ng/well of $NK_1R$ with extracellular N-terminal Snap-Tag®. After 48 h, the cell surface $NK_1R$ was labeled with SNAP-Surface™ 549 photostable fluorescent substrate (New England Biolabs) (1 µM, 30 min, 37° C. in DMEM, 0.5% BSA). Cells were washed, recovered in DMEM for 30 min, and stimulated with SP (10 nM, 30 min, 37° C.) to induce $NK_1R$ endocytosis. Cells were incubated with Cy5-cholestanol (200 nM, 37° C.). SNAP-549/Cy5 sensitized emission FRET was analysed by confocal microscopy using sequential excitation with Argon (514 nm)/HeNe (633 nm) lasers and emission at 570-620 nm (SNAP-549 donor) and 670-750 nm (Cy5 FRET and Cy5 acceptor) before and after addition Cy5-cholestanol. Controls included non-transfected HEK293 cells (acceptor only) and HEK293 cells not treated with Cy5-cholestanol (donor only). FRET was analysed as described and expressed as emission ratios relative to controls ($F/F_0$).

$Ca^{2+}$ assays.

$[Ca^{2+}]_i$ was measured as described (Jensen, D. D. et al., *J Biol Chem*, 2014, 289, 20283-20294). HEK293 cells transiently expressing HA-$NK_1R$ or HA-CLR/Myc-RAMP1 were loaded with Fura2-AM (2 µM). To compare the antagonistic capacity of spantide, Compound 1, L-733,060, Compound 2, CGRP$^{8-37}$, or Compound 4, cells were pre-incubated for 30 min with antagonists, and were then challenged with SP (3 nM, $EC_{50}$) or CGRP (10 nM, $EC_{80}$).

ELISA.

HEK293 cells transiently transfected with HA-$NK_1R$ or HA-$NK_1R$δ312 were fixed in PFA (30 min). For analysis of total expression, cells were permeabilized using 0.5% NP-40 in TBS (30 min) after fixation. Cells were incubated in blocking buffer (1% skim milk powder, 0.1M $NaHCO_3$, 4 h, RT), and then anti-HA (1:5,000, Sigma. Overnight, 4° C.). Cells were washed and incubated with anti-mouse horseradish peroxidase-conjugated antibody (1:2,000, 2 h, RT). Cells were washed and stained using the SIGMAFAST OPD substrate (SigmaAldrich). Absorbance at 490 nm was measured using an EnVision plate reader (PerkinElmer Life Sciences). Values were normalized to HEK293 cells transfected with pcDNA3 or to untreated cells.

$NK_1R$ Trafficking in Cell Lines.

HEK-$NK_1R$ cells were plated on poly-D-Lysine coated glass chamber slides or coverslips and cultured for 48 h. To examine uptake of fluorescent SP, cells were incubated in HBSS with Alexa568-SP (100 nM, 20 min, 4° C.), washed, incubated for 30 min at 37° C., and fixed in 4% paraformaldehyde, 100 mM PBS pH 7.4 (PFA, 20 min, 4° C.). Cells were examined by confocal microscopy. To examine $NK_1R$ and $Gα_q$ trafficking, cells were incubated in HBSS with SP (100 nM, 15 min) or vehicle and fixed. Cells were blocked in PBS, 0.2% saponin, 3% normal goat serum (1 h, RT). Cells were incubated in primary antibodies: rat anti-HA (1:1,000; Roche), rabbit anti-$Gα_q$(1:2,000, C-19; Santa Cruz Biotechnology), mouse anti-EEA1 (1:100, 610457; BD Biosciences) (overnight, 4° C.). Cells were washed and incubated with donkey anti-rat Alexa488 (1:500), donkey anti-rabbit Alexa568 (1:1,000), and donkey anti-mouse Alexa647 (1:1,000) (Life Technologies or Jackson ImmunoResearch) (1 h, RT). Cells were examined by super-resolution microscopy.

Cy5 Tripartite Probe Uptake.

HEK293 cells were plated on poly-D-lysine-coated glass coverslips. Cells were infected with CellLight® Rab5a-RFP (Life Technologies) or were transfected with rat $NK_1R$-GFP. After 24 h, cells were equilibrated in HBSS, imaged at 37° C. by confocal microscopy, and incubated with Cy5-cholestanol or Cy5-ethyl ester (1.5 µM). Cells expressing $NK_1R$-GFP were incubated with SP (10 nM).

Animals.

Institutional Animal Care and Use Committees approved all studies. Rats (Sprague-Dawley, males, 3-8 weeks) and mice (C57BL/6, males, 6-10 weeks) were from the Monash Animal Research Platform, the Animal Resources Centre, Western Australia, and Harlan Laboratories. Animals were maintained in a temperature-controlled environment with a 12 h light/dark cycle and free access to food and water. Animals were killed by anesthetic overdose and thoracotomy.

Spinal Cord Slices.

Parasagittal slices (340-400 µm) were prepared using a vibratome from the lumbar region of the rat spinal cord in ice-cold sucrose-based artificial CSF (sACSF) (mM: 100 sucrose, 63 NaCl, 2.5 KCl, 1.2 $NaH_2PO_4$, 1.2 $MgCl_2$, 25 glucose, 25 $NaHCO_3$; 95% $O_2$/5% $CO_2$). Slices were transferred to N-Methyl-D-Glucamine (NMDG)-based recovery ACSF (rACSF) (mM: 93 NMDG, 93 HCl, 2.5 KCl, 1.2 $NaH_2PO_4$, 30 $NaHCO_3$, 20 HEPES, 25 glucose, 5 Na ascorbate, 2 thiourea, 3 Na pyruvate, 10 $MgSO_4$, 0.5 $CaCl_2$; 95% $O_2$/5% $CO_2$, 15 min, 34° C.). Slices were transferred to normal ACSF (mM: 125 NaCl, 2.5 KCl, 1.25 $NaH_2PO_4$, 1.2 $MgCl_2$, 2.5 $CaCl_2$, 25 glucose, 11 $NaHCO_3$; 95% $O_2$/5% $CO_2$) containing 10 µM MK-801 (45 min, 34° C.), then maintained at RT.

Electrophysiology.

Slices of rat spinal cord were transferred to a recording chamber and superfused with normal ACSF (2 ml·$min^{-1}$, 36° C.). Dodt-contrast optics were used to identify large (capacitance ≥20 pF), putative NKiR-positive neurons in lamina I based on their position, size and fusiform shape with dendrites that were restricted to lamina I. Slices were preincubated with Dy4 or Dy4 inact (both 30 µM, 0.03% DMSO) for 10 min before recording, or were preincubated with Compound 1, spantide, Compound 4 or $CGRP^{8-37}$ (all 1 µM in 0.01% DMSO) for 60 min, washed and incubated in antagonist-free ACSF for a further 60 min before recording. PS2 was not soluble in the low concentrations of DMSO required for electrophysiology. Large, NKiR-positive, presumed nociceptive lamina I neurons were visually identified as described (Imlach, W. L., et al., *Molecular Pharmacology*, 2015, 88, 460-428). Spontaneous currents were recorded in cell-attached configuration (Multiclamp 700B, Molecular Devices, Sunnyvale, Calif.), sampled at 10 kHz, high pass filtered at 1 Hz, and capacitatively coupled action potential events were analyzed using Axograph X, V 1.4.4 (Axograph). Patch electrodes (resistance 2.5-3.5 MΩ) contained KMES-based internal solution (mM: 105 KMES, 20 NaCl, 5 HEPES, 10 BAPTA, 1.5 $MgCl_2$, 4 MgATP, 0.4 NaGTP, 0.1% biocytin; 285-295 mosmol·$l^{-1}$) to facilitate subsequent recordings of action potential properties in whole-cell configuration. Recordings were made in the presence of CNQX (6-cyano-7-nitroquinoxaline-2,3-dione) (10 µM; AMPA/kainate receptor antagonist), picrotoxin (100 µM; $GABA_A$ receptor antagonist), strychnine (0.5 µM; glycine and acetylcholine receptor antagonist), and AP5 ((2R)-amino-5-phosphonovaleric acid; (2R)-amino-5-phosphonopentanoate) (100 µM; NMDA receptor antagonist) to minimize presynaptic influences on action potential properties. Slices were challenged by superfusion with SP or CGRP (1 µM) for 2 min. CGRP stimulated slices were challenged with SP at the end of the experiment to confirm co-expression of CGRP and SP receptors. Recordings were sampled at 10 kHz and filtered with a high pass filter at 1 Hz and firing rate was measured in two-minute interval bins. At the end of each cell-attached recording, whole-cell recordings were made in current-clamp mode to confirm retention of normal action potential firing. Data were only included in the analysis if cells had action potential amplitudes that were ≥50 mV above threshold to ensure viable neurons were included. Cells were filled with biocytin and sections were processed to confirm $NK_1R$ expression by immunofluorescence. The firing rate for each cell was normalized to the response at the 2 min time point, which was not significantly different between groups. The firing time was determined as the duration of the response to last action potential. To assess synaptic transmission, whole-cell configuration recordings were made under control conditions or after exposure to Dy4 or Dy4 inact; a bipolar stimulating electrode was placed at the dorsal root entry zone, and electrically-evoked excitatory postsynaptic currents recorded as described (Imlach, W. L., et al., *Molecular Pharmacology*, 2015, 88, 460-428). To assess $NK_1R$ endocytosis, spinal cord slices (400 µm) were incubated with SP (1 µM, 5 min), fixed in PFA (4 h, RT), cryoprotected, and were processed to localize the $NK_1R$.

Neuropeptide Release.

Slices (0.4 mm) of mouse dorsal spinal cord (combined cervical, thoracic, lumbar-sacral segments) were superfused (0.4 ml·$min^{-1}$) with Krebs' solution (mM: NaCl 119, $NaHCO_3$ 25, $KH_2PO_4$ 1.2, $MgSO_4$ 1.5, $CaCl_2$ 2.5, KCl 4.7, D-glucose 11 mM; 95% $CO_2$/5% $O_2$, 37° C.) containing 0.1% BSA, 1 µM phosphoramidon and 1 µM captopril. Tissues were superfused with Dy4, PS2, inactive analogues (30 µM) or vehicle (0.3% DMSO/saline) for 30 min. Tissues were then superfused with capsaicin (0.3 µM, 10 min) in the presence of inhibitors or controls. Superfusate (10 min collections, 4 ml) was collected before, during and after capsaicin stimulation, and analyzed for SP-IR and CGRP-IR (Bertin Pharma). Endocytic inhibitors did not interfere with immunoassays. Detection limits of the assays were 2 pg·$ml^{-1}$ for SP-IR and 5 pg·$ml^{-1}$ for CGRP-IR. Results are expressed as fmol·$g^{-1}$·20 $min^{-1}$.

$NK_1R$ Endocytosis in Rat Spinal Neurons.

Dy4, Dy4 inact, PS2, PS2 inact (all 50 µM), or vehicle (1% DMSO/saline) was injected intrathecally (10 µl, L3/L4) into conscious rats. After 30 min, rats were sedated (5% isoflurane) and capsaicin (12.5 µg) or vehicle (20% ethanol, 10% Tween 80, 70% saline) was injected subcutaneously into the plantar surface of one hindpaw (25 µl). After 10 min, rats were transcardially perfused with PBS and then 4% PFA. The spinal cord was removed, immersion fixed in PFA (2 h, 4° C.), and cryoprotected (30% sucrose, PBS, 24 h, 4° C.). The spinal cord (T12 to L4) was embedded in OCT and 30 m serial coronal sections were cut into 48-well plates containing PBS. Free-floating sections were blocked in PBS containing 10% normal horse serum (1 h, RT). Sections were incubated with mouse anti-NeuN (1:20,000; AbCam) and either rabbit anti-$NK_1R$ (1:5,000, #94168) or rabbit anti-pERK (1:200; Cell Signaling Technology) in PBS containing 3% normal horse serum (48 h, 4° C.). Sections were washed (4×20 min in PBS) and incubated with donkey anti-rabbit Alexa488 (1:8,000) and donkey anti-mouse Alexa568 (1:2,000 (Life Technologies) (1 h, RT). Sections were washed, incubated with DAPI (10 µg/ml, 5 min), and mounted in Vectashield (Vector Laboratories).

Mechanical Hyperalgesia, Nocifensive Behavior and $NK_1R$ Endocytosis in Spinal Neurons in Mice.

Mice were acclimatized to the experimental apparatus and environment for 1-2 h on 2 successive days before experiments. Mechanical hyperalgesia was assessed by paw withdrawal to stimulation of the plantar surface of the hind-paw with graded von Frey filaments. On the day before the study, von Frey scores were measured in triplicate to establish a baseline for each animal. To assess edema of the paw, hindpaw thickness was measured using digital calipers before and after treatments. For intraplantar injections, mice were sedated (5% isoflurane). Capsaicin (5 µg), Complete Freund's Adjuvant (CFA, 2 mg/ml), or vehicle (capsaicin, 20% ethanol, 10% Tween 80, 70% saline; CFA, saline) was injected subcutaneously into the plantar surface of the left hindpaw (10 µl). von Frey scores (left and right paws) and paw thickness (left paw) were measured for 30-240 min after capsaicin, and 36-40 h after injection of CFA. Results are expressed as percent pre-injected values. For assessment of nocifensive behavior, mice were sedated and formalin (4%, 10 µl) was injected subcutaneously into the plantar surface of the left hindpaw. Mice were placed in a Perspex container and nocifensive behavior (flinching, licking, biting of the injected paw) was recorded for 60 min. The total number of nocifensive events was subdivided into acute (I, 0-10 min) and tonic (II, 10-60 min) phases. At the end of experiments, mice were transcardially perfused with PBS and PFA, and the spinal cord was removed and processed to localize the $NK_1R$ by immunofluorescence, as described for rats. Investigators were unaware of test agents.

Intrathecal Injections in Mice.

Intrathecal injections (5 µl, L3/L4) were made into conscious mice. Dy4, Dy4 inact, PS2, PS2 inact (all 50 µM), SR-140333 (15 µM), SM-19712 (8 mM), U0126 (100 µM), or vehicle (1% DMSO/saline) was injected intrathecally 30 min before intra-plantar injection of capsaicin or formalin, or 36 h after CFA. Spantide (50 µM), Compound 1 (50 µM), L-733,060 (100 nM), Compound 2 (100 nM), $CGRP^{8-37}$ (10 µM), Compound 4 (10 µM), olcegepant (10 µM), or Cy5-cholestanol (10 µM) was injected intrathecally 3 h before or 30 min after intra-plantar injection of capsaicin, 3 h before formalin, or 36 h after CFA.

Intrathecal siRNA in Mice.

Cationic liposome and adjuvant anionic polymer (polyglutamate) were used to deliver siRNA. siRNA targeting mouse dynamin-1 (5' (S-S) UAA GUG UCA AUC UGG UCU C dTdT 3') or control siRNA (5' (S-S) CGU ACG CGG AAU ACU UCG AUU dTdT), or siRNA targeting mouse β-arr1 (sense 5' AGC CUU CUG CGC GGA GAA U dTdT 3', antisense 5' dTdT U CGG AAG ACG CGC CUC UUA 5') plus mouse f3-arr2 (sense: 5' CCU ACA GGG UCA AGG UGA A dT dT 3', antisense: 5' UUC ACC UUG ACC CUG UAG G dT dT 3') or control siRNA (sense: 5' AAG GCC AGA CGC GAA UUA U dT dT, 3' antisense: 5' AUA AUU CGC GUC UGG CCU U dT dT 3') (Dharmacon) (50 ng, 0.5 µl of 100 ng/µl stock) was mixed with 0.5 µl of adjuvant polyglutamate (0.1 µg/µl stock) and 1.5 µl sterile 0.15 M NaCl. Liposome solution, cationic lipid 2-{3-[bis-(3-aminopropyl)-amino]-propylamino}-N-ditetradecylcarbamoylmethyl-acetamide (DMAPAP) and L-α-dioleoyl phosphatidylethanolamine (DOPE) (DMAPAP/DOPE, 1/1 M:M) (2.5 µl of 200 µM) was added to siRNA/adjuvant, vortexed for 1 min, and incubated (30 min, RT). The siRNA lipoplexes were administered to mice by intrathecal injection (L1-L4, 5 µl). After behavioral testing (24-48 h), the spinal cord (L1-L4) was collected for analysis of dynamin-1 expression by Western blotting and 3-arrestin-1 and 3-arrestin-2 expression by q-PCR.

Western Blotting.

Cell Lines.

HEK293 cells were lysed in 150 µl of RIPA buffer containing HALT protease and phosphatase inhibitors (Thermo Scientific). Samples were sonicated on ice, centrifuged and supernatant (20 µg protein) was fractionated by 10% SDS-PAGE and transferred to PVDF membranes. Membranes were blocked (1 h, RT) in Odyssey blocking buffer (LI-COR Biosciences), and incubated with sheep anti-dynamin-$1^{54}$ (1:1,000) or rabbit anti-clathrin (1 µg/ml, Abcam) antibodies in PBS, 0.2% Tween-20, 50% Odyssey blocking buffer (16 h, 4° C.). Membranes were washed and incubated with donkey anti-goat 680 or goat anti-rabbit 680 (1:10,000; LI-COR Biosciences) (1 h, RT). Membranes were washed and imaged with the LI-COR Odyssey infrared scanner. Membranes were stripped and re-probed with rabbit anti-β-actin (1:1,000; Cell Signaling Technology, 16 h, 4° C.), washed, incubated with goat anti-rabbit 800 (1:10,000, 1 h at RT, LI-COR), and re-imaged. Signals were quantified using ImageJ (NIH). Spinal cord. The dorsal half of the spinal cord was placed in 100 µl of ice cold RIPA buffer containing HALT protease and phosphatase inhibitors (Thermo Scientific). Tissues were homogenized, centrifuged, and supernatant (20 µg protein) was separated by 10% SDS-PAGE and transferred to PVDF membranes. Membranes were processed to detect dynamin-1 and β-actin as described.

q-PCR.

Mouse lumbar spinal cord (L1-L4) was placed in RNAlater (Qiagen) and total RNA was isolated using RNeasy RNA Isolation kit (Qiagen). Total RNA (500 ng) was reverse-transcribed using Superscript™ III cDNA Synthesis Kit (Invitrogen). Water was added to ⅓ of the sample for the negative reverse transcriptase (RT) control. The remaining ⅔ of the sample was reverse transcribed using Superscript III Reverse Transcriptase. cDNA was amplified using Eppendorf RealPlex Real Time PCR System. Twenty microliters of amplification reaction included cDNA template, TaqMan Universal Master Mix and TaqMan Gene Expression Assays for one of the following genes (catalog no.): ARRB2 (Mm00520666_g1), ARRB1 (Mm00617540_m1), ACTB (Mm02619580_g1), Gapdh (hs00363153_m1). All samples were amplified in triplicates. The relative abundance (R) of each transcript was estimated according to the $\Delta C_t$ method using the following formula: $2^{\Delta CT}$. $C_t$ is the mean critical threshold at which the increase in fluorescence is the exponential. Assuming efficiency of PCR reaction was 100%, it corresponds to a 2-fold increase in amplicon amount with each cycle of PCR. With this assumption, $2^{\Delta CT}$ was used to calculate relative transcript abundance. These values were normalized to an average of housekeeping genes (β-actin and GAPHD).

Rotarod.

Mice were acclimatized by 3 trials on 2 successive days before experiments. Mice were trained to remain on the rotarod for three consecutive periods. On the experimental day, three baseline time trials (cut-off 120 s) were recorded. Dy4, PS2, inactive analogues (50 µM), or vehicle was injected intrathecally (5 µl, L3/L4). After 30 min, mice were placed on the rotarod with accelerating velocity for up to 120 s. Times were recorded in 3 successive trials, and latency time to fall was determined at 30, 90 and 120 min Confocal Microscopy, Image Analysis.

Tissues and cells were observed using a Leica SP8 confocal microscope using HCX PL APO 40× (NA 1.30) and HCX PL APO 63× (NA 1.40) oil objectives. Z stacks were collected of NKiR-positive neurons in lamina I of the dorsal horn. Video projections of Z stacks were made using Imaris Software (Bitplane). $NK_1R$ endocytosis and pERK expression were quantified using ImageJ. To quantify $NK_1R$ internalization in lamina I neurons, the border of the cytoplasm of the neuronal soma was defined by NeuN fluorescence, and $NK_1R$ fluorescence within 5 pixels (0.5 µm) of the border was defined as plasma membrane-associated receptor. The ratio of plasma membrane to cytosolic $NK_1R$-IR fluorescence was determined in >6 lamina I neurons per condition. To quantify ERK activation, the ratio of the number of pERK-IR neurons to total Neu-N-positive neurons in lamina I was determined in >6 fields (×40 objective) per condition.

Metabolic Stability of the Compounds of the Invention.

To assess stability in cerebrospinal fluid, spantide or Compound 1 (10 μg/ml) was incubated in human cerebrospinal fluid (0-4 h, 37° C.), and then snap frozen. Proteins were precipitated using ACN. To assess stability in the spinal cord, spantide or Compound 1 was injected intrathecally to mice (10 μM, 5 μl, L3/L4). After 3 hours, a spinal cord segment 5 mm on either side the injection site was removed and snap frozen. Tissues were crushed with a glass rod in a mixture of methanol (30 μl) and EDTA/KF (60 μl, 0.1 M EDTA, 4 g/l KF), vortexed and centrifuged to remove lipids. Peptides were extracted from the pellet with 0.5% formic acid in 75% ACN/H$_2$O (100 μl). Samples were analyzed assayed by LC/MS using a Waters Xevo TQ or TQD triple quadrupole mass spectrometer coupled to a Waters UPLC. Peptides were separated by HPLC (Supelco Ascentis Express Peptide ES C18 column, 50×2.1 mm, 2.7 μm) with 0.05% formic acid in H$_2$O and ACN as solvents. Peptides were quantified by comparison to calibration standards (50-50,000 ng/ml).

Statistical Analyses.

Data are presented as mean±SEM. Differences were assessed using Student's t test for two comparisons. For multiple comparisons, differences were assessed using one- or two-way ANOVA followed by Dunnett's multiple comparison test (BRET, pain, rotarod, Western blot), Tukey's multiple comparison test (FRET, NK$_1$R internalization, ERK activation in spinal neurons, synaptic transmission), Sidak's multiple comparisons test (average firing rate of spinal neurons), or Dunn's multiple comparisons test (duration of firing response of spinal neurons).

The invention claimed is:
1. A tripartite compound of formula (I):

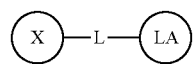
(I)

wherein
LA is a lipid anchor that promotes insertion of the compound into a plasma membrane wherein
LA is represented by formula (IIaa):

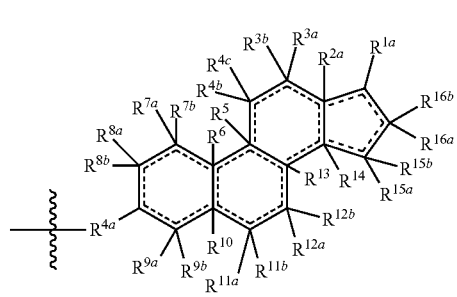
(IIaa)

wherein
$R^{1a}$ is a $C_{1-12}$ alkyl, $C_{2-12}$ alkenyl, $C_{2-12}$ alkynyl, or $C_{1-12}$ alkoxy group;

$R^{2a}$, $R^{3a}$, $R^{3b}$, $R^{4b}$, $R^{4c}$, $R^5$, $R^6$, $R^{7a}$, $R^{7b}$, $R^{8a}$, $R^{8b}$, $R^{9a}$, $R^{9b}$, $R^{10}$, $R^{11a}$, $R^{11b}$, $R^{12a}$, $R^{12b}$, $R^{13}$, $R^{14}$, $R^{15a}$, $R^{15b}$, $R^{16a}$, $R^{16b}$ are independently H, $C_{1-3}$alkyl, hydroxyl, alkoxy, or amino, or $R^{3a}$ $R^{3b}$, $R^{4b}$ $R^{4c}$, $R^{7a}$ $R^{7b}$, $R^{8a}$ $R^{8b}$, $R^{9a}$ $R^{9b}$, $R^{11a}$ $R^{11b}$, $R^{12a}$ $R^{12b}$, $R^{15a}$ $R^{15b}$, and/or $R^{16a}$ $R^{16b}$ are taken together to give =O (double bond to oxygen);

$R^{4a}$ is CH$_2$, O, NH or S, and

〰〰〰 represents a single or a double bond;

L is a linker moiety of 1 nm to 50 nm in length, wherein L is represented by formula (IVa):

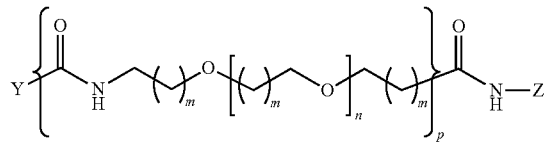
(IVa)

wherein
Z is an attachment group of the linker to the lipid anchor (LA); wherein Z is defined by:
  a1) —C$_1$-C$_{10}$alkyl, —C$_2$-C$_{10}$alkenyl-, —C$_2$-C$_{10}$alkynyl-, —C$_1$-C$_{10}$alkylC(O)—, —C$_2$-C$_{10}$alkenylC(O)—, or —C$_2$-C$_{10}$alkynylC(O)—; or
  b1) together with the adjacent amine amide NH, is an amino acid or a C terminally amidated amino acid, wherein the amino acid is selected from the group consisting of aspartic acid, glutamic acid, asparagine, glutamine, histidine, cysteine, lysine, arginine, serine, and threonine; and wherein the amino acid is attached to the lipid anchor via its side-chain functional group; and Y is an attachment group of the linker L to the modulator (X), wherein
  a2) Y is defined by a covalent bond, —O—, —NH—, —S—, —C(O)—, —C(O)NH—, —C(O)O—, —O—C(O)—, —NH—C(O)—, or —C(O)S—; or
  b2) Y, when taken together with the adjacent amido group, is defined by:
  a. an alpha amino acid selected from aspartic acid, glutamic acid, asparagine, glutamine, histidine, cysteine, lysine, arginine, serine or threonine; wherein the alpha amino acid is optionally attached to the modulator X via the side-chain functional group of at least one of said alpha amino acid; or
  b. a beta, gamma or delta amino acid comprising a side-chain functional group which is also found in aspartic acid, glutamic acid, asparagine, glutamine, histidine, cysteine, lysine, arginine, serine or threonine; wherein said beta, gamma or delta amino acid is optionally attached to the modulator X via said side-chain functional group; or
  c. a peptide formed from alpha, beta, gamma or delta amino acids, wherein the peptide comprises at least one alpha, beta, gamma or delta amino acid which has a side-chain functional group which is also found in aspartic acid, glutamic acid, asparagine, glutamine, histidine, cysteine, lysine, arginine, serine or threonine; or combinations thereof, wherein said peptide is attached to the modulator X via at least one of said side-chain functional groups;

m is 1 or 2;
n is from 1 to 20;
p is from 1 to 8; and

X is a modulator of an endosomal GPCR, wherein the endosomal GPCR is an endosomal neurokinin-1 receptor (NK1R), and X is defined by structure X=M-$R^1$— as defined by formula (VI) or by formula (Vb), wherein M is covalently linked via R1 to Y of the linker L:

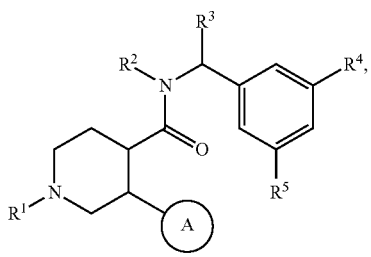

(VI)

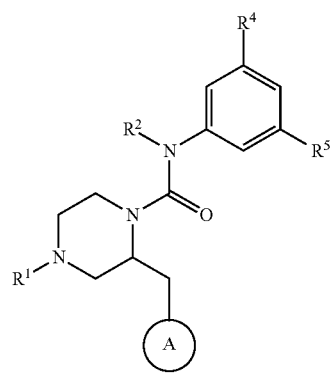

(Vb)

wherein
$R^1$ is defined by —$F^1$—$R^{2'}$—$F^2$—, wherein:
M is covalently linked to $R^{2'}$ via $F^1$ (M-$F^1$—$R^{2'}$—$F^{2'}$—), and
$R^{2'}$ is further covalently linked to Y of the linker L via $F^2$ (M-$F^1$—$R^{2'}$—$F^2$—Y—), and
$F^1$ and $F^2$ independently from each other have a covalent bond to $R^{2'}$;

$R^{2'}$ is defined by:
a3) covalent bond,
b3) linear or branched $C_{1-4}$ alkyl group, optionally having, as a substituent, a 5- to 7-membered aromatic or non-aromatic heterocyclic group, which optionally further contains in addition to carbon atoms 1 to 4 heteroatoms selected from the group consisting of an oxygen atom, sulfur atom and nitrogen atom, and optionally further having one or two oxo as substituents,
c3) 5- to 7-membered non-aromatic heterocyclic group, optionally further containing, besides carbon atoms, 1 or 2 nitrogen atoms, and optionally having 1 to 3 substituents selected from a group consisting of oxo, linear or branched $C_{1-6}$ alkyl, phenyl, linear or branched $C_{1-6}$ alkyl-carbonyl and $C_{1-6}$ alkyl-carbonylamino,
d3) linear or branched $C_{1-6}$ alkyl group, optionally having substituent(s) selected from the group consisting of:
(i) a 5- to 7-membered aromatic or non-aromatic heterocyclic group containing, besides carbon atoms, 1 to 4 nitrogen atoms, and optionally having one or two oxo as substituents,
(ii) (i) a $C_{1-6}$ alkyl-carbonylamino group,
(iii) a mono- or di-$C_{1-6}$ alkylamino group, and
(iv) a $C_{1-6}$ alkoxy group;
e3) linear or branched $C_{1-6}$ alkoxy group,
f3) $C_{3-8}$ cycloalkyl group optionally having 1 or 2 substituents selected from a group consisting of a $C_{1-6}$ alkyl-carbonylamino group, a $C_{1-6}$ alkoxy-carbonylamino group and an amino group,
g3) carbamoyl group,
h3) linear or branched $C_{1-6}$ alkoxy-carbonyl group, or
i3) $C_{1-6}$ alkyl-carbamoyl group; or combinations thereof;
$F^1$ is defined by a covalent bond or by a moiety selected from the list of functional groups consisting of:
—C(=O)—,
—C(=O)—O—,
—C(=O)—N($R^{4'}$), and
—S(=O)$_2$—N($R^{4'}$)—; with $R^{4'}$ being hydrogen atom or linear or branched $C_1$ to $C_{12}$ alkyl;
$F^2$ is defined by a moiety selected from the list of functional groups consisting of:
—C(=O)—,
—C(=O)—C(=O)—,
—C(=O)—(CH$_2$)$_n$—C(=O)— with n=1 to 12,
—C(=O)—(CH$_2$)$_n$— with n=1 to 12,
—C(=O)—O—(CH$_2$)$_n$—C(=O)— with n=1 to 12, and
—C(=O)—O—(CH$_2$)$_n$— with n=1 to 12;
M is defined by the following substituents:
$R^2$ is a hydrogen atom, methyl or cyclopropyl;
$R^3$ is a hydrogen atom or CH$_3$;
$R^4$ and $R^5$ are trifluoromethyl; and
a group represented by

is a group represented by formula

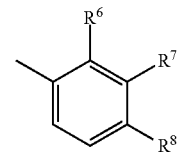

wherein
$R^6$ is a hydrogen atom, methyl, ethyl or isopropyl;
$R^7$ is a hydrogen atom, methyl or chlorine atom; and
$R^8$ is a hydrogen atom, a fluorine atom, a chlorine atom, methyl, or 3-methylthiophen-2-yl;
or a pharmaceutically acceptably salt thereof.

2. The tripartite compound according to claim 1, wherein the partial structure of (VI):

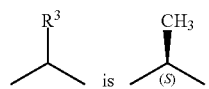

or $R^3$ is hydrogen atom; or a pharmaceutically acceptable salt thereof.

3. The tripartite compound according to claim 1, wherein the moiety —$R^{2'}$—$F^1$-M, which is covalently linked to the linker L by —$F^2$— as shown in the following structure, is as follows:

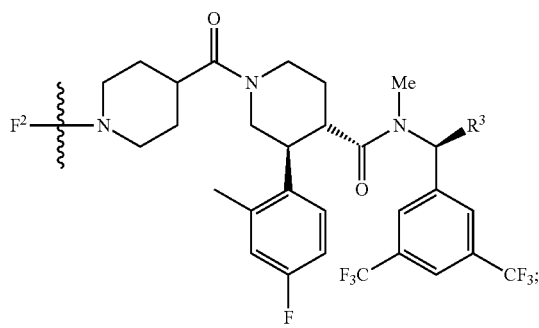

wherein R³ is hydrogen or —CH₃; or a pharmaceutically acceptable salt thereof.

4. The tripartite compound according to claim 1, wherein the moiety —R²′—F¹-M, which is covalently linked to the linker L by —F²— as shown in the following structure, is defined by the following structure:

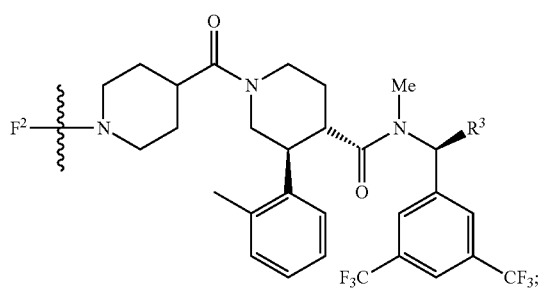

wherein R³ is hydrogen or —CH₃; or a pharmaceutically acceptable salt thereof.

5. The tripartite compound according to claim 1, wherein the moiety —R²′—F¹-M, which is covalently linked to the linker L by F²— as shown in the following structure, is defined by the following structure:

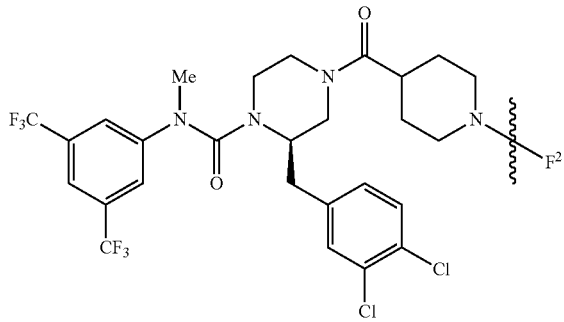

or a pharmaceutically acceptable salt thereof.

6. The tripartite compound according to claim 1, wherein the moiety —F²—R²′—F¹-M, which is covalently linked by Y to the linker L as shown in the following structures, is selected from the group consisting of:

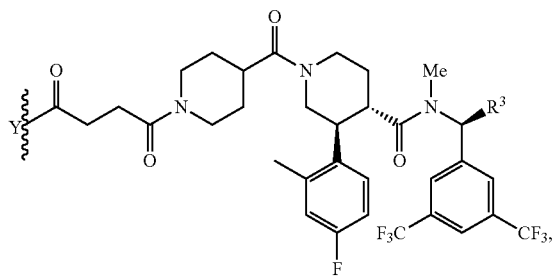

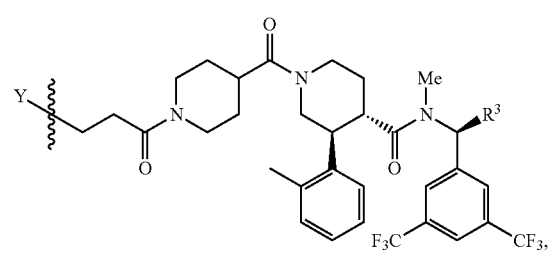

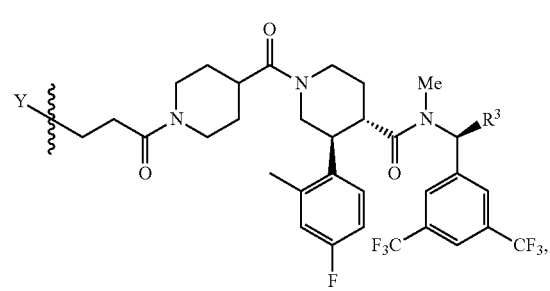

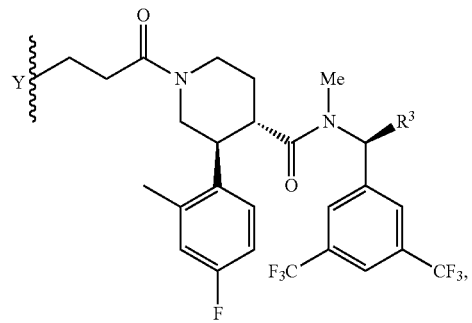

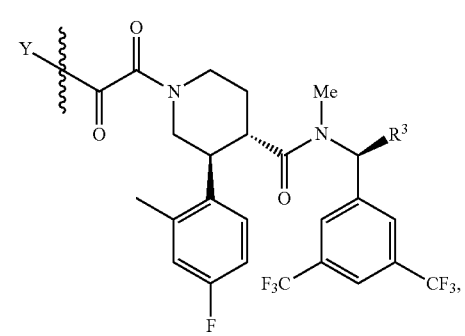

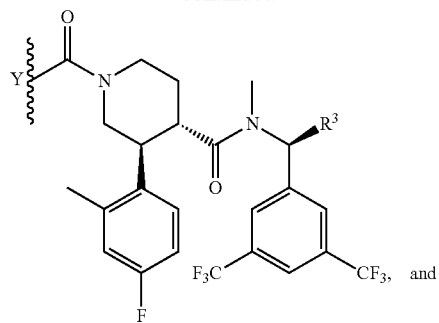

wherein $R^3$ is hydrogen atom or $CH_3$; or pharmaceutically acceptable salt thereof.

7. The tripartite compound according to claim 1, wherein the moiety —$F^2$—$R^{2'}$—$F^1$-M, which is covalently linked by Y to the linker L as shown in the following structures, is selected from the group consisting of:

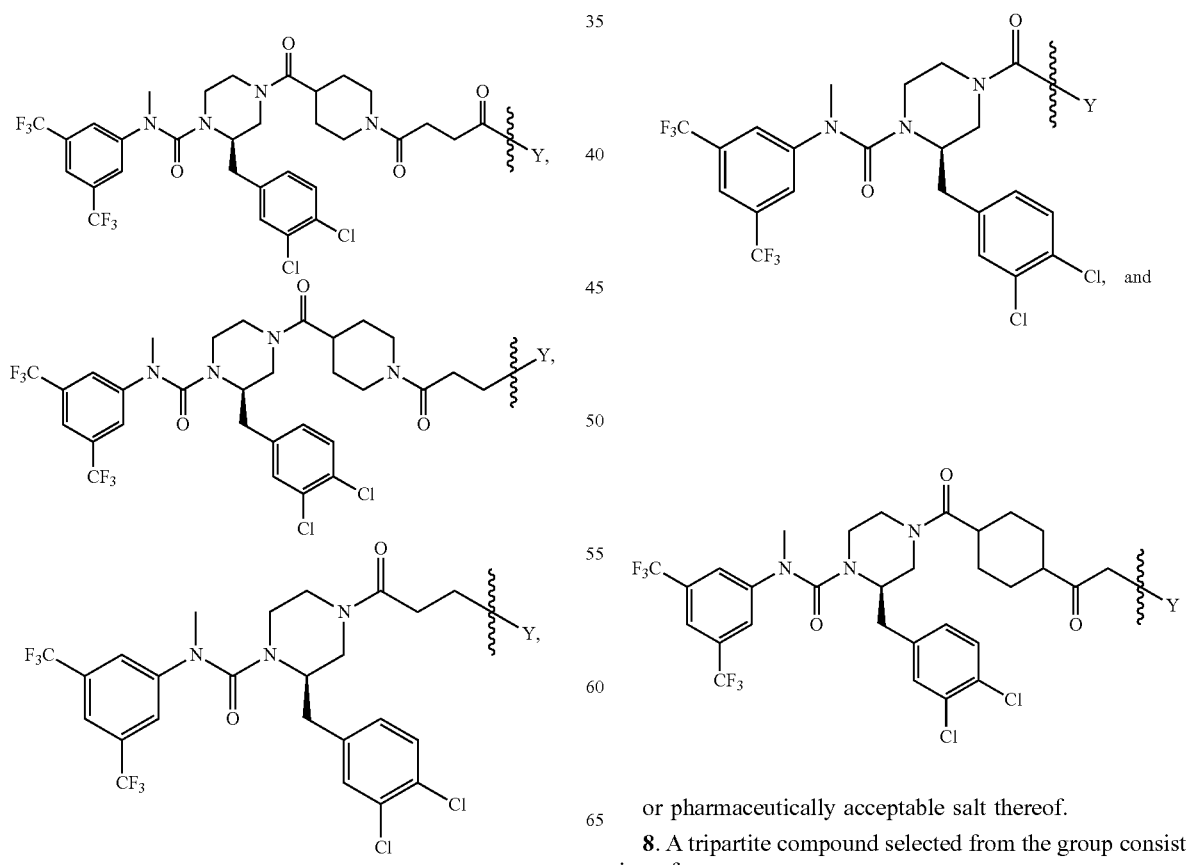

or pharmaceutically acceptable salt thereof.

8. A tripartite compound selected from the group consisting of:

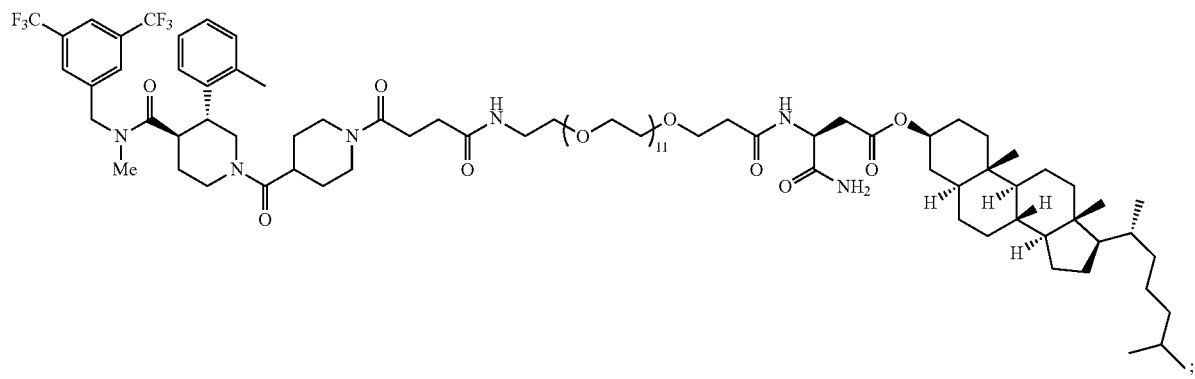
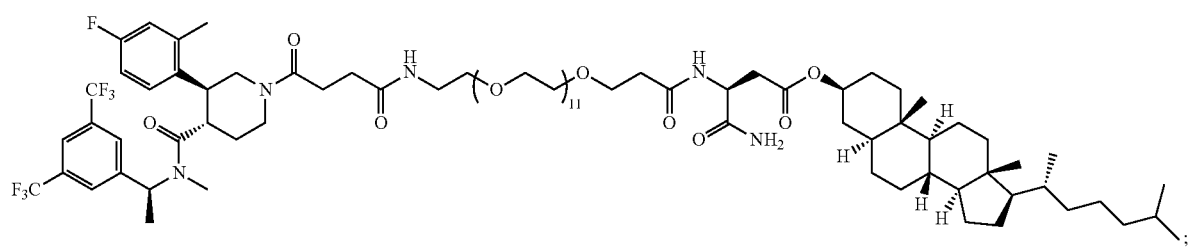
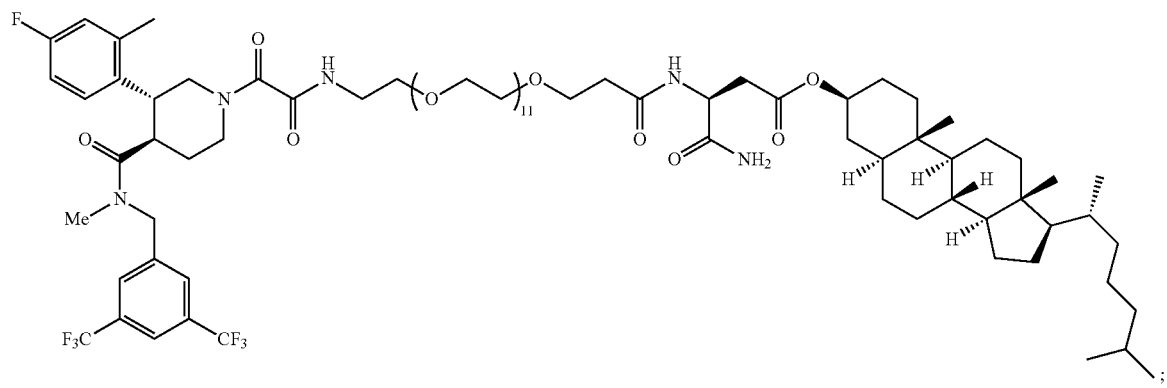
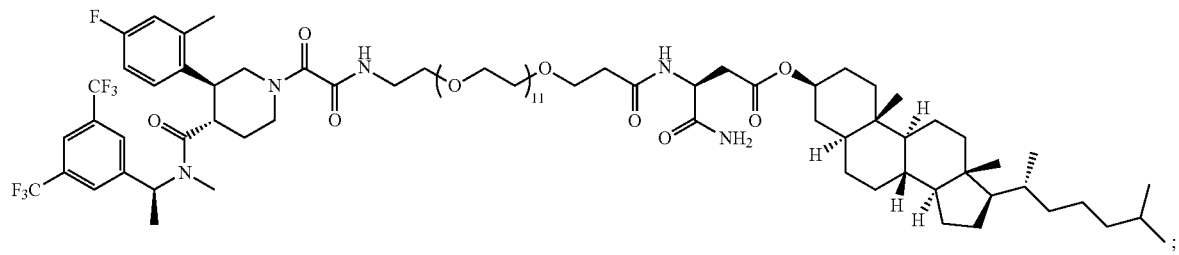
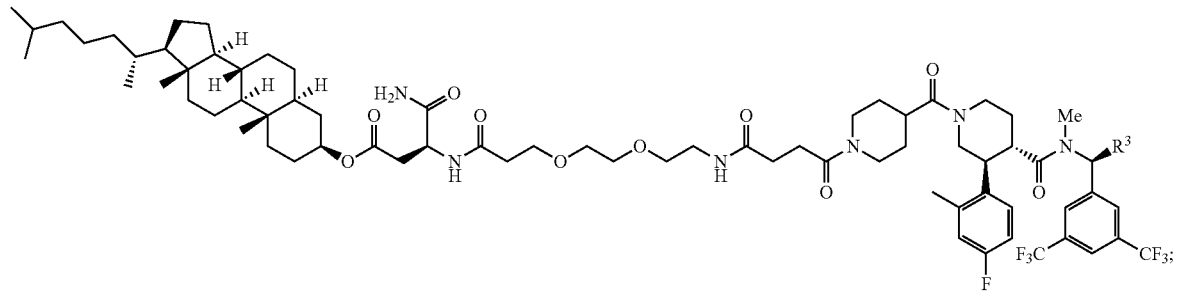

-continued
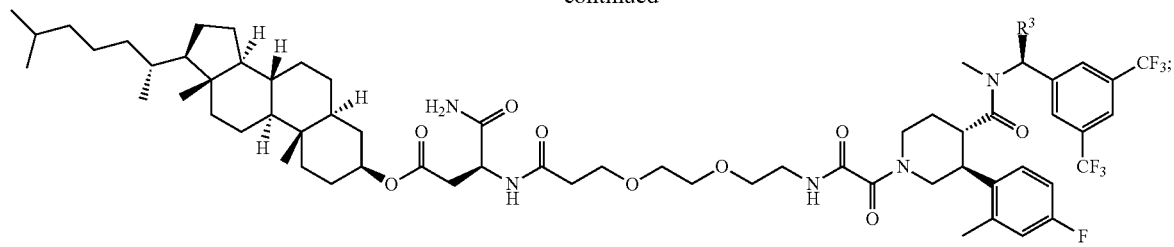
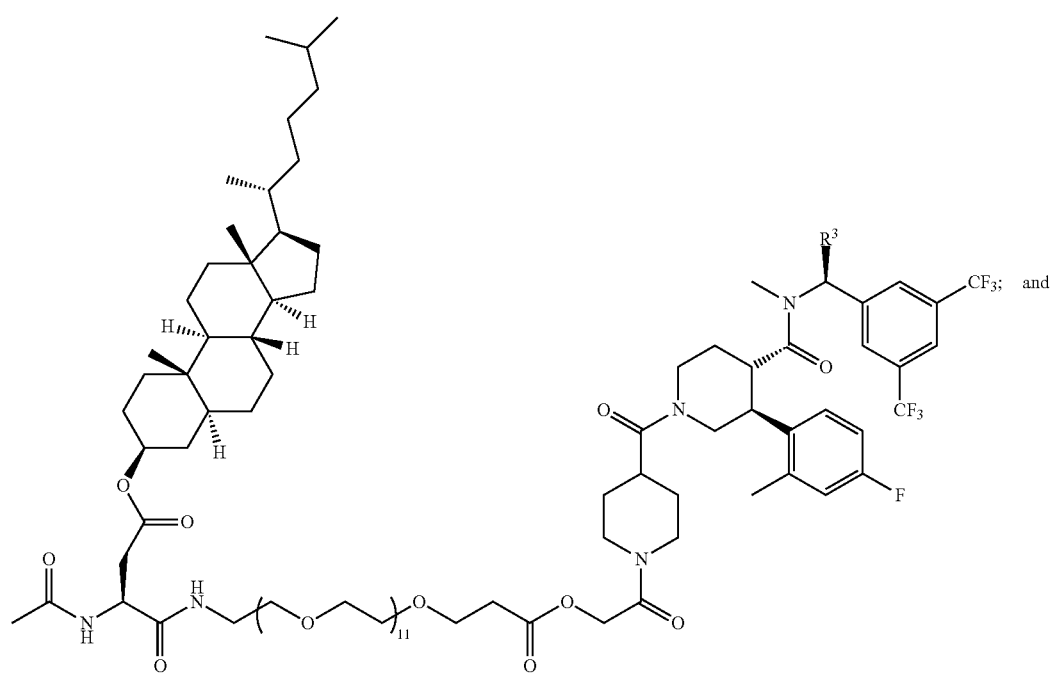
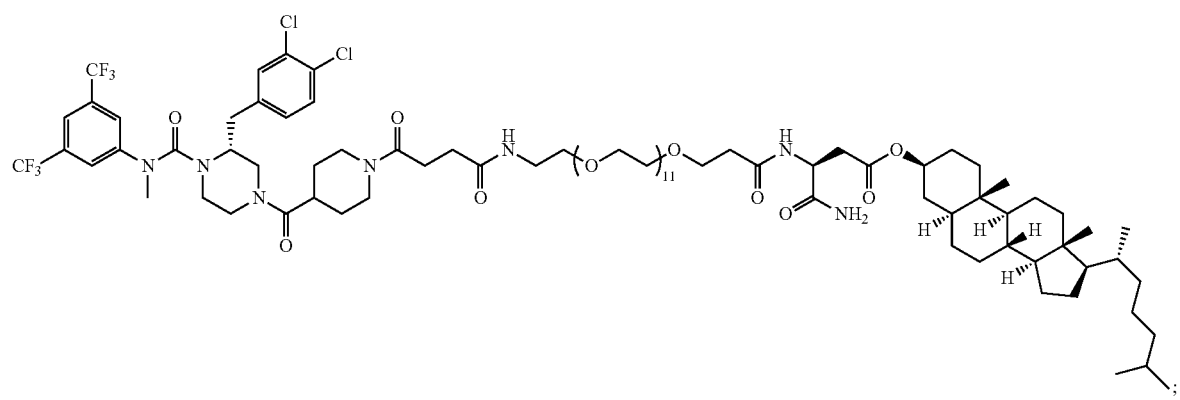
wherein R³ is hydrogen atom or —CH₃; or a pharmaceutically acceptable salt thereof.
9. A pharmaceutical composition comprising a therapeutically effective amount of the tripartite compound according to claim 1, or a pharmaceutically acceptable salt, and at least one pharmaceutically acceptable carrier or diluent.

10. A tripartite compound of formula:
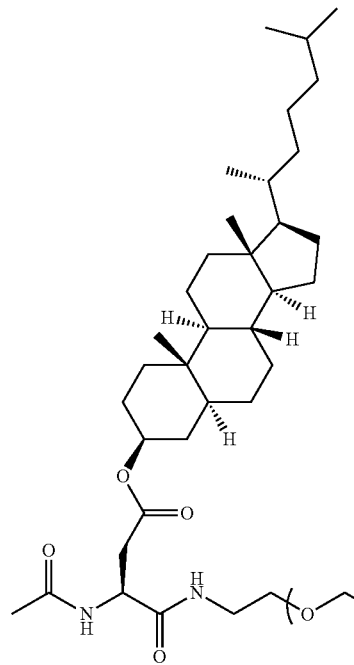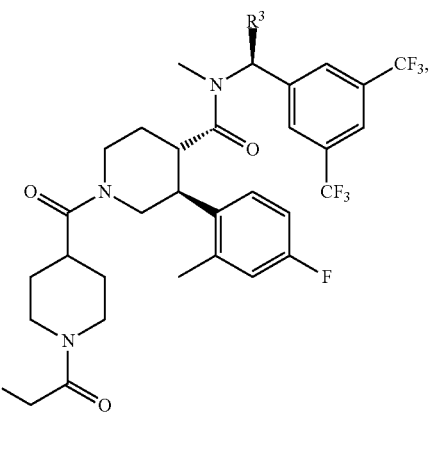
wherein $R^3$ is hydrogen atom or —$CH_3$.
* * * * *